United States Patent
Powell et al.

(10) Patent No.: US 6,946,272 B1
(45) Date of Patent: Sep. 20, 2005

(54) TRANSITION STATE ANALOGS

(75) Inventors: Michael J. Powell, Gaithersburg, MD (US); Richard C. Titmas, Rockville, MD (US); Richard J. Massey, Rockville, MD (US)

(73) Assignee: Proteinix Corporation, Gaithersburg, MD (US)

( * ) Notice: Subject to any disclaimer, the term of this patent is extended or adjusted under 35 U.S.C. 154(b) by 936 days.

(21) Appl. No.: 09/303,716

(22) Filed: Apr. 30, 1999

Related U.S. Application Data

(63) Continuation of application No. 08/333,237, filed on Nov. 2, 1994, now Pat. No. 5,952,462, which is a continuation of application No. 07/190,271, filed on May 4, 1988, now abandoned, which is a continuation-in-part of application No. 06/674,253, filed on Nov. 27, 1984, now Pat. No. 4,888,281, which is a continuation of application No. 06/556,016, filed on Nov. 29, 1983, now abandoned.

(51) Int. Cl.$^7$ ............................ C12N 9/00; C12P 21/06

(52) U.S. Cl. ................................... 435/188.5; 435/68.1
(58) Field of Search ............................. 435/188.5, 68.1

(56) References Cited

OTHER PUBLICATIONS

Gao, C.; et al. (1998) J. Am. Chem Soc. 120(10), 2211-2217.*

* cited by examiner

*Primary Examiner*—Charles L. Patterson, Jr.
(74) *Attorney, Agent, or Firm*—Kramer Levin Naftalis & Frankel LLP; Barry Evans, Esq.

(57) ABSTRACT

Antigens capable of eliciting antibodies which can catalyze chemical reactions, in particular, the cleavage or formation of a peptide linkage, comprising a hapten or a hapten and a suitable carrier molecule are disclosed. Haptens include, among others, silicon and boron containing compounds. Antibodies which are catalytically active for chemical reactions, in particular, the cleavage or formation of a selected peptide linkage or an ester bond, and which are elicited by such antigens are disclosed as well as methods for producing the antibodies and methods for catalyzing the cleavage or formation of a peptide linkage or in ester bond in a molecule.

5 Claims, 30 Drawing Sheets

(VI)

DEPROTECT (VII)

(LAWESSON'S REAGENT)

SCHEME 1

SCHEME 2

SCHEME 2 (CONTINUED)

Antiviral Activity of Clones AHIV 1.3,
AHIV 1.6 and AHIV 2.0 in HIV-1 Replication
and Cell Fusion Assays Dose Dependent Inhibition by Clone AHIV 1.3
of HIV-1 p24 gag Production in
Infected H9 Cells DOSE DEPENDENT INHIBITION BY CLONES AHIV 1.3,
AHIV 1.6, AND AHIV 2.0 OF
HIV-1 - INDUCED CELL-FUSION

TRANSITION STATE ANALOGS

This application is a continuation of application Ser. No. 08/333,237, filed Nov. 2, 1994 now U.S. Pat. No. 5,952,462 which is a continuation of application Ser. No. 07/190,271, filed May 4, 1988, now abandoned, which was a continuation-in-part of application Ser. No. 06/674,253, filed Nov. 27, 1984, now U.S. Pat. No. 4,888,281 which was a continuation-in-part of application Ser. No. 06/556,016, filed Nov. 29, 1983, now abandoned, the contents of which applications are hereby incorporated by reference into this application.

FIELD OF THE INVENTION

The invention pertains generally to antibodies, antigens, haptens and immunogens capable of eliciting antibodies which include an epitope that binds to and thereby stabilizes a tetrahadral carbon transition state in the cleavage or formation of a peptide linkage or an ester bond so that the cleavage or formation is catalyzed by the antibodies.

Several publications are referenced in this application by Arabic numerals within parentheses. Full citation for these references are found at the end of the specification immediately preceding the claims. The references more fully describe the state-of-the-art to which this invention pertains as well as certain aspects of the invention itself.

BACKGROUND OF THE INVENTION

There are numerous enzymes which have been identified as capable of catalyzing various chemical reactions. Similarly, it has been discovered that antibodies can be elicited to catalyze a variety of chemical reactions (U.S. application Ser. No. 674,253). It is well known that antibodies and enzymes share a fundamental similarity in that both are specialized proteins that bind to other molecules. However, there are important differences between antibodies and enzymes.

Antibodies typically bind to a molecule or antigen so that the antigen is marked as foreign to the organism that produced the antibody. The binding of the antibody to the antigen enables the antigen to be removed from the organism. Enzymes are biological catalysts which bind a molecule in such a way that the activation energy of a reaction involving a molecule or substrate is lowered, thereby increasing the rate of the reaction.

Linus Pauling discovered there are two types of interactions between proteins and the molecules that bind them. Antibodies bind molecules in their ground state while enzymes bind molecules in higher energy states.

Pauling attempted to explain the mechanism of enzyme catalysis based upon such binding. During the course of the chemical reaction, the reactants undergo one or more transitions through intermediate structures or transition states which are energically less favorable than either the reactant or the product. The hydrolysis reaction of a peptide linkage or an ester bond in an aqueous medium passes through a tetrahedral carbon transition state, as depicted in FIGS. 1 (peptide) and 2 (ester). In the transition state, a tetrahedral carbon atom is bonded to: a carbon atom of the acid portion of the peptide linkage or ester bond; two oxygen atoms, one corresponding to the carbonyl group and the other corresponding to a hydroxyl ion or water molecule of the medium; and either the oxygen atom of the alcohol portion of an ester or the nitrogen atom of the amine portion of the peptide linkage. The transition state can be neither isolated nor detected since it exists for only about $10^{-13}$ sec.

In molecular terms, these transition states reflect changes in bond lengths and bond angles as well as bond formations and breakages. The energy required to achieve a transition state is denoted as the activation energy which may also be considered as the difference in energy between the energy of the transition state and the energy of the reactants. According to Pauling's explanation, an enzyme preferentially binds the transition state of a reaction, thereby stabilizing it relative to the substrate and products and reducing the activation energy of the reaction, thus increasing the reaction rate. For example, aspartic proteinases are enzymes which are known to catalyze the hyrolysis of peptide linkages within a protein molecule.

By extending this explanation, Pauling also predicted that stable analogs of a transition state would bind tightly to an enzyme. In a discussion of substrate distortion as one of several possible sources of rate enhancement by enzymes, it has been suggested that the term "transition state analog" might be used to describe an inhibitor of this kind (1a).

The expression of binding energy to compensate for geometrical strain in the substrate is a popular but unlikely mechanism of catalysis. The intermolecular force field cannot overcome the intramolecular force field of the substrate (1).

Compensation of unfavorable solvation changes by the binding energy is also a possible mechanism of catalysis because of the large solvation energies of the polar groups and ions in water. Lone pairs which may act as general bases or nucleophiles will usually be solvated by hydrogen bonding from water or enzyme. Similarly, other reactive groups will usually be "neutralized" by hydrogen bonding or other mechanisms in the initial state of the enzyme. Usually these groups must be "desolvated" before reaction can occur. This process is energetically expensive and yet an essential part of the normal activation energy which may be compensated by favorable interactions between the non-reacting part of the substrate and the enzyme.

The expression of binding energy to compensate for unfavorable electrostatic interactions is another possible mechanism of catalysis. The juxtaposition of like charges could occur in the initial state but be removed in the transition state (2).

Pauling's prediction has become the basis for the now well-established approach to enzyme inhibitor design. The strategy for designing enzyme inhibitors has suggested a strategy for preparing catalytic antibodies whereby antigens are designed based upon mechanistic principles so that antibodies raised in response to such antigens will catalyze a chemical reaction by carrying out the reaction mechanism implicit in the design of the antigen. This strategy has been attempted a number of times.

For example, a transition-state analog mimicking an intramolecular 6-member ring cyclization transition state was used to elicit a monoclonal antibody which acted as a stereospecific, enzyme-like catalyst (3). Specifically, the monoclonal antibody so elicited accelerated, by about a factor of 170, the formation of a single enantiomer of a δ-lactone from the corresponding racemic δ-hydroxyester.

Similarily, monoaryl phosphonate esters, designated as analogs of the transition state in the hydrolysis of carboxylic esters, were synthesized and used as haptens to elicit specific monoclonal antibodies capable of catalyzing the hydrolysis of carboxylic esters (4). Certain of the antibodies elicited were reportedly found to be catalytic and selective for the hydrolysis of particular aryl esters.

Phosphonamidates or phosphonate analog-ligands having conformations that substantially correspond to the conformation of a hydrolytic transition state of an amide or ester ligand and which have been used to produce antibodies are described in U.S. Pat. No. 4,659,567 to Tramontano et al. (Tramontano). Antibodies so produced include a paratope that binds to and stabilizes the tetrahedral carbon atom of the amide or ester hydrolysis transition state of the ligand to hydrolyze the ligand at a predetermined site.

Analog-ligands which can be used to produce antibody catalysts for the hydrolysis of esters and amides are also described in European Patent Application 0,251,093 of Kollmorgen Corp. (Kollmorgen).

However, none of these analog ligands have been designed in accordance with a rational design approach which maximizes stabilization of the transition state and optimizes atomic relationships within the proteolytic transition state analog, thereby enabling the elicitation of antibodies capable of producing the two dramatic effects of enzyme catalysis; these are molecular recognition and rate acceleration.

In enzyme catalysis, groups on both the substrate and the enzyme which are not involved in the chemical mechanism of bond making and breaking, make an important contribution to catalysis. This is illustrated by examining a system where the mechanism is the same for both the enzyme and the non-enzyme catalyzed reaction. For example, the mechanism of action of succinyl-CoA acetoacetate transferase involves nucleophilic attack of the enzyme's glutamate carboxylate on the thioester succinyl CoA, [1] to give an anhydride intermediate (5). The second order rate constant for this reaction is $3 \times 10^{13}$ fold greater than the analogous reaction of acetate with the same ester [2]:

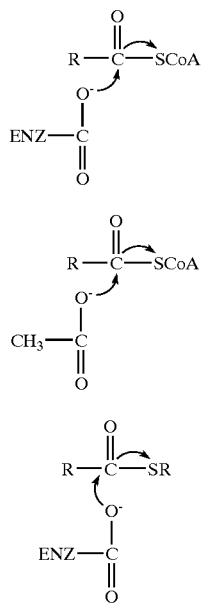

Although the nucleophilicities of the carboxylates may be slightly different because of solvation effects and the enzyme may provide some other forms of catalysis these contributions will not be large. The non-reacting part of the enzyme therefore lowers the activation energy by up to 78 KJmol$^{-1}$. Similarly, changing part of the substrate structure away from the atoms involved in bond making and breaking may also significantly effect catalytic efficiency. The enzyme forms anhydride intermediates from "non-specific" substrates [3]. Even though the chemical reactivities of the two substrates, [1] and [3], are similar, e.g. towards alkaline hydrolysis, the enzyme reaction proceeds up to $3 \times 10^{12}$ fold faster with the so called specific substrate [1](5). The non-reacting part of the substrate—the CoA residue—lowers the activation energy by 72 KJmol$^{-1}$ compared with [3].

Thus, the haptens disclosed in Tramontano do not provide the correct architecture to elicit antibodies that are capable of catalyzing the cleavage of a predetermined peptide sequence in a native protein. These haptens do not provide the correct side-chain groups for production of antibodies that can react with predetermined sites on a protein and cause selective proteolysis in a sequence specific manner. Furthermore, these haptens do not incorporate amino acid side-chain sub-sites on either side of the transition state analog. Without these sub-sites, the haptens cannot provide for the elicitation of catalytic antibodies capable of recognizing a specific amino acid sequence and selectively proteolyzing a peptide linkage within that sequence.

Moreover, the haptens disclosed in Tramontano do not incorporate leaving groups which facilitate and thereby promote proteolytic catalysis. FIG. 3 (6) depicts a representation of the expected free energy diagram for serine proteinase catalysis. In this mechanism, the enzyme provides a nucleophile (Ser-195). A mechanism involving only a single transition-state requires concerted general base/general acid catalysis by the imidazole (His-57) of the catalytic triad in which the hydrogen from Ser-195 is shared between the serine (Ser 195), imidazole (His-57) and a leaving group, an unlikely situation. Given that a discrete TI exists, there must be two transition states along the acylation pathway (as shown in FIGS. 3 and 4).

The stabilization of the carbonyl oxyanion by hydrogen bonds from the protein, the so called "oxyanion hole" in the serine proteinases, is clearly a critical component of the enzyme's catalytic apparatus. The key residue Asn-155 involved in this hydrogen bonding network has been modified by site-directed mutagenesis and results in a decrease of 2–3 orders of magnitude in $K_{cat}$, with little change in $K_m$. Decreases in transition state stabilization of 2.2 to 4.7 Kcal mol$^{-1}$ were observed.

The imidazole of His-57 plays two main roles in the acylation step; first, as a base to facilitate attack by the Ser hydroxyl in formation of the tetrahedral species; and second, as an acid in protonating the leaving group in formation of the acyl-enzyme. As shown in FIG. 5, the TI/imidazole system can exist in four ionization states, including the zwitterionic form [2] in which both the imidazole and the carbonyl oxygen are charged. Only the TI species [2] and [3] can directly give transition states leading to the acyl-enzyme. These transition states differ from one another in that the carbonyl oxygen atom is either protonated [3] or in the oxyanion form [2]. Factors involved in determining the actual reaction pathway include the relative pk's of the amine leaving group nitrogen, the serine oxygen and the carbonyl oxygen.

For example, an unprotonated amine nitrogen will be a much poorer leaving group than the serine in a tetrahedral transition state (compare pk's of approximately 30 for the former against 15 for the latter). Thus the zwitterionic forms of TI and TS should be less stable, but more efficient at expelling the leaving groups than the corresponding neutral forms. Consequently, the zwitterions are expected to be the catalytically relevant forms (7). Electrostatic interactions within the enzyme's active site will contribute significantly to stabilizing the zwitterionic species.

It has been estimated that the pk of the leaving group nitrogen for amide substrates is between 8 and 11 in species such as $Tl_2$ (8). Thus, if the pk of the imidazole remains around 7 in the transition state, then the leaving group has a higher proton affinity than the imidazolium (9). Accordingly, breakdown to the acyl-enzyme would be expected prior to complete formation of the TI. Several lines of evidence, utilizing transition state analog inhibitors, suggest that the true pk of the imidazole in the tetrahedral species is much higher than 7. Although the discussion has centered on the acylation half of the reaction (which is usually the rate-limiting step for amide and peptide substrates) the principles regarding the transition state and tetrahedral intermediate are valid for the deacylation step as well.

Thus, for example, the aromatic compounds described in Tramontano do not lend themselves to provide antibodies that catalyze the hydrolysis of amide bonds in peptides or protein sequences since the pk's of these compounds are significantly more acidic (aniline $pk_a$=4.6; p-methylaniline $pK_a$=5.0) and the transition state stabilization afforded by antibodies raised to these immunogens will not provide for hydrolysis of peptide amide bonds since the actual reaction pathways are different.

Moreover, catalysis occurs through stabilization of the transition state of a reaction. As described below, destabilization of the ground state enzyme/substrate complex relative to the transition state is also necessary for enzymatic catalysis; this prevents accumulation of the enzyme in the enzyme/substrate complex (compare antibody/antigen complex). As noted in Tramontano, it has been suggested that the induced fit mechanism can aid catalysis by providing ground state destabilization relative to the transition state. However, while the induced fit mechanism can increase the value of $K_m$, which reflects the energy of enzyme/substrate complexes, no catalytic advantage is provided for the following reasons.

The requirement for destabilization of the enzyme/substrate ground state is illustrated by the reaction catalyzed by two hypothetical enzymes E in FIG. 6 (10,11). Referring to FIG. 6, curve A shows the energetics for the uncatalyzed reaction of substrate S in solution. Curve B shows the reaction when the enzyme stabilizes the ground state and the transition state (ES and ES↑) to the same extent. The enzymatic ground state, ES, is more stable than free S by the amount $G_B$, and the transition state S by the same amount. For the enzymatic reaction depicted by curve B, the rate limiting step is ES⇌EP, and the energetic barrier for this step is $\Delta G_A$. This is the same barrier as for the reaction of free S. Thus the enzyme depicted in curve B does not catalyze the reaction, even though the transition state is stablized by this enzyme.

Still referring to FIG. 6, curve C shows what the enzyme (or antibody) must do; i.e., the transition state complex (ES) must be stabilized as in curve B but the ground state complex (ES) must also be destabilized relative to that in curve B by the amount $\Delta G_B$. The energetic barrier for the reaction in curve C, $\Delta G_C$, is much less than the barrier for free S (curve A/$\Delta G_A$) or the barrier for the enzyme of curve B (also $\Delta G_A$). The destabilization of the ground state relative to the transition state that is brought about by the enzyme of curve C is necessary for catalysis. This destabilization corresponds to an increase in $K_m$ while the value of $K_{cat}/K_m$ remains constant.

Enzymatic catalysis will be increased by increasing the energy of the ES complex as long as the transition state energy is not also increased; again, this corresponds to an increase in $K_m$ at constant $K_{cat}/K_m$(12,13). The enhanced efficiency from increasing $K_m$ can be explained as an advantage in minimizing the amount of enzyme tied up as ES and thus maximizing the amount of enzyme available for catalysis of the reaction: E+S⇌E+P. The enhancement in the observed rate by increasing $K_m$ at constant $K_{cat}/K_m$ is large when the substrate concentration is near or above $K_m$ because enzyme, which is complexed with substrate when $K_m$ is low, becomes available for catalysis. When the substrate concentration is well below $K_m$ a further increase in $K_m$ at constant $K_{cat}/K_m$ will yield no advantage because essentially all the enzyme is free and already catalyzing the reaction with the apparent second order rate constant $K_{cat}/K_m$.

The fact that the second order rated constant for reacton of free enzyme and free substrate is $K_{cat}/K_m$ can be derived from the Michaelis-Menten equation:

$$v = \frac{K_{cat}[S][E]tot}{[S] + K_m}$$

At low substrate concentration ([S]<<$K_m$), all of the enzyme is free and the Michaelis-Menten equation reduces to v=($K_{cat}/K_m$) [S][E]tot. At high substrate concentration ([S]>>$K_m$), all of the enzyme is in the form ES and the Michaelis-Menten equation reduces to v=$K_{cat}$[E]tot.

Although an increase in $K_m$ at constant $K_{cat}/K_m$ is useful for catalysis, the induced fit mechanism increases $K_m$ but decreases $K_{cat}/K_m$, in fact lessening catalysis (13). The decrease is $K_{cat}/K_m$ for the induced fit enzyme relative to the non-induced fit enzyme arises because some of the energy that is used to stabilize the transition state for the non-induced fit must be used to drive the conformational change of the induced fit enzyme. An equivalent explanation is that the decrease is $K_{cat}/K_m$ arises from a lower concentrtion of the active enzyme conformation in the induced fit mechanism (14).

The mechanism by which antibodies both destabilize the ground state complex and express intrinsic binding energy for the transition state of the particular reaction to be catalyzed has not been completely understood. An induced fit mechanism for antibody-antigen interaction has been proposed for a monoclonal anti-fluorescein-fluorescein hapten system (15). The binding of the antibody to the hapten was found to display a two-step mechanism; formation of an encounter complex followed by a tightening of binding to the hapten in an "induced fit" mechanism allowing for suitable contact interactions between the antibody combining site and the bound fluorescein ligand. If such a mechanism operates in binding of antibodies to their respective antigenic ligands then there exists an analogy between antibody/antigen interactions and enzyme/substrate interactions.

In order for antibodies to function as catalysts, design of the immunogen is crucial for allowing expression of binding energy for the transition state of the reaction. In order for antibodies to destabilize the antibody substrate complex, some form of conformational control of the immunogen is required which will allow for the production of strain and/or distortion of the substrate towards a transition-state trajectory in energetic terms.

Therefore, the immunogens described in Tramontano and Kollmorgen do not incorporate all these necessary features to provide for antibodies having catalytic function because they have not been rationally designed from knowledge of the mechanistic features of enzyme catalysis. Accordingly, they do not provide suitable templates for generating antibody combining sites endowed with catalytic properties.

OBJECTS, FEATURES AND ADVANTAGES OF THE INVENTION

It is an object of the invention to provide a rational design approach for designing haptens according to which haptens are designed based on maximizing stabilization of the hydrolytic transition state, particularly of peptides, and on optimizing atomic relationships within the transition state analog in order to enable the elicitation of antibodies which are capable of molecular recognition and hydrolytic rate enhancement.

It is also an object of the invention to provide haptens which include an array of atoms which mimics the transition state in the cleavage or formation of a peptide linkage or an ester bond in a molecule.

It is a further object of the invention to provide haptens which mimic the native conformation of biomolecules and which have complimentarity with biomolecules.

It is another object of the invention to provide catalytic antibodies which are capable of catalyzing the cleavage or formation of a peptide linkage or an ester bond in a molecule.

It is yet another object of the invention to provide catalytic antibodies capable of recognizing a specific amino acid sequence in a molecule containing numerous amino acids.

It is a further object of the invention to provide catalytic antibodies which are capable of catalyzing the cleavage or formation of a specific peptide linkage or ester bond within a specific amino acid sequence of a molecule.

It is yet another object of the invention to provide a method for catalyzing the cleavage or formation of a peptide linkage or an ester bond in a molecule.

It is a further object of the invention to provide a method for catalyzing the cleavage or formation of a specific peptide linkage or ester bond within a specific amino acid sequence of a molecule containing numerous amino acids joined by peptide linkages.

These and other features and advantages of the invention will become readily apparent from the ensuing detailed description, and the novel features will be particularly pointed out in the appended claims.

SUMMARY OF THE INVENTION

The invention is broadly directed to antigens capable of eliciting through immunogenic methods catalytic antibodies which can catalyze the cleavage or formation of a peptide linkage or an ester bond in a molecule. The invention is directed to antigens capable of eliciting through immunogenic methods catalytic antibodies which can catalyze the selective cleavage or formation of a predetermined peptide linkage or an ester bond in a native polypeptide sequence. In general, the antigens may be a hapten or an immunogen comprising a hapten and a suitable carrier molecule. The haptens include structural elements which are designed to mimic structurally the transition state of the cleavage or formation of a peptide or an ester bond linkage.

The haptens according to the invention provide the correct side-chain groups for production of antibodies that can react with predetermined sites on a protein and can catalyze selective proteolysis in a sequence specific manner. The haptens further incorporate amino acid side-chain sub-sites on either side of the tetrahedral transition state analog. These sub-sites provide for the elicitation of catalytic antibodies capable of recognizing a specific amino acid sequence and selectively proteolyzing a peptide linkage within that sequence.

Such catalytic antibodies are elicited with the haptens of the present invention. For example, a hapten according to the invention, shown below,

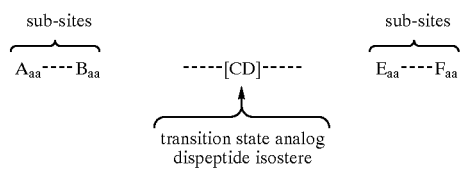

incorporates not only the transition state analog dipeptide isostere [CD] but also sub-site amino acid residues A, B, E, F. The optimum number of sub-site residues is determined by the size of the antibody combining site. It is likely that the only essential criterion for effective binding of antibody to a peptide is that complementarity between the antigen-combining site of the antibody and the molecular surface of the binding peptide is maintained with regard to both shape and charge.

As noted earlier, in order for antibodies to function as catalysts, design of the immunogen is crucial for allowing expression of binding energy for the transition-state of the reaction. In order for antibodies to destabilize the antibody:substrate complex, some form of conformational control of the immunogen is required. This control allows for the production of strain and/or distortion of the substrate towards a transition-state trajectory in energetic terms.

The haptens according to the invention are designed in such a way that the hybridization of the atom corresponding to the carbonyl carbon of the scissile bond of the peptide bond is converted from $sp^2$ to $sp^3$ hybridization. This conversion constitutes a major step in achieving conformational control. This in itself allows the subsite residues to occupy geometries that approximate those present in the tetrahedral transition state of the reaction. For example, it is well known in the catalysis of hydrolysis of peptides by the aspartic proteinase pepsin that addition of extra subsites on either side of the hydrolyzed peptide bond leads to an increase in the catalytic efficiency of the enzyme by increasing $K_{cat}$ by up to 3–4 orders of magnitude without effecting the dissociation constants of the initial enzyme-substrate complex (16).

It follows that antibody binding peptides deduced without recourse to sequence information should be defined as "mimotopes", or mimics of the epitope which induce the antibody, rather than assuming that they are an accurate reproduction of that epitope (17). In this regard, peptide sequences containing transition state analog dipeptide isosteres, according to the invention, at the bond that is required to be hydrolyzed by the catalytic antibodies of the present invention define a sequence that the catalytic antibody will hydrolyze in a native protein. The binding energy of the antibody is distributed in such a way as to allow both sequence specific recognition and chemical reactivity with the native protein or peptide of interest.

It has been reported that it is not necessary to prepare peptides longer than eight amino-acid residues (octapeptides) to demonstrate all continuous epitopes (18). It has also been demonstrated that antibodies bind to dipeptides in a reproducible manner (19). It has also been established that optical isomerism of the amino acids used has a powerful influence on the strength and specificity of antibody binding by dipeptides. Consequently, the importance of L and D amino acid residues in the immunizing antigen will have a profound effect on the chirality of the antibody combining site generated.

In generating catalytic antibodies according to the invention with predetermined specificity for particular sequential (continuous) or assembled epitopes in a native protein, the relationship between measurable properties of a protein and its immunogenic sites are important (20). With the ready availability of protein sequences, the most widely used algorithm is based on the likelihood of finding a sequential epitope at the site of a local maximum in the hydrophilicity profile (21). Surface accessibility profiles (22) and protein flexibility (23) as providing information on the antigen sites in a native protein sequence. With knowledge of these sites and the importance of these epitopes in receptor mediated interactions or other disease associated mechanisms, peptide haptens having transition state analog isosteres within these important "bioactive" epitopes can be designed in accordance with the invention. The catalytic antibodies elicited with these haptens can then be utilized, for example, to digest epitopes on viral proteins or tumor derived growth factors or other peptides involved in life-threatening situations (e.g., tumor necrosis factor in bacterial sepsis, etc.).

Thus, the haptens of the invention are distinguished from prior analog-ligands in that they have been rationally designed from knowledge of mechanistic features of enzyme catalysis and provide suitable templates for generating antibody combining sites endowed with catalytic properties. Consequently, they incorporate all the necessary features to provide for antibodies capable of molecular recognition and catalytic function.

Accordingly, the invention is directed to haptens of formula I

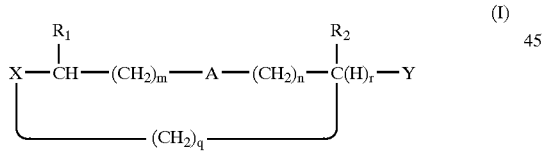

wherein $R_1$ and $R_2$ may be the same or different and each is a side chain of a naturally occurring amino acid, a hydroxy containing side chain of a naturally occurring amino acid wherein said hydroxy group may be glycosylated, phosphorylated, sulphonylated or protected by a hydroxy protecting group, a primary amido containing side chain of a naturally occurring amino acid wherein said amido group may be glycosylated, or $(C_1-C_4)$ alkyl, $-CH_2CH(CO_2H)_2$, $-(CH_2)_2S(O)CH_3$ $-(CH_2)_2S(O)_2CH_3$ $-(CH_2)_3NH_2$ or $-(CH_2)_3ONHC$ $(=NH)NH_2$;

m, n and q may be the same or different and each is 0 or an integer from 1 to 10 and r is 0 or 1 provided that if r is 1, then there is no bond between X and the carbon bonded to $R_2$;

A is

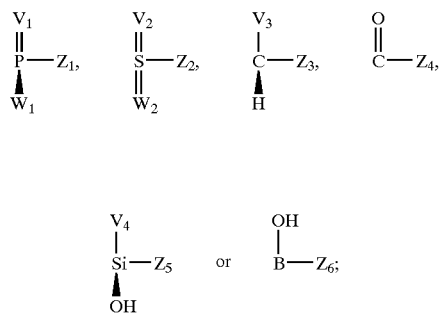

$V_1$ is O or S;
$V_2$ is O or a lone pair of electrons;
$V_3$ and $V_4$ are OH or $NH_2$;
$W_1$ is OH, $NH_2$, SH or H;
$W_2$ is O or a lone pair of electrons;
X is hydrogen, oxygen, amino, amino protected by a protecting group selected from the group consisting of terminal amino protecting groups, amino bonded to the C terminus of a naturally occurring amino acid to form a peptide bond, amino bonded to the C terminus of a peptide to form a peptide bond, said amino acid and peptide being unprotected or protected by said protecting group, or X is alkene, $(C_1-C_9)$alkyl, $(C_1-C_9)$ alkoxy, phenyl, phenoxy, cyclohexyl, phenylthio, phenylsulfinyl or phenylsulfonyl wherein the aforementioned phenyl groups may be unsubstituted or mono-, di- or trisubstituted by halogen, $(C_1-C_4)$alkyl, $(C_1-C_4)$alkoxy or $(C_1-C_4)$alkoxycarbonyl;

Y is hydrogen, carboxyl, carboxyl protected by a protecting group selected from the group consisting of terminal carboxyl protecting groups, a carbonyl bonded to the N terminus of a naturally occurring amino acid to form a peptide bond, carbonyl bonded to the N terminus of a peptide to form a peptide bond, said amino acid and peptide being protected or unprotected by said protecting group, or Y is $(C_1-C_9)$alkyl, $(C_1-C_9)$alkoxy, phenyl, phenoxy, cyclohexyl, phenylthio, phenylsulfinyl or phenylsulfonyl wherein the aforementioned phenyl groups may be unsubstituted or mono-, di- or trisubstituted by halogen, $(C_1-C_4)$alkyl, $(C_1-C_4)$alkoxy or $(C_1-C_4)$alkoxycarbonyl; and wherein each of said substituents $R_1$, $R_2$, X and Y may be unbound or bound to one or more of said remaining substituents $R_1$, $R_2$, X and Y and if bound, then by a covalent bond or a linker moiety selected from the group consisting of $-(CH_2)_s-S-S-(CH_2)_t-$, $-(CH_2)_t-$, $-S-(CH_2)_t-S-$, $-(CH_2)_s-S-(CH_2)_t-$, $-(CH_2)_s-CH=CH-(CH_2)_t-$, $(CH_2)_s-NH-CO-(CH_2)_t-$, $-(CH_2)_s-NH-(CH_2)_t-$ and $-(CH_2)_s-Ø-(CH_2)_t-$;

$Z_1$, $Z_2$, $Z_3$, $Z_4$, $Z_5$ and $Z_6$ may be unbound or bound to said linker moiety; and if unbound $Z_1$ is O, NH, $CH_2$ or S, $Z_2$ is O, NH or $CH_2$, $Z_3$ is $CH_2$, $Z_4$ is $CF_2$ or $CF_2CO$ and $Z_5$ and $Z_6$ are O or $CH_2$ provided that if $Z_1$ is O or NH and if $V_1$ is O and if $W_1$ is OH, then r is either 0 or r is 1 and at least one of said substituents $R_1$, $R_2$, X or Y is bound to one or more of said remaining substituents $R_1$, $R_2$, X and Y, and further provided that if $Z_3$ is $CH_2$ and $V_3$ is OH, then r is either 0 or r is 1 and at least one of said substituents $R_1$, $R_2$, X or Y is bound to one or more of said remaining substituents $R_1$, $R_2$, X and Y; and if bound Z and Z are N or CH, $Z_4$ is CF or CFCO and $Z_3$, $Z_5$ and $Z_6$ are CH and further provided that if $Z_1$, $Z_2$, $Z_3$, $Z_4$, $Z_5$ or $Z_6$ is bound to said linker moiety, it is covalently bound to said linker moiety by substitution at an appropriate atom of said linker moiety; and s and t may be the same or different and each is 0 or an integer from 1 to 10 unless the linker moiety is —$(CH_2)_t$— in which case t is an integer from 1 to 10.

The invention is also directed to boron-containing haptens having formula II

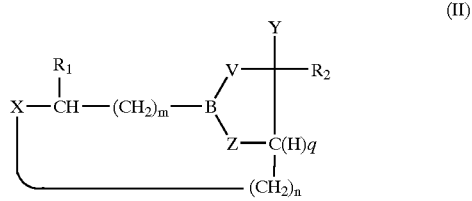

(II)

wherein $R_1$, $R_2$, X, Y and m are defined as before;

V is O, $CH_2$ or NH;

Z is O, $CH_2$ or NH;

n is 0 or 1; and q is 1 or 2 provided that if q is 2, then there is no bond between X and the carbon bonded to Z.

The invention is further directed to phorphorus containing haptens of formula III

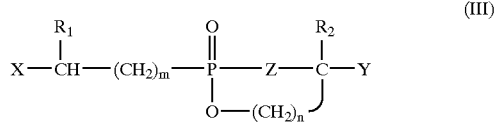

(III)

wherein $R_1$, $R_2$, X, Y and m are defined as before;

Z is O or NH; and n is 0 or an integer from 1 to 10.

The foregoing haptens may be used as antigens for in vitro elicitation of catalytic antibodies. However, for purposes of in vitro elicitation, the haptens must be complexed to a suitable carrier molecule in order to obtain an immunogen suitable for immunization. Therefore, the invention is also directed to immunogens capable of eliciting catalytic antibodies. Such immunogens comprise a hapten as hereinbefore described and a suitable carrier molecule.

In another aspect the invention is directed to catalytic antibodies which are elicited by antigens comprising the haptens of the invention as described above. Similarily, the invention is also directed to catalytic antibodies which can catalyze a chemical reaction of interest and which are elicited through in vitro or in vivo techniques by antigens comprising haptens according to the invention as described above, wherein the antibodies have been prepared by exposing cells capable of producing antibodies to the antigens and thereby generating antibody producing cells; hybridizing the antibody producing cells with myeloma cells and thereby producing a plurality of hybridoma cells each producing monoclonal antibodies; and screening the plurality of monoclonal antibodies to identify a monoclonal antibody which catalyzes the chemical reaction of interest.

In still another aspect, the invention is directed to a method for producing catalytic antibodies which can catalyze a chemical reaction of interest and which are elicited through in vitro or in vivo techniques by antigens comprising the haptens according to the invention as described above. The method comprises exposing cells capable of producing antibodies to the antigens and thereby generating antibody producing cells; hybridizing the antibody producing cells with myeloma cells and thereby generating a plurality of hybridoma cells each producing monoconal antibodies; and screening the plurality of monoclonal antibodies to identify a monoclonal antibody which catalyzes the chemical reaction of interest.

The invention is also directed to a method for catalyzing the cleavage or formation of a peptide linkage or an ester bond in a molecule. The method comprises contacting the molecule with an effective amount of a catalytic antibody which has been elicited by antigens comprising haptens according to the invention.

In another aspect, the invention is directed to a method for catalyzing the cleavage or formation of a specific peptide linkage or ester bond within a specific amino acid sequence of a molecule containing numerous amino acids joined by peptide linkages. The method comprises contacting the molecule with an effective amount of a catalytic antibody which has been elicited by antigens comprising haptens according to the invention. The haptens have complimentarily with the specific amino acid sequence.

As noted earlier, the catalytic antibodies elicited by antigens comprising haptens according to the invention can be used, for example, to digest epitopes on viral proteins or tumor-derived growth factors on other peptides involved in health- or life-threatening situations.

Thus, in another aspect, the invention is directed to a method for treating acquired immune deficiency syndrome (AIDS) by inhibiting human immunodeficiency virus (HIV). The method comprises treating a patient with an effective amount of a catalytic antibody elicited using a hapten of the invention.

The invention is also directed to a method for treating hypertension by inhibiting human renin activity. The method comprises treating a patient with an effective amount of a catalytic antibody elicited using a hapten of the invention.

BRIEF DESCRIPTION OF THE DRAWINGS

The invention, as well as other objects, features and advantages thereof will be understood more clearly and fully from the following detailed description, when read with reference to the accompanying drawings, in which.

DETAILED DESCRIPTION OF THE INVENTION

Broadly, the invention relates to antigens which are capable of eliciting through immunogenic methods antibodies which can catalyze the cleavage or formation of a peptide linkage or the cleavage or formation of an ester in a molecule. These antigens comprise a hapten or a hapten and a suitable carrier molecule. Because the antibodies so elicited can catalyze a chemical reaction, they are defined as "catalytic antibodies." Catalytic antibodies are identified and described in Schochetman and Massey, application Ser. No. 674,253 filed Nov. 27, 1984, referred to above in the "Statement of the Invention."

During the course of a chemical reaction, the reactants undergo one or more transitions through structures which are energetically less favorable than either the reactant or product. In molecular terms, these transition states (or intermediate structures) reflect changes in bond lengths and bond angles as well as bond formations and breakages. The energy required to achieve a transition state is denoted as the activation energy, which may also be considered as the difference in energy between the energy of the transition state and the energy of the reactants.

Catalysts increase chemical reaction rates by lowering the activation energy of a reaction. Antibodies elicited to a hapten or immunogen, which antigens are chosen because, inter alia, they resemble the presumed transition state structure (i.e., a transition state analog), can catalyze reactions. The antibody thus produced should stabilize the energy of the transition state relative to reactants and products. This approach has been successfully demonstrated in the generation of several catalytic monoclonal antibodies.

Catalytic antibodies can catalyze reactions because the free energy of binding, $\Delta G_{bind}$ of an antibody is at least equal to the catalytic free energy $\Delta G_{catatlysis}$ for the reaction to be carried out. For a proteolytic reaction, e.g., hydrolysis of a peptide, it has been reported that phosphonamidate peptide analogs binding to zinc endopeptidase thermolysis show a strong correlation between their free energies of interaction with the enzyme, reflected in the inhibition constant $K_i$, and the (hypothetical) binding energies of the transition states for hydrolysis of the corresponding amide substrates, reflected in the second order rate constants for enzymatic turnover ($K_{cat}/K_m$) (24). From this correlation it has been concluded that the phosphonamidates mimic the transition state configurations of the enzyme-substrate complexes (25). It has also recently been shown that the intrinsic binding energy from a hydrogen bonding group in an enzyme inhibitor can be evaluated experimentally and also calculated by means of a thermodynamic perturbation method implemented with molecular dynamics (26, 27).

Figure 1:
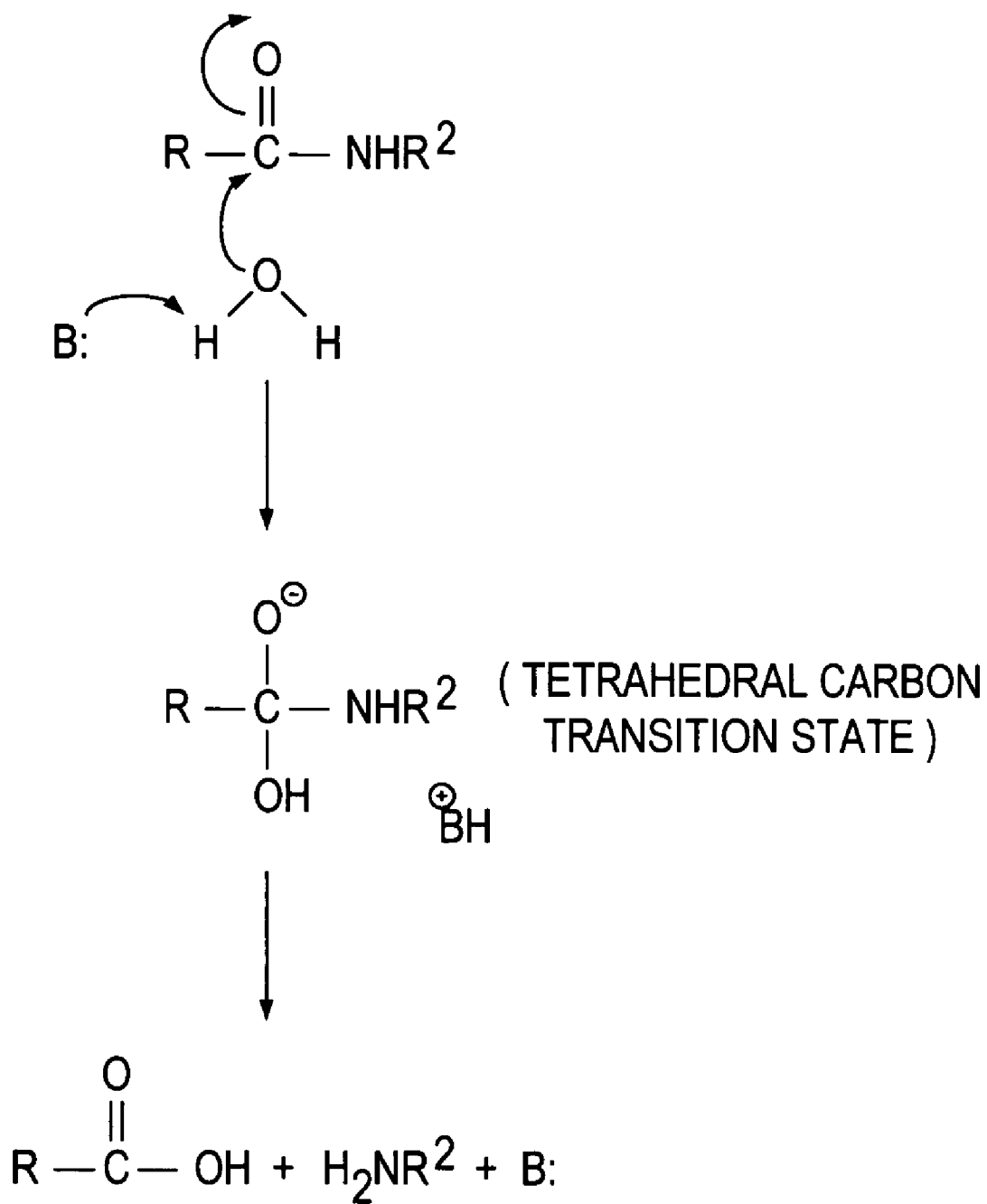
FIG. 1 shows the tetrahedral carbon transition state in the hydrolysis of a peptide bond.
Figure 2:
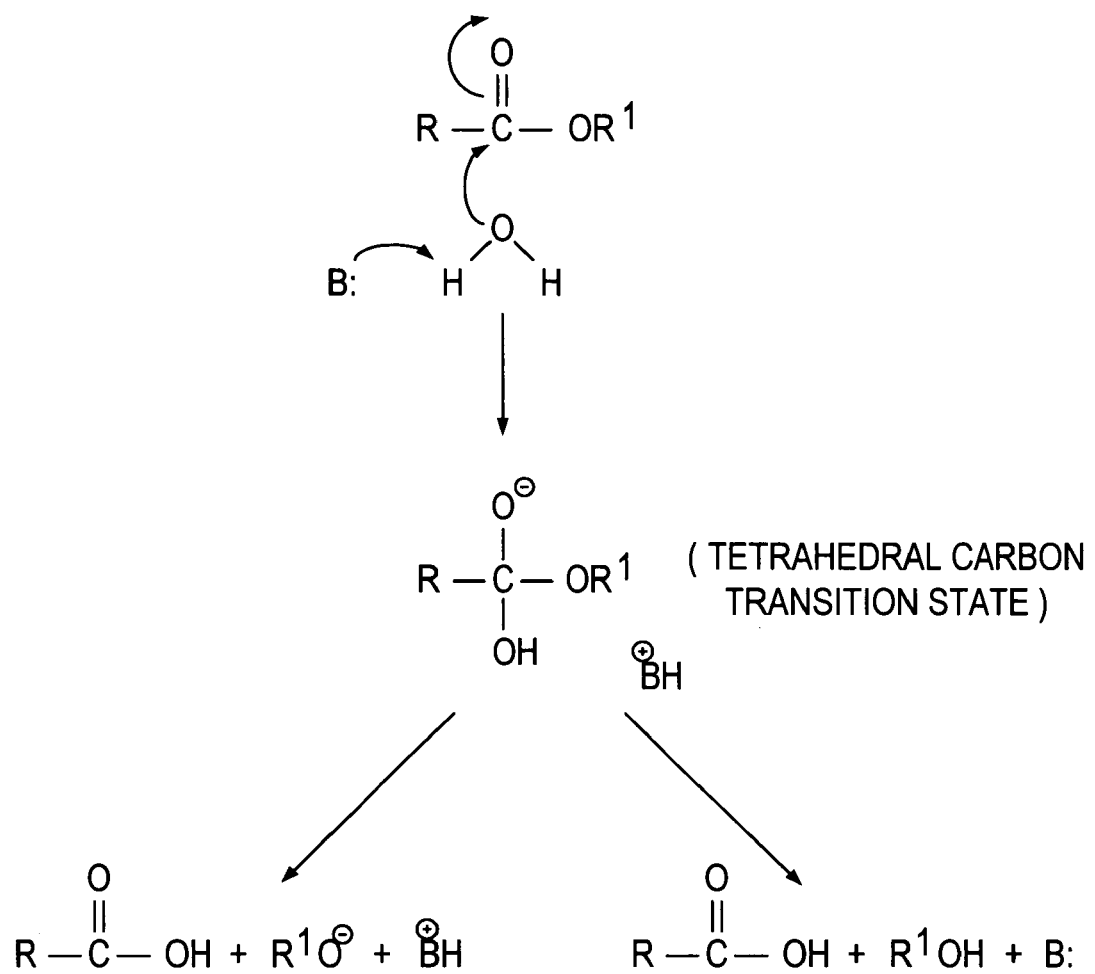
FIG. 2 shows the tetrahedral carbon transition state in the hydrolysis of an ester bond.
Figure 3:
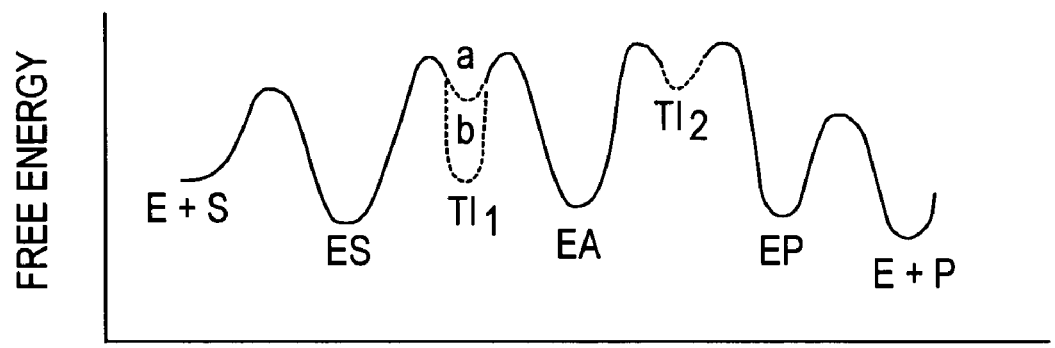
FIG. 3 shows a representation of the expected free energy diagram for serine proteinase catalysis.
Figure 4:
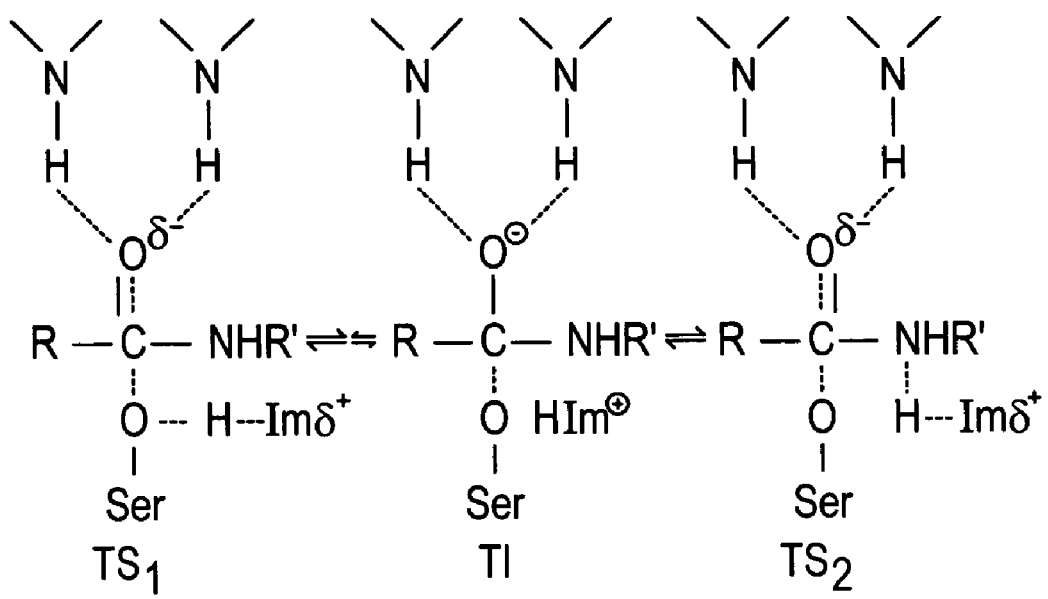
FIG. 4 shows the transition states (TS) and tetrahedral intermediate (TI) in the acylation of an amide substrate.
Figure 5:
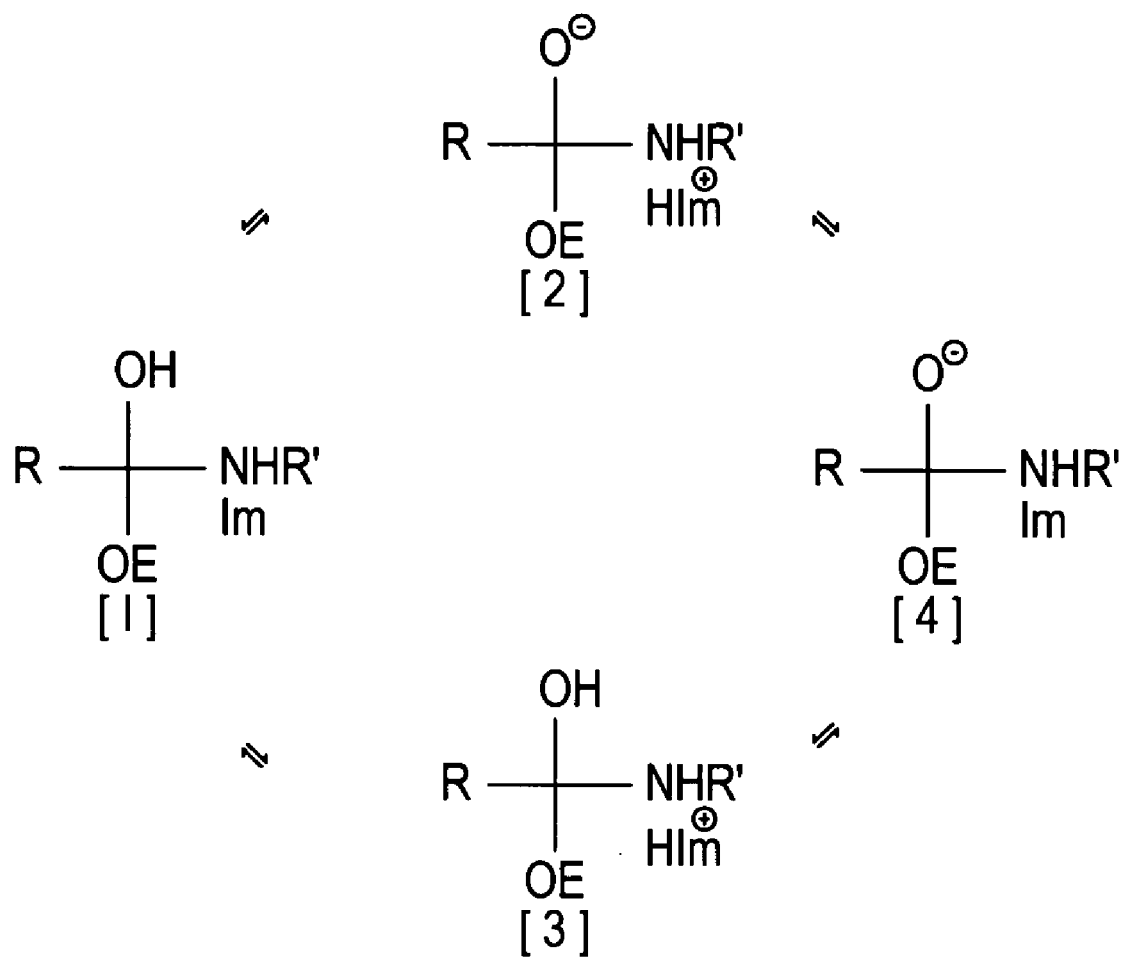
FIG. 5 shows tautomers of the tetrahedral intermediate/imidazole system of an amide substrate.
Figure 6:
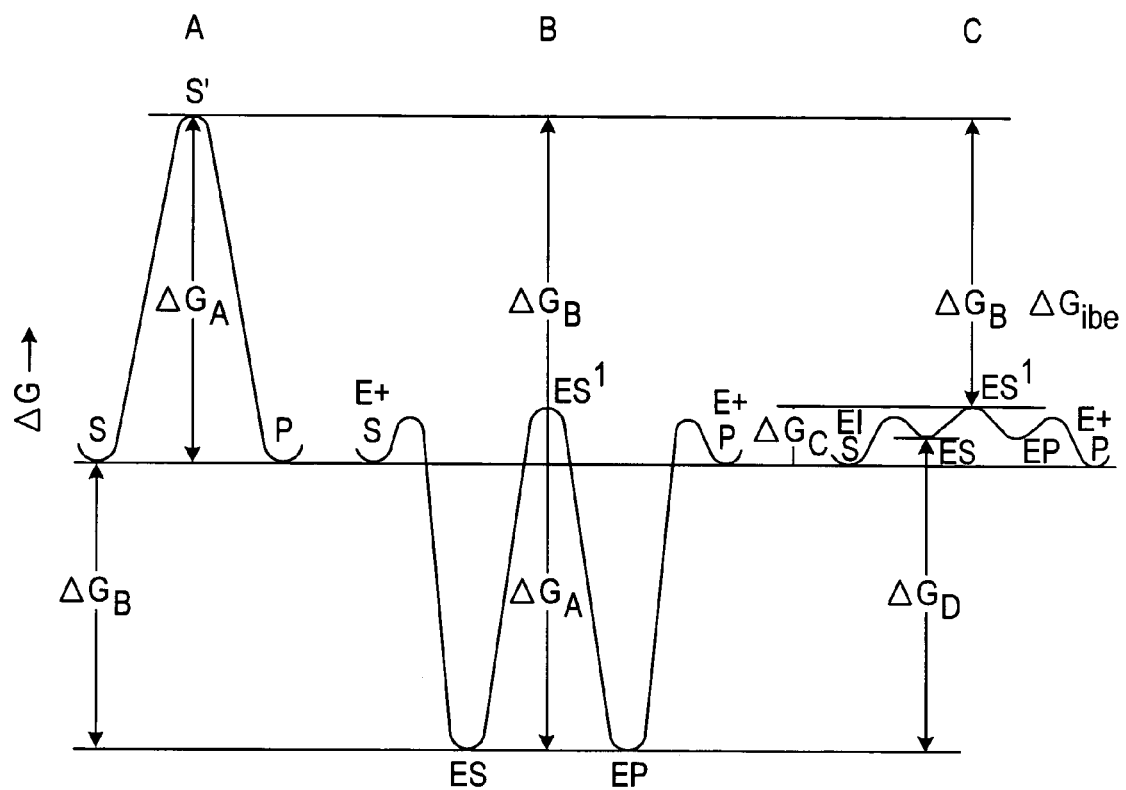
FIG. 6 is a comparison of the free-energy profiles for the nonenzymatic reaction of substrate S.
Figure 7:
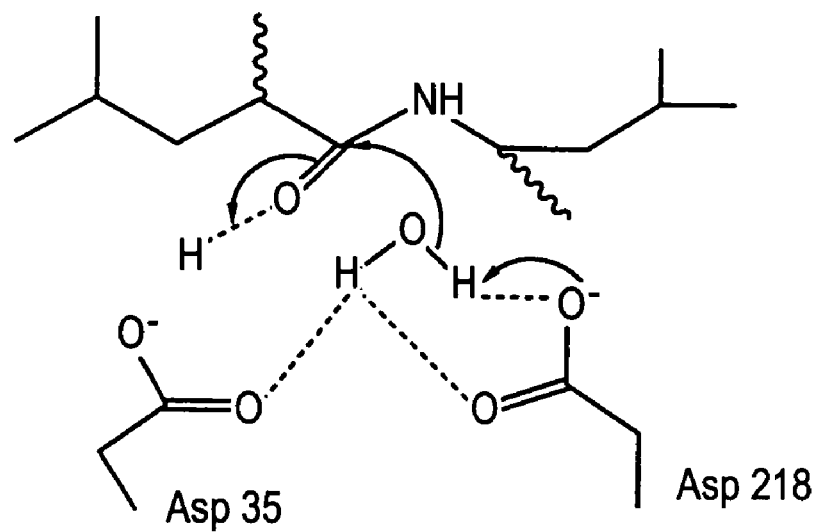
FIG. 7 shows the mechanism of the aspartic proteinases in catalyzing hydrolysis of peptide linkages.
Figure 7:
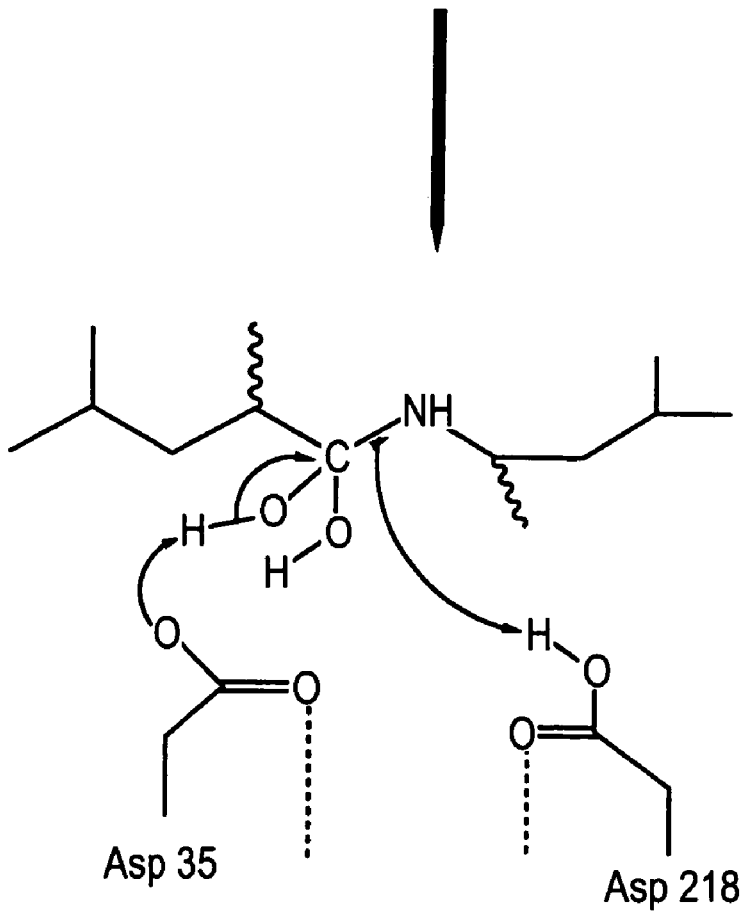

Therefore, in one aspect, the haptens according to the invention are designed to elicit antibodies that can induce cleavage of the substrate molecule either by a solvent, an added nucleophile or an amino acid residue in the combining site. These haptens are used to elicit antibodies having paratopes that can chemically modify epitopes to which they bind. The term "paratope" as used herein means the part of an antibody which makes contact with the antigenic determinant (epitope). The term "epitope" as used herein means a single antigenic determinant which, functionally, is the portion of an antigen which combines with the antibody paratope. Each antibody paratope can induce modification of multiple epitopes, i.e., the paratope acts as a catalyst in much the same way as an enzyme exerts its catalytic activity on a substrate. For example, in the hydrolysis of peptide bonds by aspartic proteinases, a water molecule at the active site of the enzyme acts as the nucleophile in a desolvated active site. An active site "flap" region of the enzyme (residue 73-80 in penicillopepsin) closes over the substrate in the activated transition state complex. The mechanism of the aspartic proteinases in catalyzing hydrolysis of peptide linkages is shown in FIG. 7.

The geometry of the catalytically relevant aspartic acids is essential for catalysis to proceed. Since antibodies having paratopes that bind to epitopes may not fortuitously contain, like the aspartic proteinases, the required amino acid side chains for catalysis, the hapten may need to contain additional structures to provide for the lack of incipient catalytic amino acid side chains.

Figure 8:
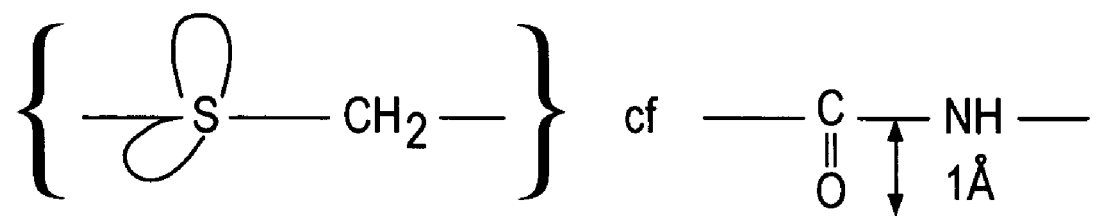
FIG. 8 depicts a sulfur containing isostere showing conversion from $sp^2$ hybridization to $sp^3$ hybridization.

For example, replacement of the carbonyl group of the scissile amide bond in the peptide chain with a sulfur atom (causing conversion from $sp^2$ hybridization to $sp^3$ hybridization) together with replacement of the amide nitrogen (—NH—) by a methylene group (—$CH_2$—) provides a structural isostere as shown in FIG. 8. Such an isostere is described by the hapten of formula I described above. The remaining lone-pairs on the sulfur atom provide potential hydrogen-binding sites within the antibody combining site and provide for the positioning of a serine or carboxylic acid group proximal to the scissile peptide bond.

Catalytic antibodies elicited with haptens according to the invention are "site specific" in that they are deliberately designed only to catalyze cleavage of peptide linkages having certain structural conformations at specific sites in a protein molecule. Likewise, these catalytic antibodies are designed only to catalyze the formation of peptide linkages from the N- and C-termini of amino acids having certain structural conformations at those terminals. Therefore, haptens according to the invention may be used to elicit a site specific catalytic antibody capable of cleaving peptide linkages at specific sites in a protein molecule to produce two or more cleaved protein strands. The same catalytic antibody can then catalyze the formation of peptide linkages wherein those cleaved strands having the right structural conformation are joined.

Thus, the haptens of the invention, are designed to mimic the transition-states for a variety of chemical reactions. Preferably, the reactions are the cleavage or formation of a peptide linkage or an ester bond.

In its broadest sense, the term "antigen" is defined as a molecule which induces the formation of an antibody. As used herein, the term "antigen" means a hapten according to the invention or an immunogen which comprises a hapten according to the invention complexed to a suitable carrier molecule. Carrier molecules include, for example, keyhole limpet hemocyanin, thyroglobulin, chicken immunoglobulin, ovalbumin, bovine serum albumin, T-helper peptides, etc.

The term "transition state analog" as used herein refers to an array of atoms which is designed to approximate or "mimic" the configuration of an amide bond or an ester bond as such bonds exist in a hydrolytic transition state. As an illustrative example, the substituent "A" in formula I above represents a number of such arrays.

The term "transition state analog dipeptide isostere" as used herein refers to a structure which comprises a transition state analog having side chains of two amino acids, one side chain on each side of the transition state analog. In other words, a transition state analog dipeptide isostere is a dipeptide in which the normal amide bond (i.e., —CO—NH—) between the two amino acids has been replaced by an array of atoms as defined above. Additional amino acid residues may be incorporated on either side of the isostere to form a polypeptide. Thus, the transition state analog replaces the bond "targeted" for cleavage in the substrate molecule.

The term "hapten" as used herein is defined as a molecule which can act as an epitope. Haptens according to the invention incorporate a transition state analog according to the invention.

The term "naturally occurring amino acid" as used herein includes the twenty essential amino acids and other amino acids which may or may not be found in proteins. These amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, 4-hydroxyproline, 5-hydroxylysine, epsilon-N-methyllysine, 3-methylhistidine, beta-alanine, gamma-aminobutyric acid, homocysteine, homoserine, citrulline, ornithine, canavanine, djenkolic acid and beta-cyanoalanine. An amino acid consists of a tetrahedral carbon atom to which is bonded an amino group, a carboxyl group, a hydrogen atom and a distinctive group referred to as a "side chain".

Accordingly, the substituents $R_1$ and $R_2$ of the above-described haptens may be the same or different and each is a side chain of a naturally occurring amino acid, a hydroxy containing side chain of a naturally occurring amino acid wherein said hydroxy group may be glycosylated, phosphorylated, sulphonylated or protected by a hydroxy protecting group, a primary amido containing side chain of a naturally occurring amino acid wherein said amido group may be glycosylated or $(C_1-C_4)$alkyl, —$CH_2CH(CO_2H)_2$, —$(CH_2)_2S(O)CH_3$, —$(CH_2)_2S(O)_2CH_3$, —$(CH_2)_3NH_2$, or —$(CH_3)_2ONHC(=NH)NH_2$. Preferably, $R_1$ and $R_2$ are hydrogen, methyl, —$CH_2CH_3$, —$CH_2CH(CH_3)_2$, —$CH(CH_3)CH_2CH_3$, —$(CH_2)_3CH_3$, —$CH(CH_3)_2$—$CH_2CN$, —$CH_2SH$, —$(CH_2)_2SH$, —$CH_2OH$, —$CH(OH)CH_3$, —$(CH_2)_2OH$, —$(CH_2)_3NHC(=NH)NH_2$, —$(CH_2)_3NHC(O)NH_2$, —$(CH_2)_2ONHC(=NH)NH_2$, —$(CH_2)_3ONHC(=NH)NH_2$, —$CH_2C(O)NH_2$, —$(CH_2)_2C(O)NH_2$, —$CH_2CO_2H$, —$(CH_2)_2CO_2H$, —$CH_2CH(CO_2H)_2$, -5-methylene imidazole, -5-methylene, 3-N-methyl imidazole, —$(CH_2)_4NH_2$, —$(CH_2)_4NHCH_3$, —$(CH_2)_3NH_2$, —$(CH_2)_2CH(OH)CH_2NH_2$, —$(CH_2)_2SCH_3$, —$(CH_2)_2S(O)CH_3$, —$(CH_2)_2S(O)_2CH_3$, benzyl, para-hydroxylbenzyl, -3-methylene indole, -2-pyrrolidino, -2-,4-hydroxylpyrrolidino and -2-,3-hydroxylpyrrolidino.

Those side chains containing a hydroxy group may be further glycosylated to form a glycoside. For example, it is well known that aldopyranoses readily react with alcohols in the presence of a mineral acid to form anomeric α- and β-glycosides. The glycosides are asymetric mixed acetals formed by the reaction of the anomeric carbon atom of the intramolecular hemiacetal or pyranose form of the aldohexose with a hydroxyl group furnished by an alcohol. This is called a glycosidic bond. For example, D-glucose when reacted with methanol forms methyl-α-D-glucopyranoside and methyl-β-D-glucopyranoside. Thus, the hydroxy group of any of the side chains may react with an intramolecular hemiactal or pyranose to form a glycoside. Similarly, side chains containing a primary amide may be glycosylated. The hydroxy group of these side chains may also be phosphorylated or sulphonylated. As an illustrative example, the side chain of serine, if phosphorylated would be

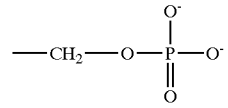

and if sulphonylated would be

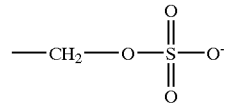

In addition, the hydroxy group of any of the side chains may be protected by any number of suitable hydroxy protecting groups well known in the art. These would include, for example, a tertiary butyl group.

The term "terminal amino protecting group" means any group capable of protecting the terminal amino moiety of a peptide or amino acid. "Peptide" as used herein includes dipeptides and polypeptides. Therefore, terminal amino protecting groups include acetyl, succinyl, benzoyl, t-butyloxycarbonyl, carbobenzoyl, tosyl, dansyl, isovaleryl, phthalyl, 1-adamantanesulphonyl, acetimido, benzimido, amidino, carbamyl and the functional equivalents thereof.

The term "terminal carboxyl protecting group" means any group capable of protecting the terminal carboxyl moiety of a peptide or amino acid. Terminal carboxyl protecting groups include $(C_1-C_9)$alkyl, phenyl, substituted methyl esters such as methoxymethyl and phenacyl esters, 2-substituted ethyl esters such as cyclohexyl and allyl, substituted benzyl esters such as para-methoxybenzyl and para-bromobenzyl, amides such as piperidinyl and hydrazide and functional equivalents thereof.

Haptens according to the invention contain one or more asymmetric carbon atoms and/or contain an asymmetric phosphorus atom and therefore exist in enantiomeric or diastereomeric forms. In general, the corresponding haptens according to the invention are obtained in the form of racemates or mixtures of diastereomers. If desired, techniques well known in the art for the separation of the mixtures into sterically homogeneous constituents may be used. Preparation of the optical isomers in a pure state is also possible by using sterically homogeneous starting materials.

As indicated in formula I above, the various tetrahedral arrays of atoms designated generically by the letter "A" include a central atom which may be phosphorus, sulphur, carbon, carbonyl, silicon and boron. One of ordinary skill in the art will realize that arrays containing carbonyl and boron central atoms will assume a tehrahedral like configuration upon reaction with water in an aqueous environment.

Preferred haptens of formula I containing a central phosphorus atom include the following cyclic structure

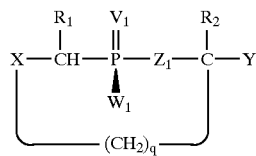

wherein $R_1$, $R_2$, X, Y, $W_1$, $V_1$, $Z_1$ and q are defined as above. Especially preferred are those in which $V_1$ is O, $W_1$ is OH, SH or H, $Z_1$ is O, NH or $CH_2$ and q is 0 or 1.

Preferred haptens of formula I containing a central sulphur atom include compounds in which $Z_2$ is NH. Such a hapten is aminomethanesulfonamidylalanyl acid. Other preferred haptens of formula I containing a central sulfur atom include the following cyclic structure

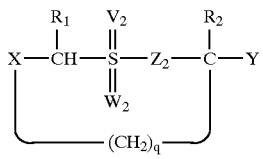

wherein $R_1$, $R_2$, X, Y, $V_2$, $W_2$, $Z_2$ and q are defined as above. Especially preferred are those in which $V_2$ and $W_2$ are O or a lone pair of electrons, $Z_2$ is O, $CH_2$ or NH and q is 0 or 1.

Preferred haptens of formula I containing a central carbon a tom include compounds in which $V_3$ is OH and $Z_3$ is $CH_2$ $V_3$ is $NH_2$ and $Z_3$ is $CH_2$. Other preferred haptens of formula I containing a central carbon atom include the following cyclic structure

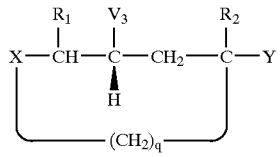

wherein $R_1$, $R_2$, X, Y, $V_3$ and q are defined as above. Especially preferred are those wherein $V_3$ is OH or $NH_2$ and q is 0 or 1.

Preferred haptens of formula I containing a central carbonyl include the compound in which $Z_4$ is $CF_2$. Such a preferred hapten is 5-(serinyl)amino 3,3-difluoro 4-oxo 6-hydroxy heptanoic acid. Other preferred haptens of formula I containing a central carbonyl include the following cyclic structure

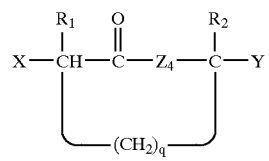

wherein $R_1$, $R_2$, X, Y, $Z_4$ and q are defined as above. Especially preferred are those in which $Z_4$ is $CF_2$ and q is 0 or 1.

Preferred haptens of formula I containing a central silicon atom include compounds in which $V_4$ is OH and $Z_5$ is O, and $V_4$ is OH and $Z_5$ is $CH_2$. A preferred hapten is 3-(aminomethyldihydroxysilyl) propionic acid. Other preferred haptens of formula I containing a central silicon atom include the following cyclic structure

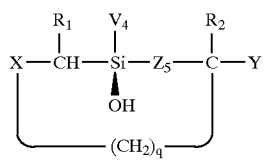

wherein $R_1$, $R_2$, X, Y, $Z_5$ and q are defined as above. Especially preferred are those in which $V_4$ is OH, $Z_5$ is $CH_2$ and q is 0 or 1.

Preferred haptens of formula I containing a central boron atom include compounds wherein $Z_6$ is O. Such a preferred hapten is (S)-lactate-1-(R)-amino-2-phenylethane boronate.

Other preferred haptens of formula I include

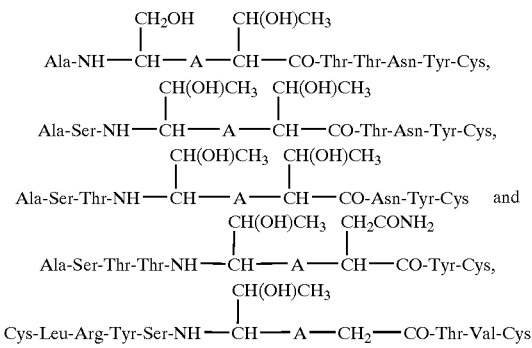

wherein A is as hereinbefore defined.

A preferred hapten according to formula II is (R)-2-hydroxymethyl-2-hydroxy-propanoic acid diol 1-amino-2-phenylethaneboronate.

Other preferred haptens according to formulae II and III include those in which $R_1$ is selected from the group consisting of $CH_2OH$ and $CH(OH)CH_3$, $R_2$ is selected from the group consisting of $CH(OH)CH_3$ and $CH_2CONH_2$; X is selected from the group consisting of amino bonded to the C terminus of alanine, amino bonded to the C terminus of serine in the dipeptide Ala-Ser, amino bonded to the C terminus of threonine in the tripeptide Ala-Ser-Thr and amino bonded to the C terminus of theronine in the polypeptide Ala-Ser-Thr-Thr; and Y is selected from the group consisting of carbonyl bonded to the N terminus of threonine in the polypeptide Thr-Thr-Asn-Tyr-Cys, carbonyl bonded to the N terminus of threonine in the polypeptide Thr-Asn-Tyr-Cys, carbonyl bonded to the N terminus of asparagine in the tripeptide Asn-Tyr-Cys and carbonyl bonded to the N terminus of tyrosine in the dipeptide Tyr-Cys. Still other preferred haptens of formulae II and III include those in which $R_1$ is $CH(OH)CH_3$, $R_2$ is H, X is amino bonded to the C terminus of serine in the polypeptide Cys-Leu-Arg-Tyr-Ser and Y is carbonyl bonded to the N terminus of threonine in the tripeptide Thr-Val-Cys.

One application of catalytic antibodies having site-specific proteolysis capabilities is in the immunotherapy of viral infection. Viruses utilize their external coat proteins to attach to cellular receptors and invade the cell after attachment. For example, human immunodeficiency virus (HIV) uses a portion of the gp120 protein at its surface to attach to CD4 receptors on lymphocytes. The sequence for this cell attachment has been mapped to a region on the viral protein. With this information, antibodies can be generated by the methodology described in this invention to bind to this peptide sequence and cleave it in a site-specific manner. However, such antibodies preferably bind to the "native" sequence in the protein as opposed to a linear sequence (which would occur in a denatured protein). Thus, the antigenic determinants or epitopes in the "native" protein are often conformational (i.e., three-dimensional) rather than random linear arrangements. Here again, knowledge of epitopes on the protein is important in the design of antibodies having paratopes that can induce modifications of such epitopes.

Therefore, haptens according to the invention are designed to have the same structural features of the epitopes, rather than random conformations. These structural features can be adopted by simple linear peptides, the lowest energy conformer being the preferred structure in solution. Secondary structural features may be introduced by cross-linking of amino-acid side-chains or the use of β-turn mimetics. Conformationally constrained haptens incorporating structures which are compatible with the epitope in the native protein may be essential for inducing the correct motif within the tertiary structure of the catalytic antibody hyper-variable binding region. The advantages of conformationally constrained haptens are that they mimic the native structure in the protein and tend to mimic regions of the protein which are susceptible to cleavage.

Accordingly, in the structural formula I shown above for the haptens of the invention, the substituents $R_1$, $R_2$, X and Y may be bound to one or more of the remaining substituents $R_1$, $R_2$, X and Y by a covalent bond or a linker moiety as defined above. Likewise, in formulae I, the substituents $Z_1$–$Z_6$ may be covalently bonded to the linker moiety by substitution at an appropriate atom in the linker moiety.

Preferred conformationally constrained haptens are represented by formula IA

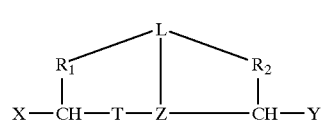

(IA)

wherein
$R_1$, $R_2$, X and Y and are as defined with reference to formula I above;

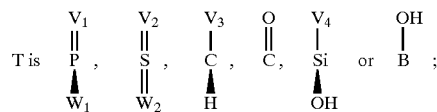

Figure 9:
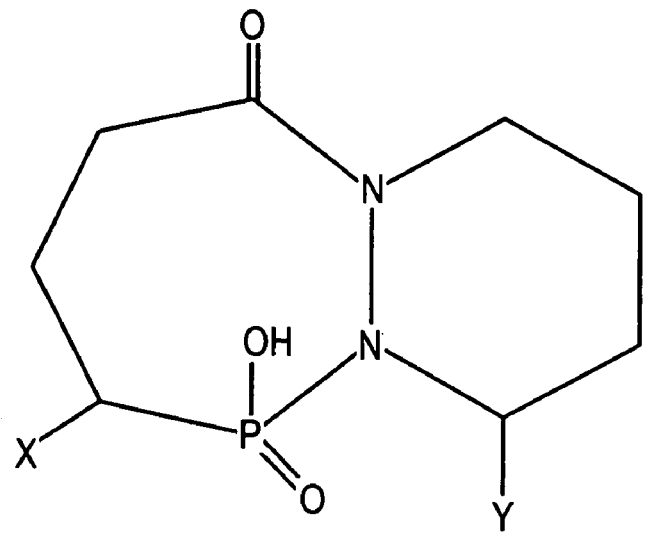
FIG. 9 depicts pyradazinedione analogs.
Figure 9:
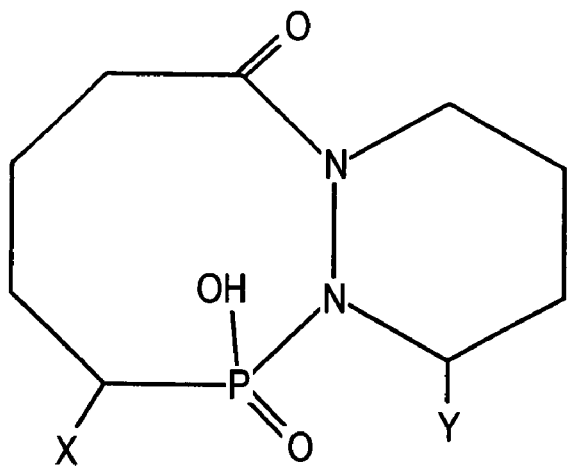
Figure 9:
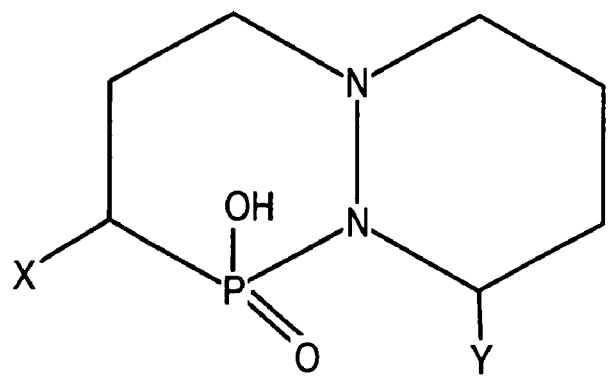
Figure 10:
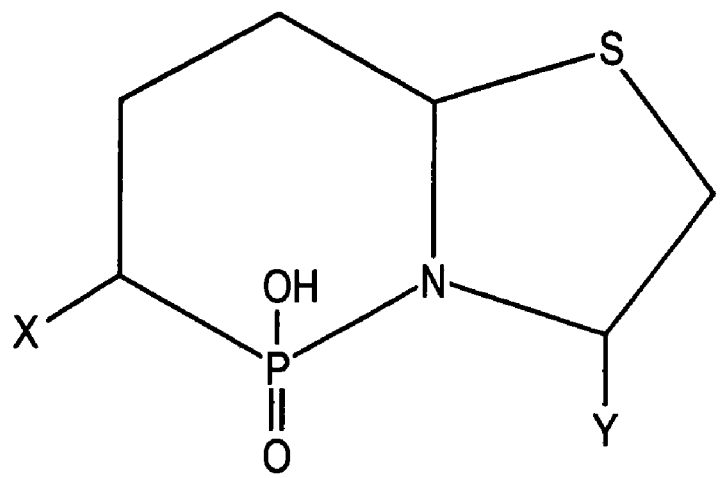
FIG. 10 depicts bicyclic β-turn and rigid tricyclic analogs.
Figure 10:
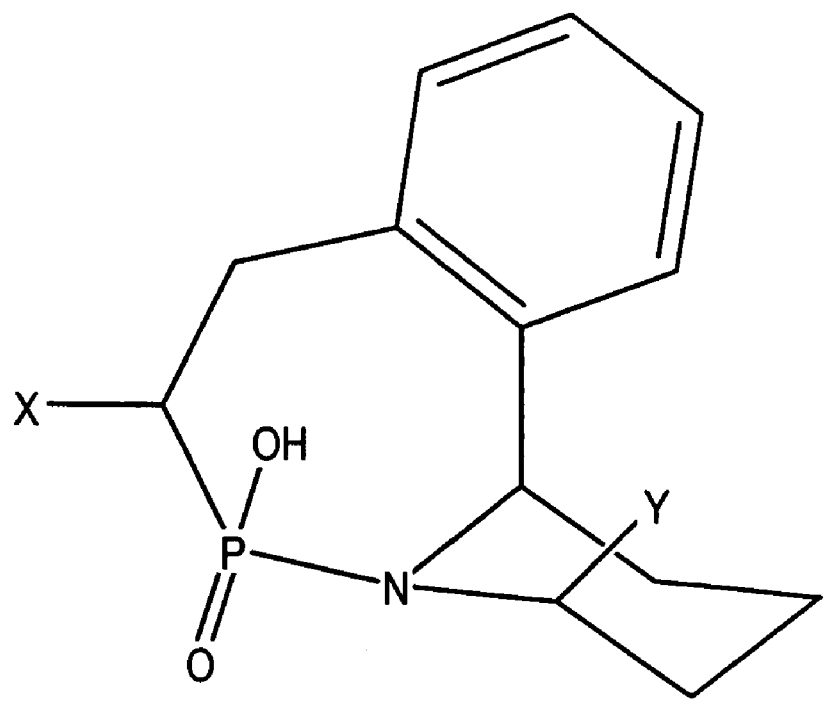
Figure 11:
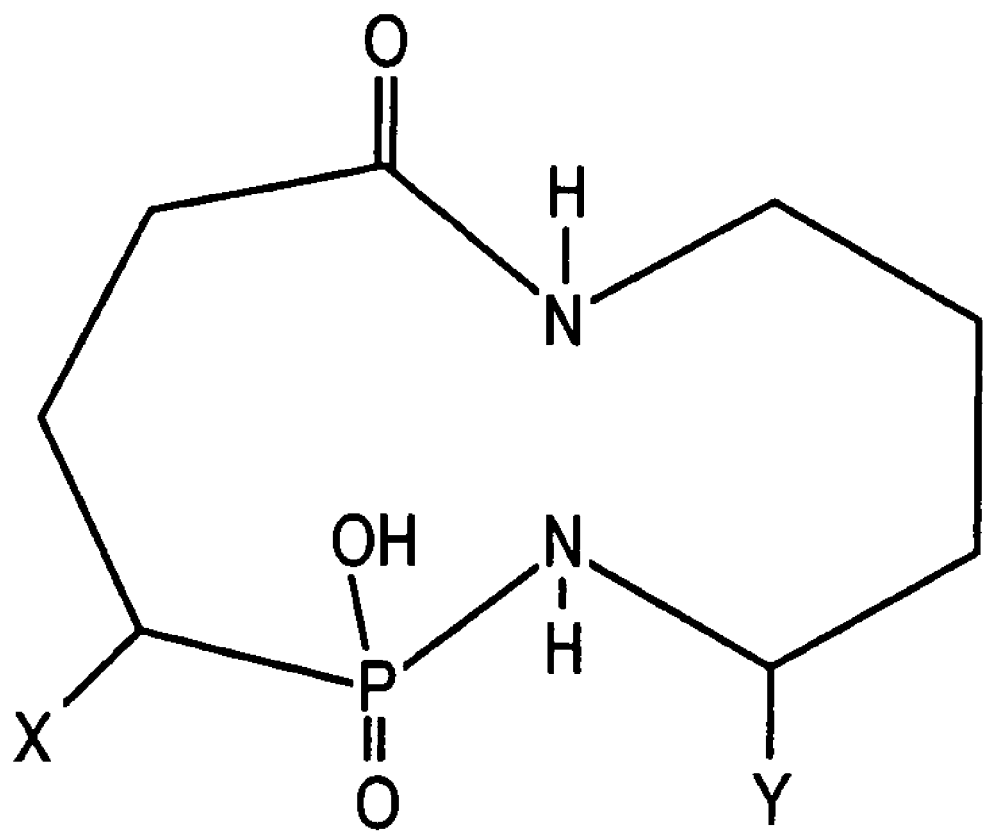
FIG. 11 depicts macrocyclic β-turn analogs.

$V_1$, $V_2$, $V_3$, $V_4$, $W_1$ and $W_2$ are as defined with reference to formula I above;

Z is $Z_1$, $Z_2$, $Z_3$, $Z_4$ or $Z_5$ as defined with reference to formula I above; and L is N or CH in the linker moiety as defined with reference to formula I above. These include pyradazinedione analogs, shown in FIG. 9, bicyclic beta-turn and rigid tricyclic analogs, shown in FIG. 9 and macrocyclic-turn analogs in FIG. 11. On comparison of the haptens set forth in FIGS. 9, 10 and 11 and the general formula IA, the skilled artisan will readily appreciate that the side chains $R_1$ and $R_2$ are —$CH_2$— or —$CH_2CH_2$— and these side chains $R_1$ and $R_2$ are joined by the linker moiety "L" which is —$CH_2$—CO—N—$CH_2$—, —$CH_2$—N—$CH_2$, —$CH_2$—CH—S— or -ortho-phenyl-CH—$CH_2$—. The nitrogen atom corresponding to the Z substituent is covalently bonded to the aforementioned linker moieties by substitution at an appropriate atom in the linker moiety, i.e., at the nitrogen atom in the first two linker moieties listed, at the carbon atom adjacent to the sulfur atom in the third linker moiety listed and at the carbon atom adjacent to the phenyl ring in the fourth linker moiety listed. Of course, the microcyclic-β-turn analog shown in FIG. 11 corresponds to the generic formula I wherein the Z substituent is not bound to the linker moiety. While in FIGS. 9, 10 and 11 phosphonamidate analogs are depicted, it is to be understood that any of the other tetrahedral carbon mimics according to the invention (e.g., —$SO_2$—, —$CHNH_2$—, CHOH—, —$Si(OH)_2$—, etc.) may also be used.

The haptens of the invention can also take on a configuration mimicking that of the native β-turn or "hairpin" configuration of proteins by the formation of disulphide bridges between sulfur containing amino acid side chains which are incorporated into the hapten. Formation of disulphide bridges also promotes hydrogen bonding interactions. Disulphide bridge formation can be achieved by chemical methodology well known in the art.

It will be understood by the skilled artisan that the following syntheses may be modified to provide other haptens of the invention.

Figure 12:
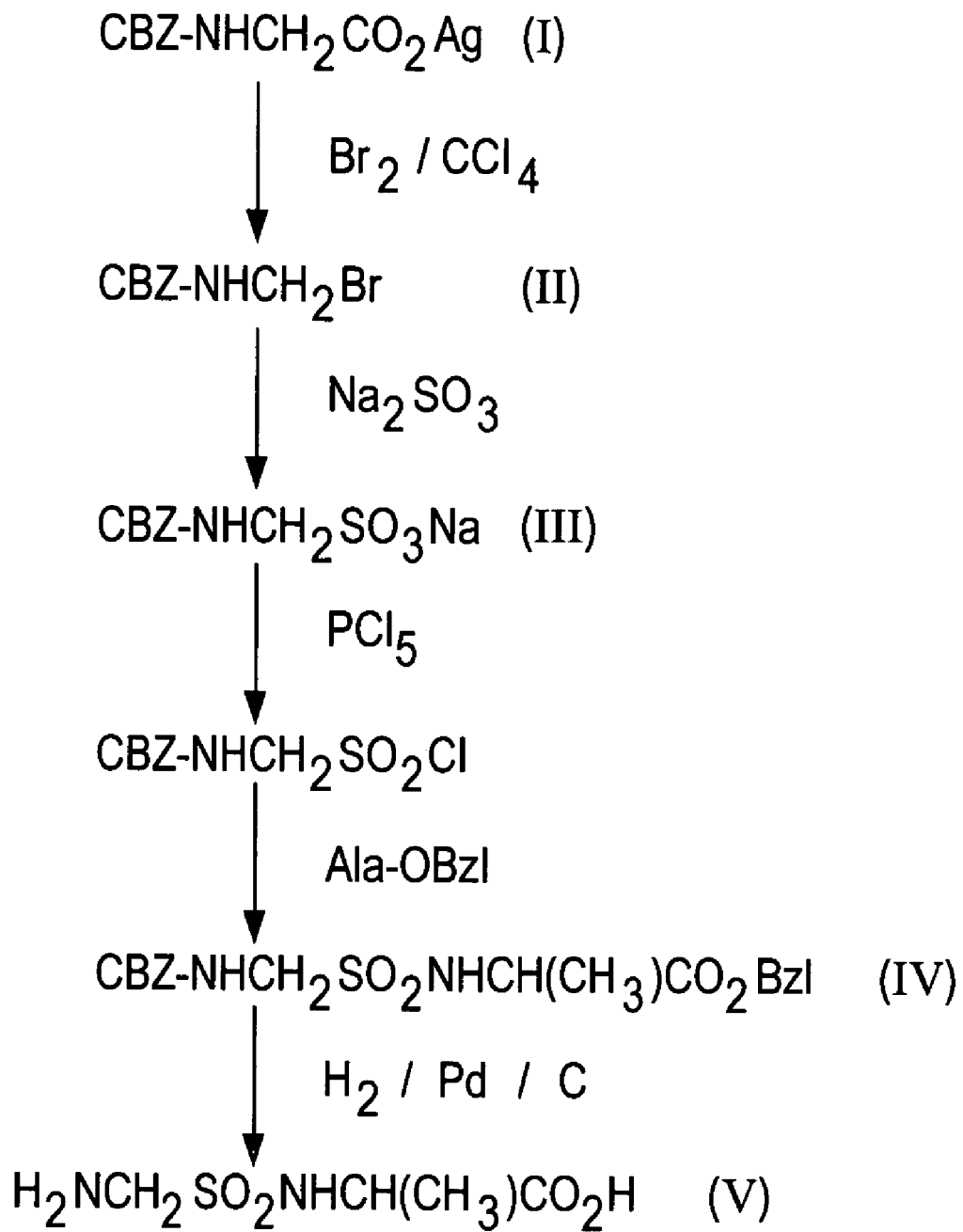
FIG. 12 schematically shows the reaction sequence for the synthesis of aminomethanesulfonamidylalanyl acid (V)

The synthesis of aminomethanesulfonamidylalanyl acid, a hapten of the general formula I containing a central sulfur atom, is shown schematically in FIG. 12. The silver salt of N(-benzyloxycarbonyl) glycine (I) is converted to bromoderivative (II) by treating it with bromine in carbon tetrachloride according to a literature procedure (28). Reaction of the bromoderivative (II) with aqueous sodium sulfite under reflux converts it to the sulfonate derivative (III). Activation with phosphorus pentachloride and reaction with L-alanine benzyl ester gives compound (IV) which is fully deprotected to afford the final product (V) by catalytic hydrogenation with 10% palladium on activated carbon. The synthesis is set forth in more detail in the examples below.

Figure 13:
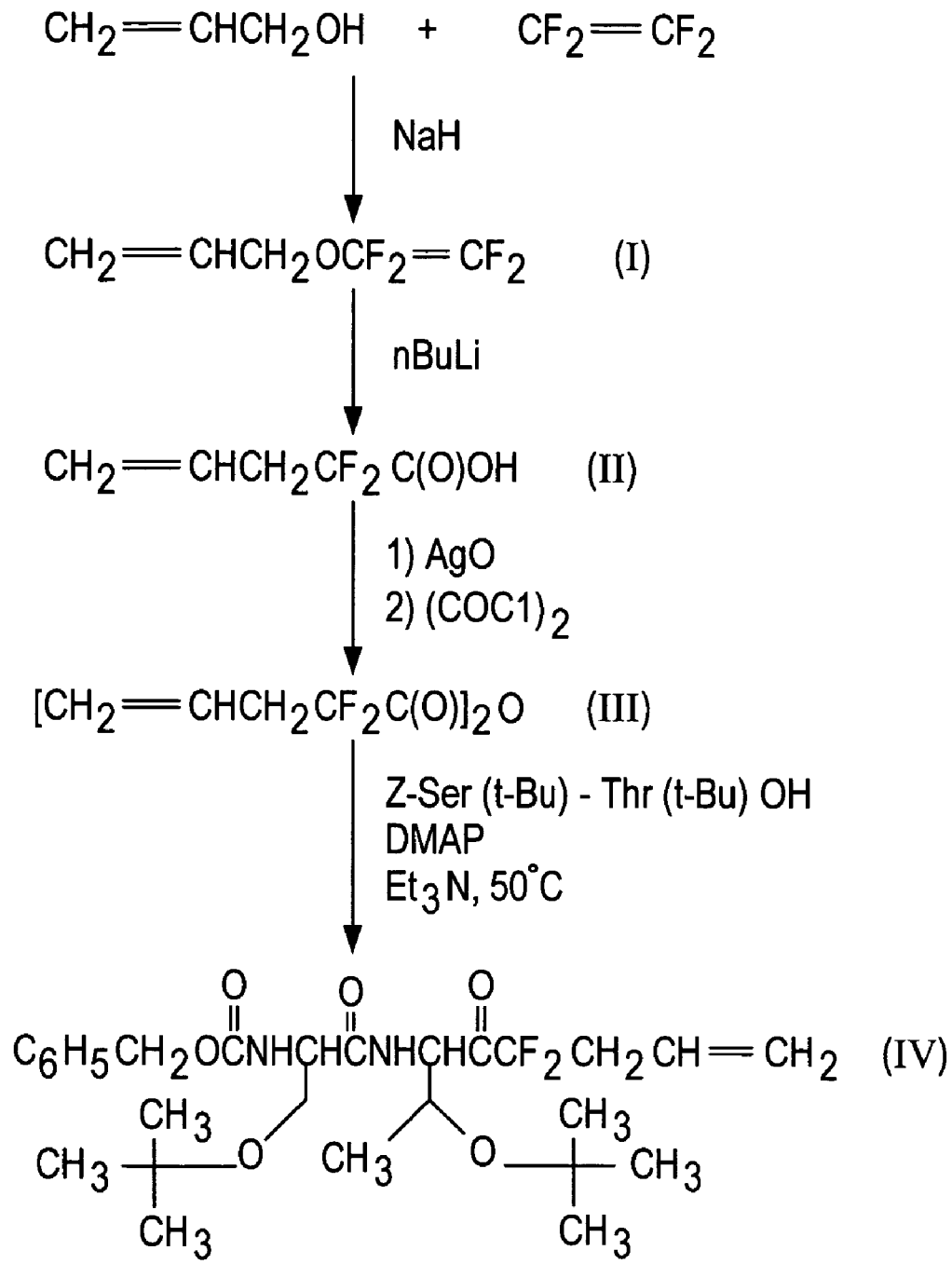
FIG. 13 schematically shows the reaction sequence for the synthesis of 5-(serinyl)amino 3,3-difluoro 4-oxo 6-hydroxy heptanoic acid (VII)
Figure 13:
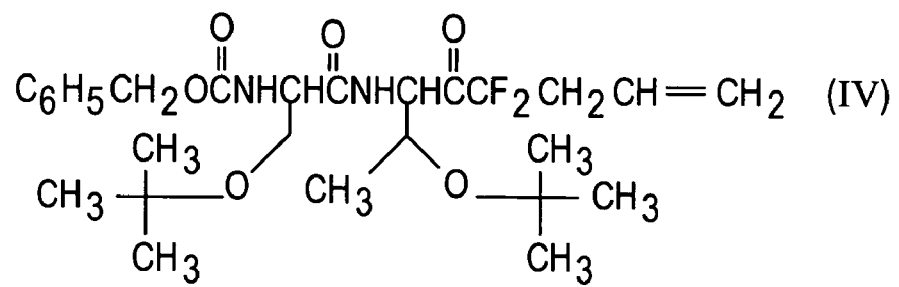
Figure 13:
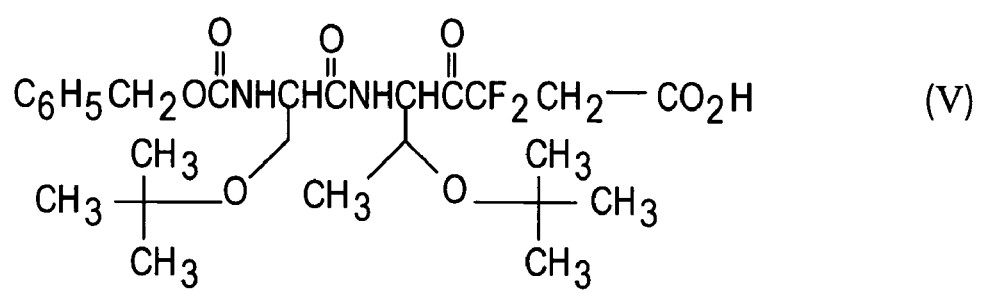
Figure 13:
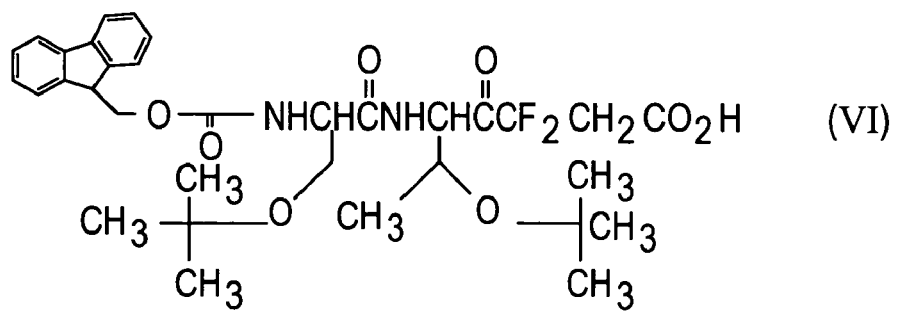
Figure 13:
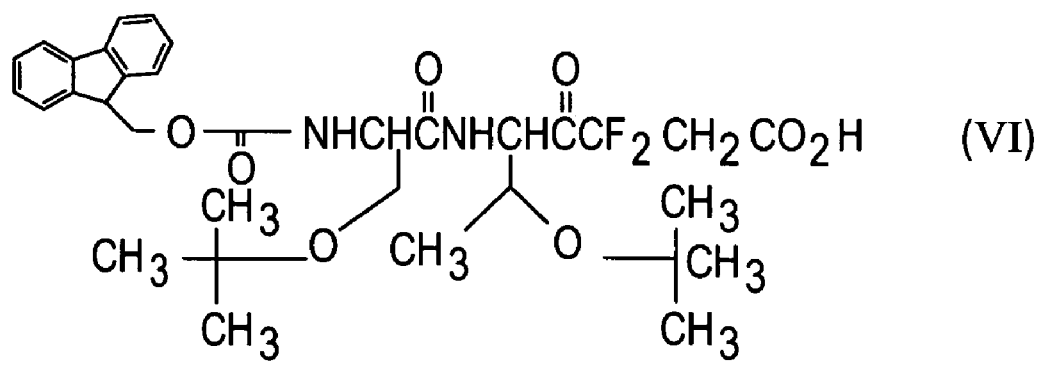
Figure 13:
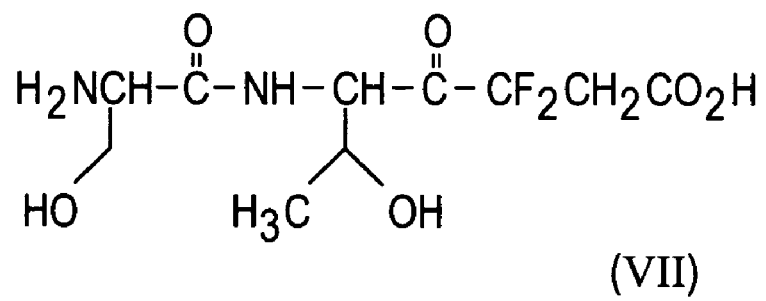

The synthesis of 5-(serinyl)amino 3,3-difluoro 4-oxo 6-hydroxy heptanoic acid, a difluoroketone hapten according to formula I, is shown schematically in FIG. 13. The synthesis of intermidiates I–III is disclosed in M. Kolb et al.

European Patent Application No. 86101437.1. The acid fluoride (II) is prepared by reacting allyl alcohol with tetrafluoroethylene in the presence of sodium hydride and the resultant intermediate (I) is treated with n-butyllithium. The acid fluoride (II) is converted to its silver salt with aqueous silver oxide. After drying the salt over phosphorus pentoxide, it is converted to the anhydride (III) by reacting with oxalyl chloride.

Compound (V) is prepared by the reaction of Z-Ser(t-Bu)-Thr(t-Bu)-)OH with 2,2-difluoro-4-pentenoic acid anhydride (III) in the presence of triethylamine and 4-dimethylaminopyridine at 50° C. for one hour. Treatment of compound (IV) with ozone at −78° C. in dichloromethane followed by dimethylsulfide and then Jone's oxidation solution (1M $CrO_3/H_2SO_4$) overnight yields compound (V). The final product VII is prepared by the removal of the Z group by catalytic hydrogenation followed by the reaction of the liberated amine compound with 9-fluorenylmethyl chloroformate to give compound (VI). Compound (VI) is then fully deprotected to give compound (VII). The synthesis is described in more detail in the examples below.

Figure 14:
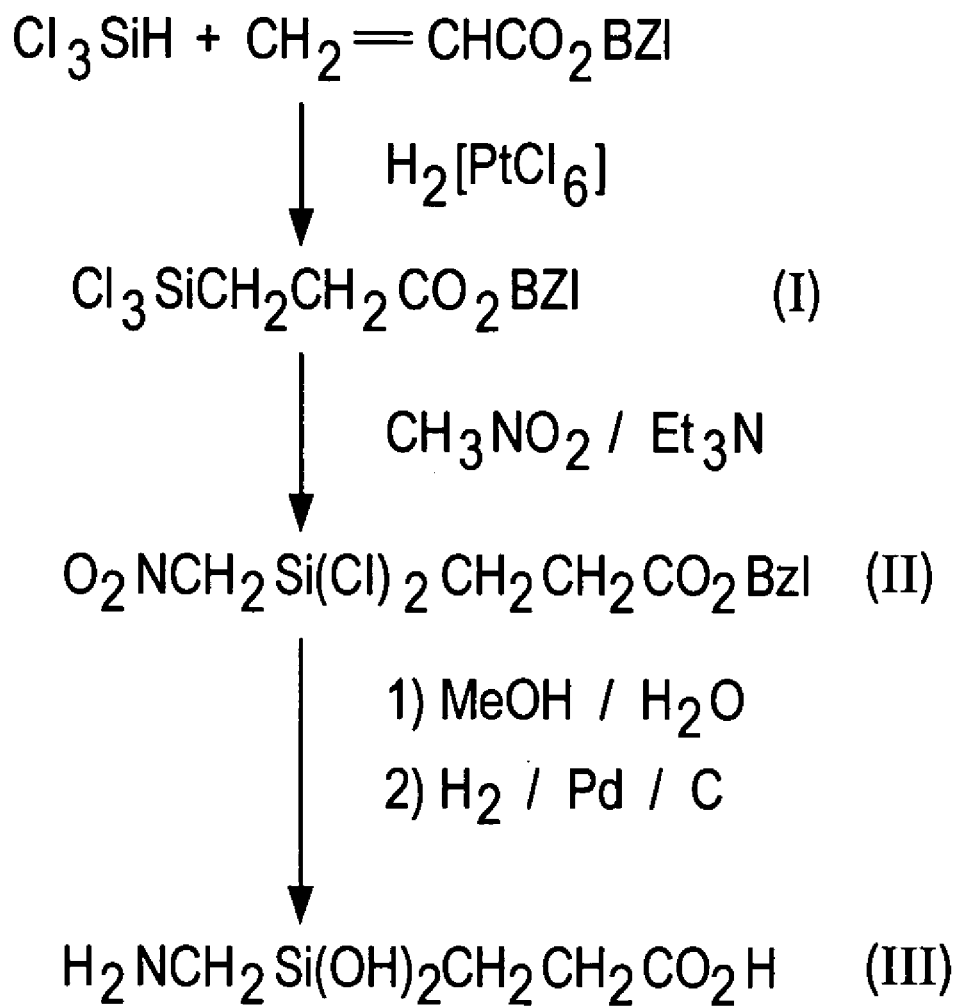
FIG. 14 shows schematically the reaction sequence for the synthesis of 3-(aminomethyldihydroxysilyl) propionic acid (III)

The synthesis of 3-(aminomethyldihydroxysilyl) propionic acid benzyl ester, a hapten according to formula I containing a central silicon atom, is shown in FIG. 14. The 3-(trichlorosilyl) propionic acid (I) is prepared by the reaction of trichlorosilane with vinyl benzyl ester in the presence of a catalytic amount of chloroplatinic acid in isopropanol at 20° C. Compound (I) when reacted with nitromethane and triethylamine followed by hydrolysis and catalytic hydrogenation in methanol-water yields the product (III). The synthesis is described in more detail in the examples below.

Figure 15:
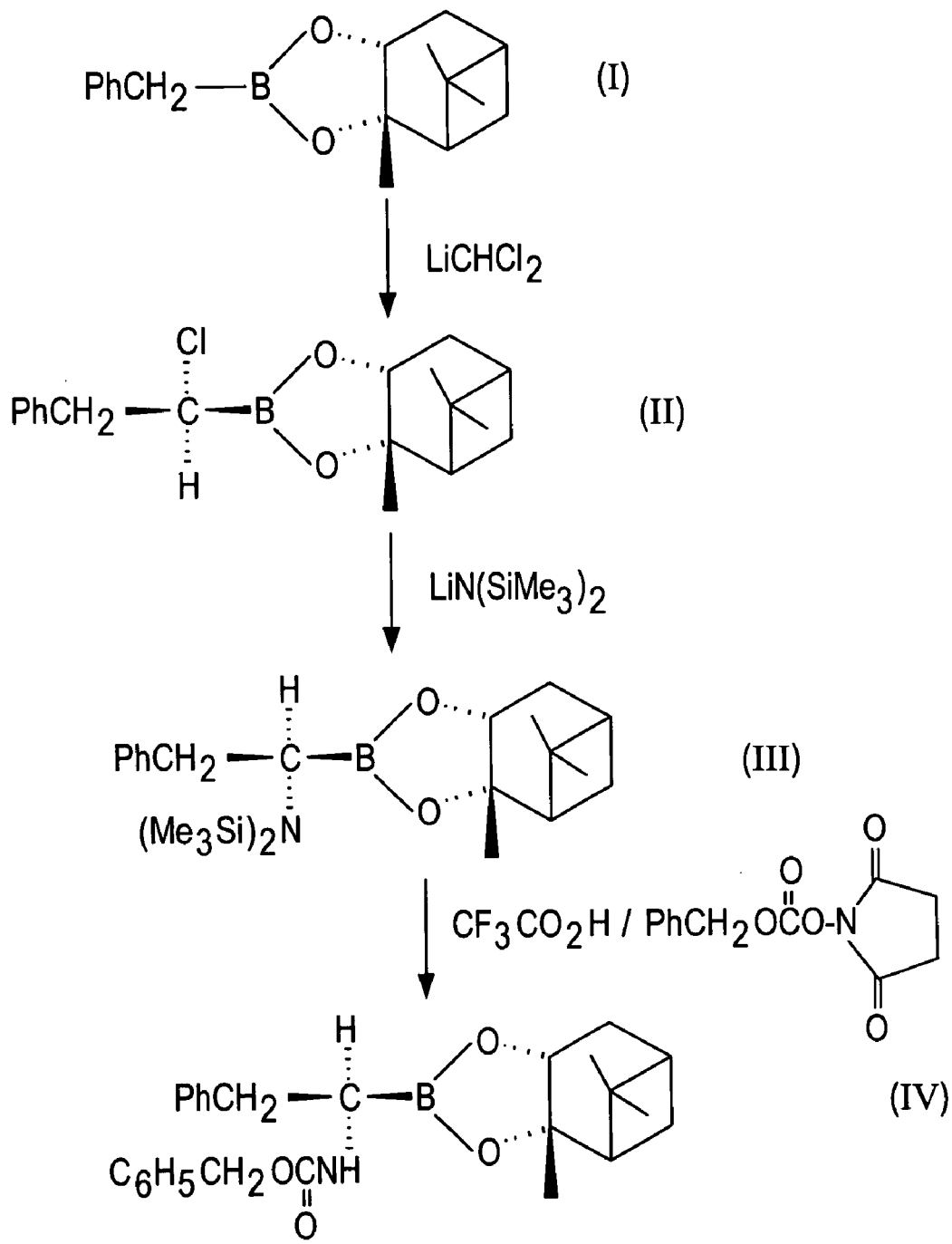
FIG. 15 shows schematically the reaction sequence for the synthesis of (S-lactate-1-(R)-amino-2-phenylethanebor-onate) (VIII)
Figure 15:
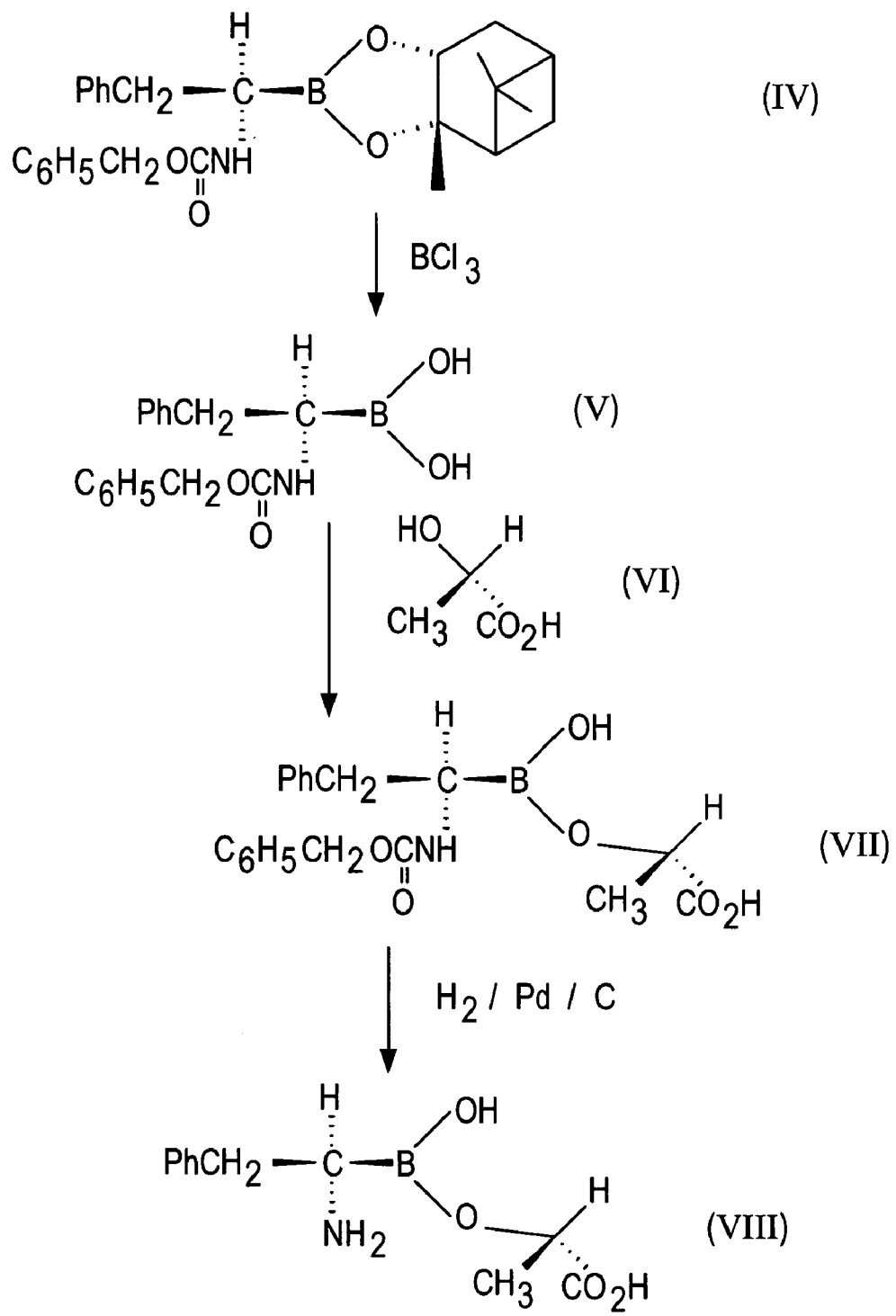

The synthesis of (S)-lactate-1-(R)-amino-2-phenylethane boronate, a preferred boron-containing hapten of formula I, is shown in FIG. 15. The synthesis of intermediates I–IV closely follows a literature procedure (29) except that the literature procedure is modified by using trifluoroacetic acid and N-(benzyloxycarbonyloxy) succinamide in place of acetic acid and acetic anhydride.

(+)-Pinanediol benzyl boronate (I) is homologated with (dichloromethyl) lithium to compound (II) which is treated in situ with lithiohexamethyldisilazane followed by three equivalents of N-(benzyloxycarbonyloxy) succinimide and one equivalent of trifluoroacetic acid to yield (+)-pinanediol (R)-1-benzyloxycarbonylamino-2-phenylethane boronate (IV). Removal of the pinanediol ester with boron trichloride yields (R)-1-benzyloxycarbonylamino-2-phenylethane boronic acid which can be characterized as its reversibly formed boronic anhydride (V). Heating under vacuum converts the acid to the anhydride which when treated with (S)-(+)-lactic acid (VI) yields (VII). Removal of the carboxylbenzyl group via catalytic hydrogenation affords the desired product (VIII). A detailed description of the synthesis is set forth in the examples below.

Figure 16:
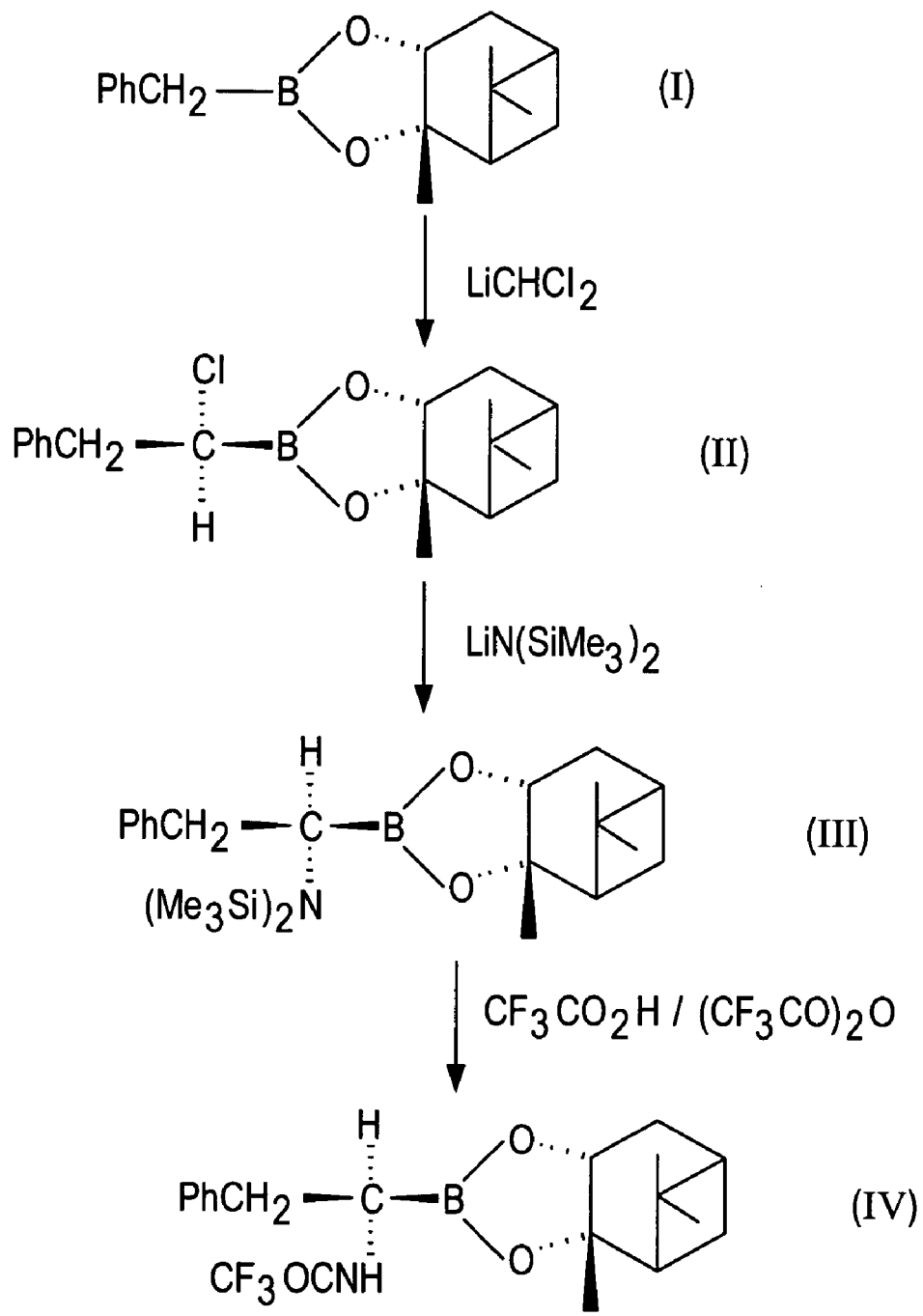
FIG. 16 shows schematically the reaction sequence for the synthesis of (R)-2-hydroxymethyl-2-hydroxy-propanoic acid diol-1-amino-2-phenyl-ethaneboronate (VIII)
Figure 16:
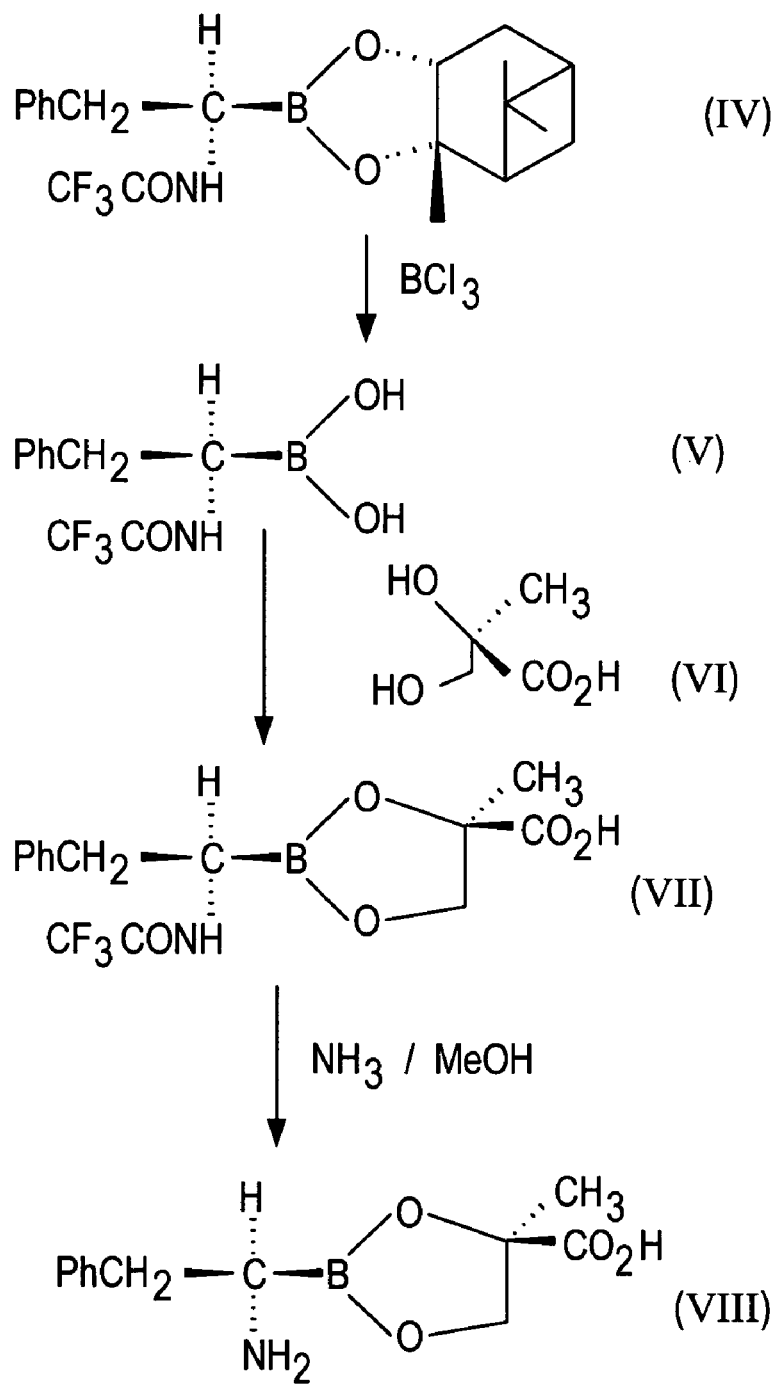

The synthesis of a preferred hapten of general formula II, (R)-2-hydroxymethyl-2-hydroxy-propanoic acid diol-1-amino-2-phenyl-ethaneboronate, is shown in FIG. 16. The synthesis of intermediates I–IV closely follows a literature procedure (29). The literature procedure is modified by using trifluoroacetic acid and trifluoroacetic anhydride in place of acetic acid and acetic anhydride.

(+)-Pinanediol benzylboronate (I) is homologated with (dichloromethyl)lithium to compound (II) which is treated in situ with lithiohexamethyldisilazane followed by three equivalents of trifluoroacetic anhydride and one equivalent of trifluoroacetic acid to yield (+)-pinanediol (R)-1-trifluoroacetamido-2-phenylethane-boronate (IV). Removal of the pinanediol ester with boron trichloride yields (R)-1-trifluoroacetamido-2-phenylethaneboronic acid (V) which can be characterized as its reversibly formed boronic anhydride. Heating under vacuum converts the acid to the anhydride which when treated with at least three equivalents of (R), 2-(carboxymethyl)-2-hydroxy propanoic acid (VI) yields compound (VII). The synthesis of the hydroxy propanoic acid is described in the literature (30). Removal of the trifluoroacetyl group with ammonia in methanol affords the desired product (VIII). A more detailed description of the synthesis is set forth in the examples below.

Figure 17:
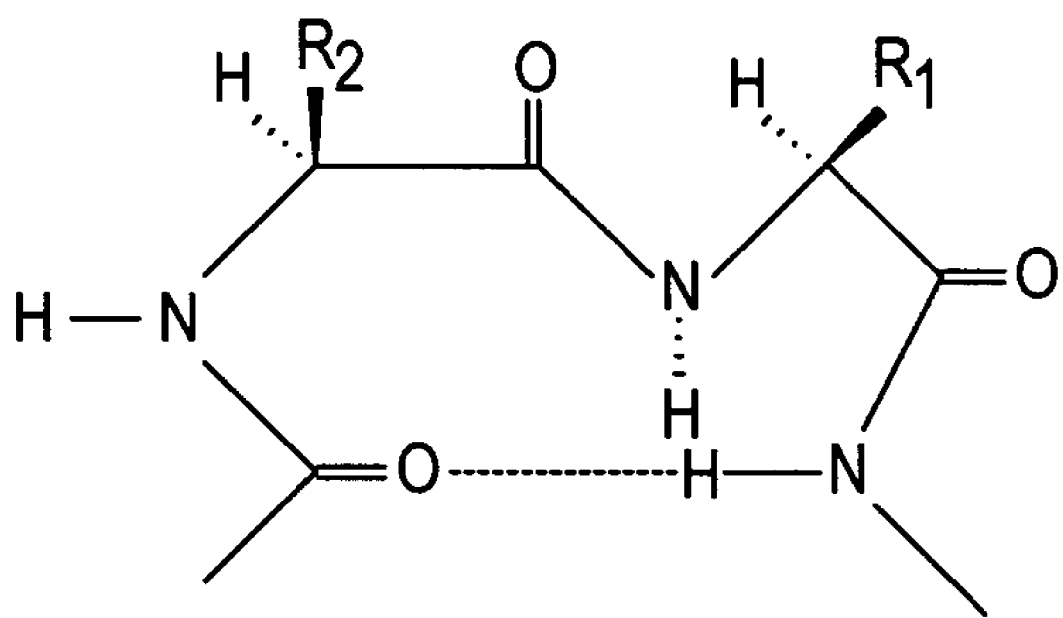
FIG. 17 depicts a type I β-turn.
Figure 18:
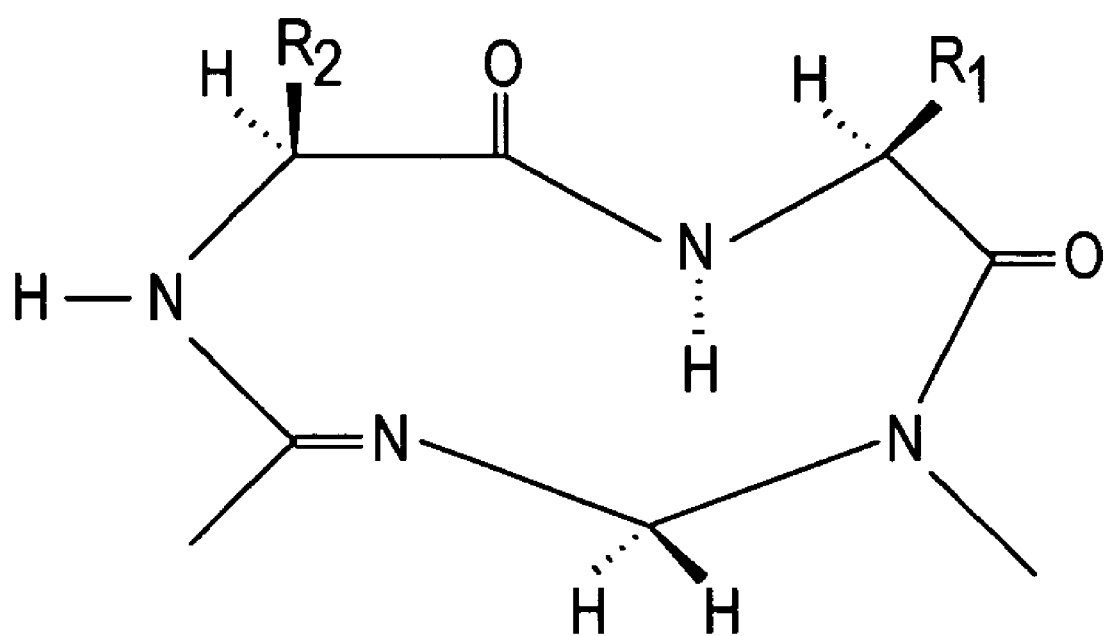
FIG. 18 depicts a β-turn containing a N-amino-methyla-midinium covalent link.
Figure 19:
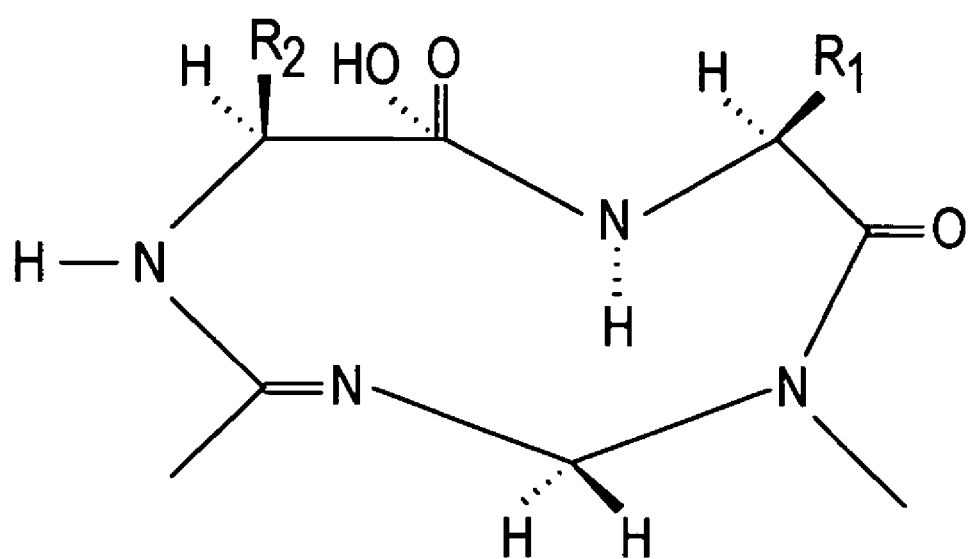
FIG. 19 depicts a phosphonamidate hapten according to the invention having the β-turn conformation.

As noted earlier, the invention is also directed to conformationally constrained haptens which mimic the native configurations of proteins. FIG. 17 is a type I β-turn where the carbonyl group of the residue is hydrogen-bonded to the amino group of the residue C+3. It is possible with a change of conformation with the same hydrogen bond intact to form other types of β-turns such as type II or type III ($3.0_{10}$ helix). In all of the different types of β-turns it is desirable to replace the hydrogen bond for a covalent link such as the N-aminomethylamidinium link as shown in FIG. 18. The molecule is now locked into a β-turn. Therefore, replacing the amide bond between residues $R^1$ and $R^2$ by a transition state analog gives a conformationally constrained hapten as shown in FIG. 19 useful for eliciting catalytic antibodies.

Figure 20:
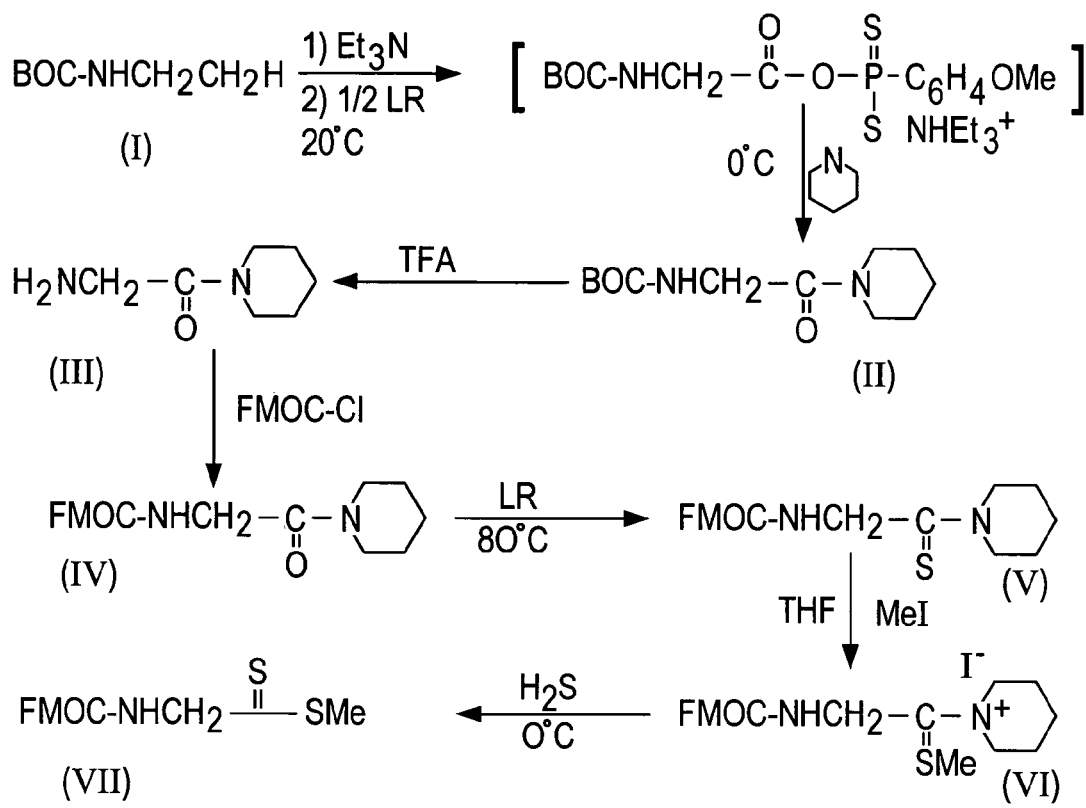
FIG. 20 shows Scheme 1 in the synthesis of the conformationally constrained hapten shown in FIG. 19.
Figure 20:
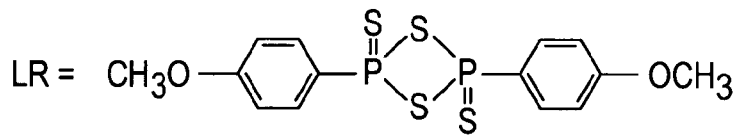
Figure 21:
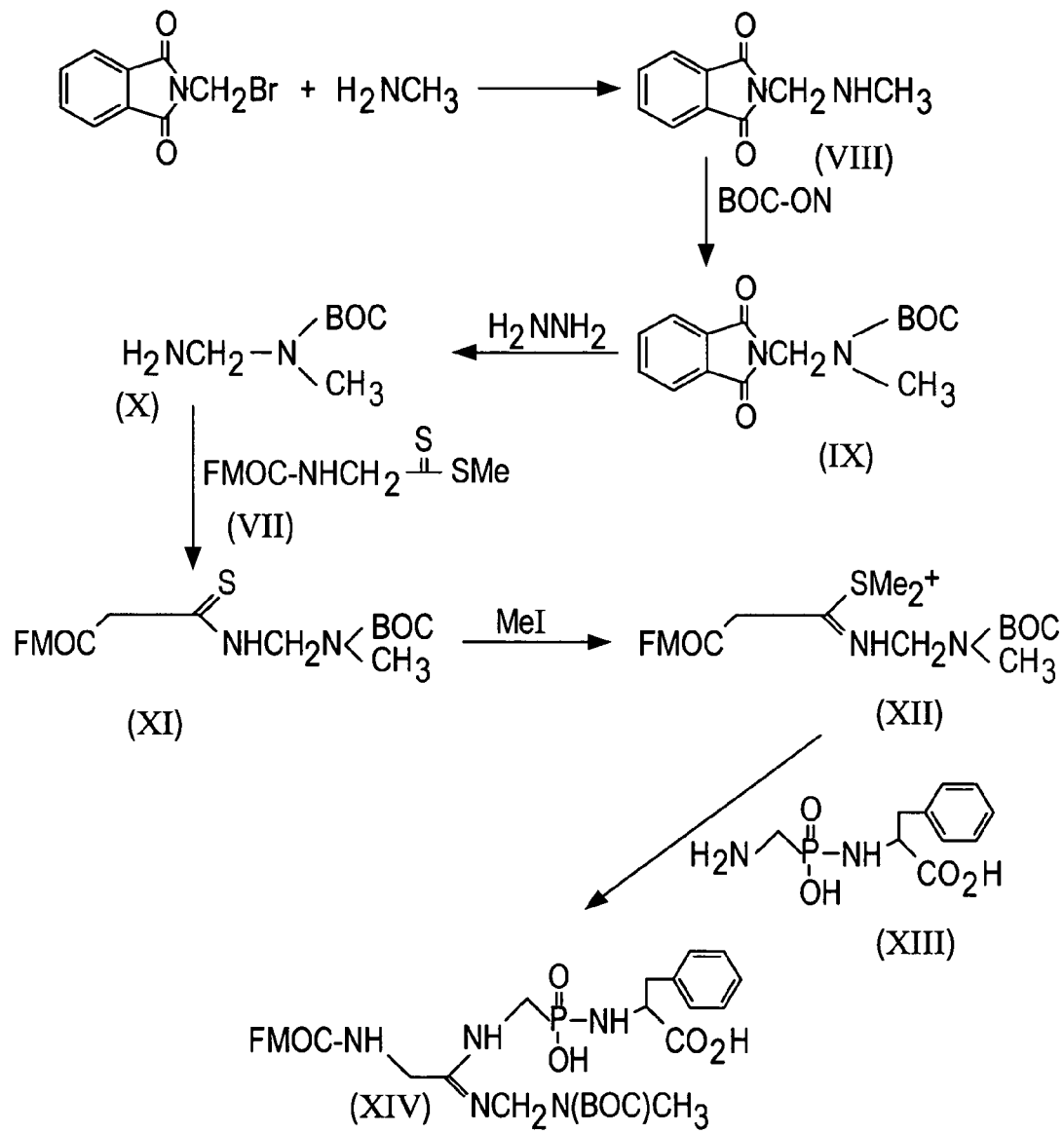
FIG. 21 shows Scheme 2 in the synthesis of the conformationally constrained hapten shown in FIG. 19.
Figure 21:
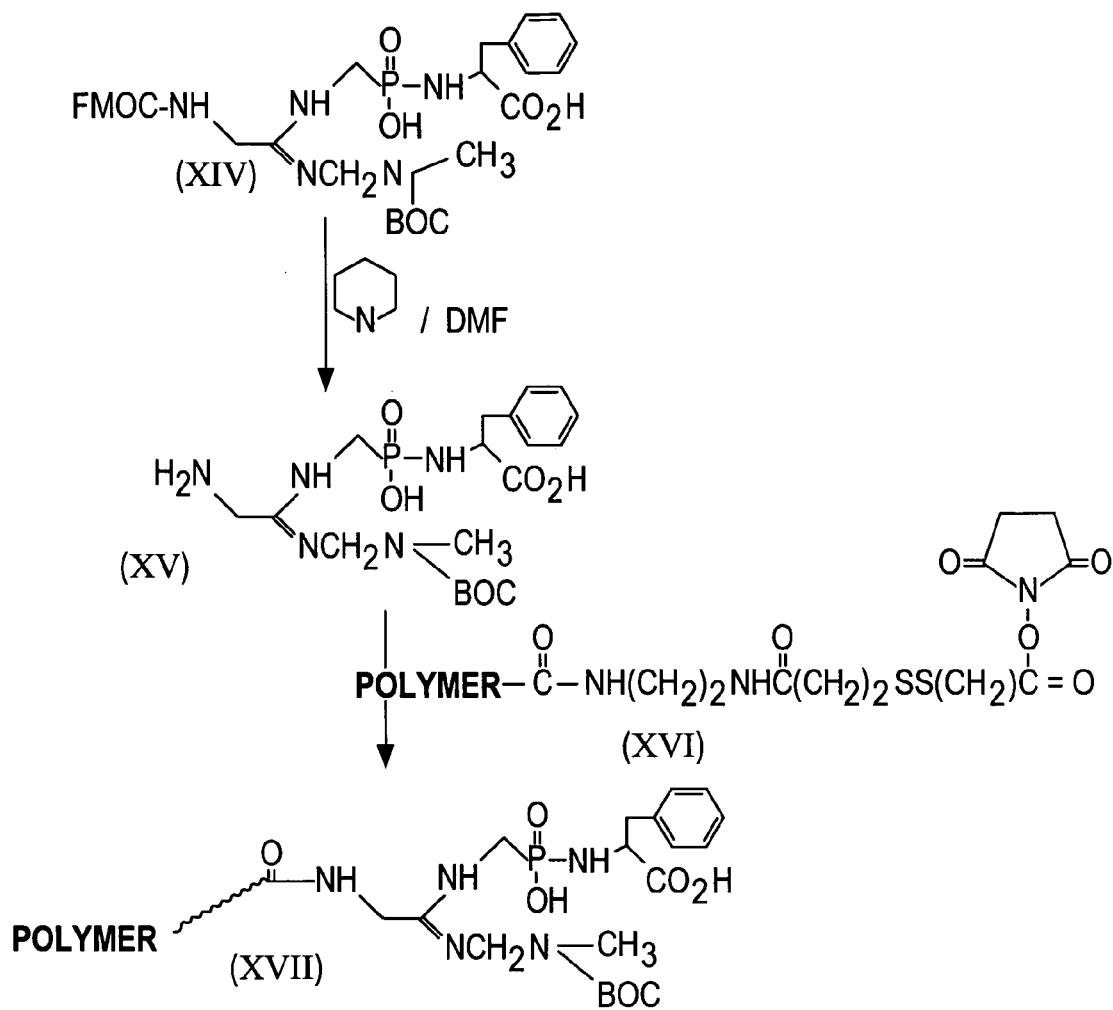
Figure 21:
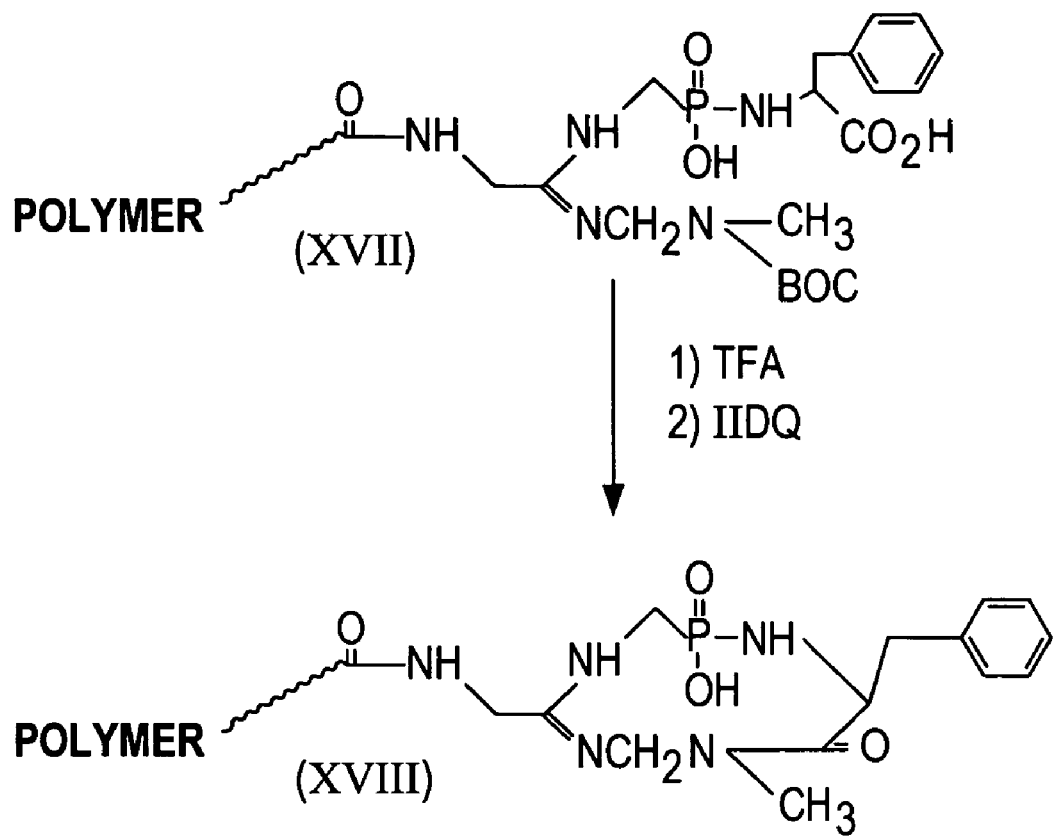

The synthesis of the above mimetic of a β-turn (FIG. 19) is in two parts: first, the preparation of the dithioester (VII) as shown in FIG. 20 (Scheme 1); and second, the formation of the ten membered ring as shown in FIG. 21 (Scheme 2). The method for preparing the dithioester VII follows essentially a literature procedure (31).

The BOC-protected glycine (I) is first converted to the triethylamine salt by treatment with triethylamine and is then transformed to the corresponding piperidide (II) by the reaction of the BOC-protected glycine triethylamine salt with Lawesson's reagent (LR) and piperidine. Removal of the BOC group by trifluoroacetic acid followed by the addition of FMOC-Cl gives the FMOC-protected glycylpiperidide (IV). Lawesson's reagent is next used as a thionation reagent to form the corresponding thiopiperidide (V). The thiopiperidide is S-methylated by reaction with an excess of methyl iodide in THF for 12 hrs. to give (VI). Thiolysis using hydrogen sulphide at 0° C. yields the dithioester (VII).

Figure 22:
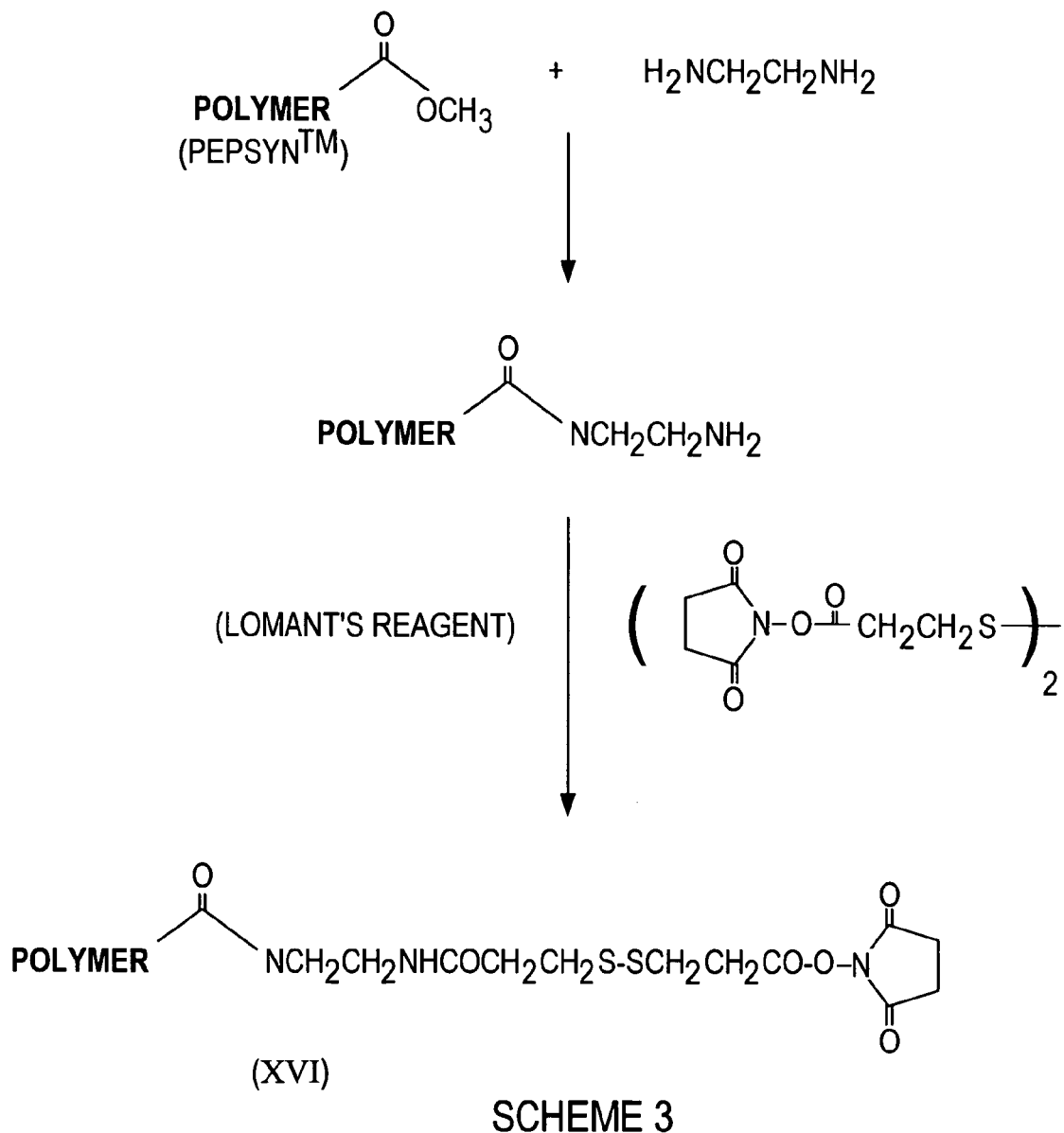
FIG. 22 shows Scheme 3 in the synthesis of the conformationally constrained hapten shown in FIG. 19.
Figure 23:
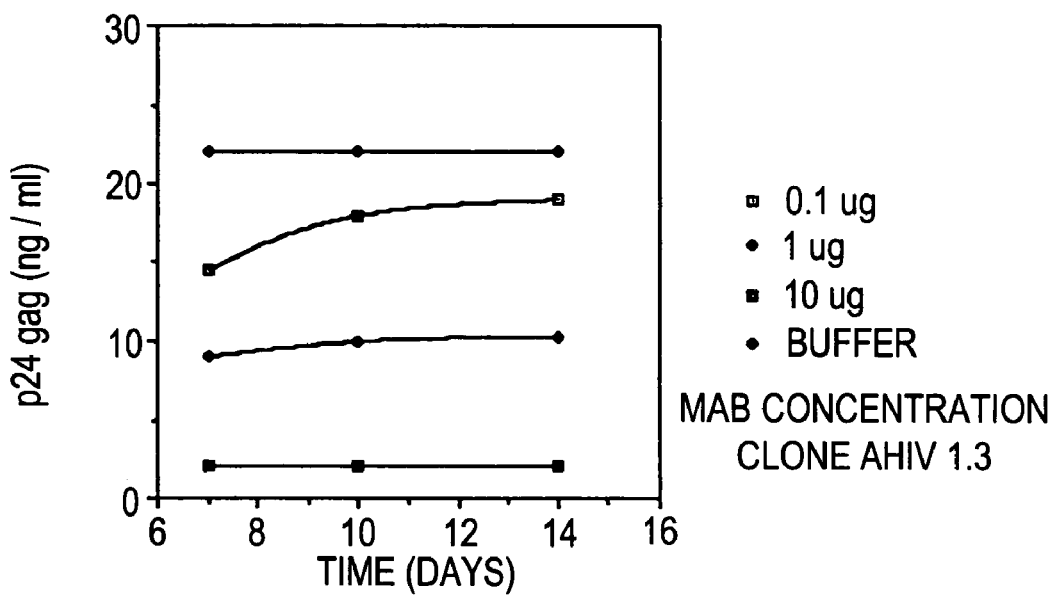
FIG. 23 shows the dose dependant inhibition by clone AHIV 1.3 of HIV-I p 24 gag production in infected H9 cells.
Figure 24:
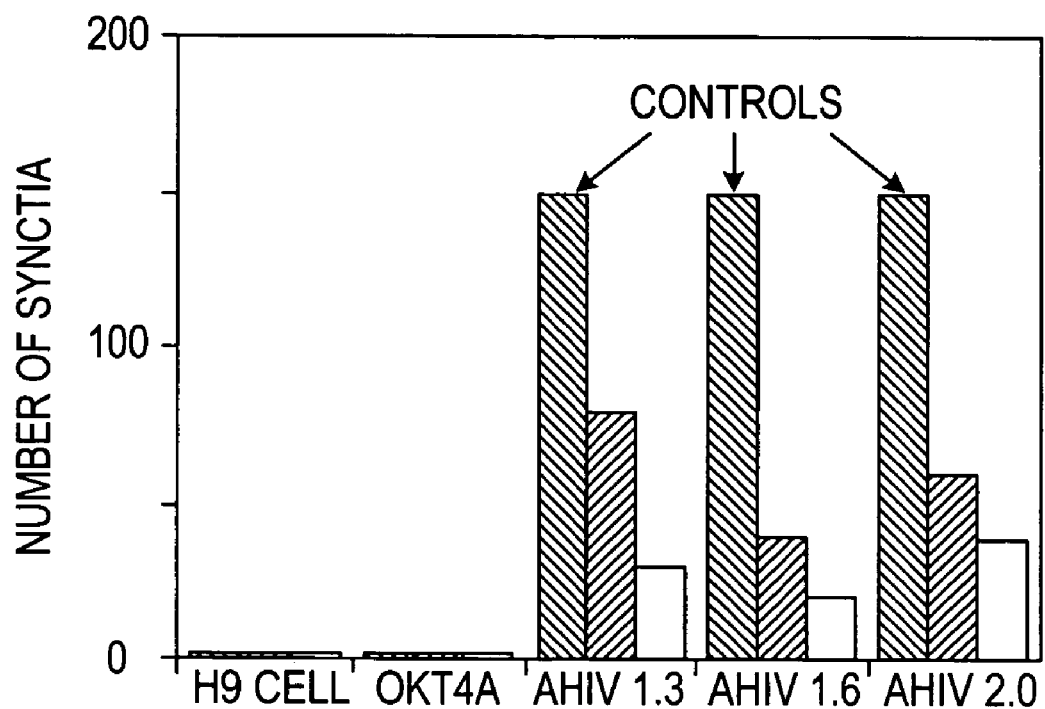
FIG. 24 shows the dose dependant inhibition by clones AHIV 1.3, AHIV 1.6 and AHIV 2.0 of HIV-1-induced cell-fusion.

The formation of the ten membered ring compound (Scheme 2) begins with the reaction of bromomethylphthalimide with methylamine to give the secondary amine (VIII). Addition of 2-[(t-butoxycarbonyloxyimino)-2-phenylacetonitrile] followed by removal of the phthalimide group with hydrazine yields the primary amine (X). Thioacetylation of (X) with the dithioester (VII) from Scheme 1 followed by activation with methyl iodide and condensation with (L)-α-2-aminophosphonamide acid (XIII) gives compound (XIV). The polyamide gel resin (XVI) functionalized as a succinimide ester is prepared by reacting the polyamide gel resin functionalized as sarcosine methyl ester (commercially available as Pepsyn™ from CRB Ltd.) with ethylenediamine followed by Lomant's reagent as shown in FIG. 22 (Scheme 3). Compound (XVII) is prepared by first removing the FMOC group from compound (XIV) with pyridine in DMF followed by reaction with the activated resin (XVI). Removal of the BOC group with trifluoroacetic acid followed by internal cyclization using IIDQ gives the final product (XIX). The presence of the disulphide linker in product (XIX) allows the release of the product into free solution by reductive cleavage using dithiothreitol under basic conditions. The product may then be purified and analyzed before attaching to a carrier protein using the bifunctional linker, sulfosuccinimidyl 4-(N-maleimido-methyl)cyclohexane-1-carboxylate.

The utility of the antigens of this invention coupled with appropriate screening procedures and reiterative thermodynamic perturbation studies of transition-state structures and free-energies of interaction with catalytic groups provide a methodology for production of catalytic antibodies by a rational design approach.

The invention also is directed to catalytic antibodies which are elicited by antigens comprising haptens according to the invention. These antibodies may be monoclonal or polyclonal but are preferably monoclonal.

Catalytic antibodies according to the invention may be elicited through both in vitro and in vivo techniques. The term "elicited" as used herein means elicitation of catalytic antibodies by haptens according to the invention through both in vitro and in vivo techniques. However, the skilled artisan will readily appreciate that when in vitro elicitation is involved, the haptens according to the invention, by themselves, may be used to elicit the catalytic antibodies. However, when elicitation is achieved through in vivo techniques, it is understood that immunogens comprising haptens complexed to a suitable carrier molecule are used to elicit the catalytic antibodies.

Another aspect of the invention is directed to a method for producing antibodies which can catalyze a chemical reaction of interest and which are elicited through in vitro or in vivo techniques by an antigen. The antigen comprises a hapten according to the invention. The haptens are designed to elicit the appropriate hypervariable binding region in an antibody molecule to express intrinsic binding energy for the transition-state of a chemical reaction, particularly a hydrolytic reaction. Arrangement of amino-acid side chains generated in the combining-site will be appropriate for performing chemical modification of an epitope of interest. Additional improvements in catalytic efficiency can be achieved by site-directed mutagenesis.

Broadly, the method comprises exposing cells capable of producing antibodies to the antigen and thereby generating antibody producing cells; hybridizing the antibody producing cells with myeloma cells and thereby producing a plurality of hybridoma cells each producing monoclonal antibodies; and screening the plurality of monoclonal antibodies to identify a monoclonal antibody which catalyzes the chemical reaction of interest. The monoclonal antibody so identified may then be replicated, again by either in vivo or in vitro techniques, to obtain a quantity sufficient to catalyze the chemical reaction of interest.

The detection of antibodies with the desired catalytic activity and specificity is achieved by screening the hybridomas once they have been elicited. For example, screening may be achieved by high performance liquid chromatography (HPLC) or spectrophotometric methods (ELISA).

Catalytic monoclonal antibodies are elicited "in vivo" by modification of the technique disclosed by Koprowski et al. in U.S. Pat. No. 4,196,265, issued Apr. 1, 1980, which is hereby incorporated by reference. The details of that process are known in the art. A series of monoclonal antibodies directed to a specific molecule are prepared under suitable conditions. This involves first immunizing BALB/C mice with an appropriate antigen. The antigen comprises a hapten according to the invention bound to a peptide or other carrier molecule.

Antibody-producing lymphocytes are then removed from the spleens of the immunized mice and hybridized with myeloma cells such as SP2/0 cells to produce hybridoma cells. These hybridoma cells are then plated in the wells of microtiter plates. The series of monoclonal antibodies being produced by the hybridoma cells is screened under appropriate conditions to identify monoclonal antibodies which catalyze the desired reaction under appropriate conditions. Screening may be conveniently accomplished by treating a standardized solution of the reactant with an aliquot of medium withdrawn from a microtiter well and measuring the presence of the desired product by conventional instrumental methods. This measurement may be readily conducted, for example by spectrophotometric methods or by gas-liquid or high pressure liquid chromatography. By comparison with standardized samples of the desired product or reactant, rates of reaction may be quantified. In this manner, wells containing hybridoma cells producing catalytic monoclonal antibodies are identified. The selected hybridoma cells are then cultured to yield colonies.

These colonies may be further propagated in in vitro or in vivo systems. In the latter case, mice such as syngeneic BALB/C mice are inoculated intraperitoneally with the selected hybridoma cells and produce tumors, generally within two or three weeks. These tumors are accompanied by the production of ascites fluid which contains the desired monoclonal antibodies. The monoclonal antibodies are then separately recovered from the ascites fluid by conventional methods such as ultrafiltration, ultracentrifugation, dialysis and immunoaffinity chromatography.

The invention is also a method for catalyzing the cleavage or formation of a peptide linkage or an ester bond in a molecule. Target molecules include bimolecules such as proteins, lipids, etc. The method comprises contacting a molecule containing one or more peptide linkages or ester bonds with an effective amount of a catalytic antibody which has been elicited by an antigen comprising a hapten of the invention.

In accordance with the invention, the separately recovered monoclonal antibodies are contacted with a molecule under suitable conditions permitting the formation of a complex between the monoclonal antibody and the molecule. In general, the concentration of the catalytic antibodies used is less than the equivalent concentration of the target molecule and may be in the picomolar range. The antibodies should function under normal physiologic conditions in vivo. The skilled artisan will appreciate that the conditions suitable for complex formation may vary depending on the particular molecule and monoclonal antibody under consideration. Accordingly, the methods of this invention may be practiced under a variety of reaction conditions, in vivo and in vitro, as long as the monoclonal antibodies are not prevented from complexing with the molecules or otherwise rendered inactive. More specifically, suitable conditions for complex formation encompass solution phase and emulsion reaction systems including a protic solvent, preferably water, maintained at a pH value between about 6.0 and about 8.0, preferably between about 6.0 and about 7.5 and at a temperature from about 4° C. to about 50° C., preferably from about 20° C. to about 45° C. The ionic strength, $\mu = \frac{1}{2}\Sigma c_i z_i^2$, where c is the concentration and z is the electronic charge of an ionic solute, should be maintained at a value below about 2.0 moles/liter, preferably between 0.1 and 1.5 moles/liter. The method of this invention may be carried out at reduced or elevated pressure, but preferably is practiced at ambient pressure. In addition to solution phase and emulsion reaction systems, suitable conditions also include the use of support materials to which the monoclonal antibody is attached. Such support materials are well-known to those of ordinary skill in the art as are methods for attaching monoclonal antibodies to them.

Catalytic antibodies elicited with the antigens of the invention may be useful in the treatment of autoimmune disease, cancer and thrombolytic disease. The catalytic antibodies may also be useful for treatment of cardiovascular disease eliminating high density lipoproteins and for the detoxification of bacterial endotoxins.

Vaccines comprising synthetic peptides optionally linked to carrier proteins, for example, against foot and mouth disease (FMD) and *E. coli* enterotoxin, have been proven efficacious in recent years.

Oligo peptides having variable lengths with sequences from the receptor-binding regions of viruses which employ a specific cellular receptor for penetration of the host cell and having a transition state analog dipeptide isostere in a critical region of the sequence induce on immunization, optionally after coupling to a suitable carrier protein, catalytic antibodies that cleave the viral coat protein and prevent virus penetrating the cell. The dimensional structure of Rhino 14 and Polio 1 virus particles has been charted by X-ray scattering. Regions have been identified which are binding sites to cellular receptors. The region of the human immunodeficiency virus type 1 (HIV I) critical for interaction with the CD4 receptor on T-lymphoytes has been located and mapped to sequences in the gp120 goat protein.

Thus, in one embodiment of the invention, oligo peptides are used which contain partial sequences from the envelope proteins of viruses critical for host cell attachment and a transition-state dipeptide isostere selected from the haptens according to the invention. The resultant peptide analogs are used to induce catalytic antibodies that inactivate viruses by proteolysing segments (epitopes) of the viral coat protein critical for infectivity.

Preferably, oligopeptides are used having sequences from the receptor binding region of retroviruses e.g., HIV I, and picorna viruses, e.g., Rhino 14.

The invention will be more fully described and understood with reference to the following non-limiting examples.

EXAMPLE 1

Synthesis of Aminomethanesulfonamidylalanyl Acid

The reaction sequence is shown in FIG. 12.

Preparation of Silver Salt of N(-Benzyloxycarbonyl)glycine (I)

2.09 g (10 mmol) of N(-benzyloxycarbonyl) glycine is dissolved in 16.8 ml of 5% sodium hydrogen carbonate. After removing the carbon dioxide by evacuation (two minutes on rotavapor) 1.70 g (10 mmol) of $AgNO_3$ in 15 ml water is added to the above stirred solution in the dark. After 15 minutes the white precipitated material is filtered at 10° C., washed with ice water, acetone and anhydrous $CCl_4$. The salt is dried over $P_2O_5$ and $Mg_2SO_4$ in vacuum at 45° C. for 24 hrs. Yield 82%.

Preparation of 1-Bromo, 1-N-Benzyloxycarbonylmethane (II)

3.16 g (10 mmol) silver salt of N(-benzyloxycarbonyl) glycine (I) is stirred with 50 ml of $CCl_4$ in a flame-dried, round-bottomed flask under dry nitrogen. At 35–40° C., 20 ml $CCl_4$ solution of 12.5 mmol bromine is added dropwise over 5 minutes. The mixture is allowed to cool to room temperature, stirred for two hours, then filtered and concentrated in vacuo at room temperature to give a yellow-brown residue. The further precipitated material is filtered by using a mixture of methanol and dioxane. Neutralization of the solution is carried out at 0° C. with 5% ammonia in methanol. The refiltered solution is evaporated to give an oil. Yield 35%.

Preparation of Sodium 1-N-Benzyloxycarbonylmethanesulfonate (III)

7.32 g (30 mmol) of 1-bromo, 1-N-benzyloxycarbonylmethane (II) is added to a solution of 3.9 g (30 mmol) of sodium sulfite in 14 ml of water. The vigorously stirred mixture is boiled under reflux for 21 hours and then cooled to 20° to give a crystalline precipitate of sodium 1-N-Benzyloxycarbonylmethanesulfonate (III). The product is washed with ether, sucked dry and then dried under vacuum.

Preparation of 1-N-Benzyloxycarbonylmethanesulfonyl Chloride 5.34 g (20 mmol) of sodium 1-N-benzyloxycarbonylmethanesulfonate (III) is mixed with 1.67 g (8 mmol) of phosphorus pentachloride. After the initial exothermic reaction the stirred mixture is held at 25° C. for 4 hours. The reaction mixture is added, with vigorous stirring, to 150 g of ice and water, giving lumps of crude product, which are washed with cold water. Crystallization yields 1-N-benzyloxycarbonylmethanesulfonyl chloride.

Preparation of Nα-benzyloxycarbonyl)aminomethane-sulfonamidyl-alanyl Benzyloxy Ester (IV)

7.00 g (20 mmol) of L-alanine benzyl ester p-toluenesulfonate in 150 ml of $CH_2Cl_2$ is washed with 75 ml of 0.1 M NaOH. The $CH_2C_2$ layer is then washed with several portions of 100 ml of water until the aqueous washes become neutral. The organic layer is then dried (anhydrous $MgSO_4$), filtered and concentrated to a solid. The solid is then redissolved in 50 ml of $CH_2Cl_2$, 5.26 g (20 mmol) of 1-N-benzyloxycarbonyl-methanesulfonyl chloride is added followed by 2.2 ml (20 mmol) of N-methylmorpholine. The reaction mixture is stirred for 2 hours. More $CH_2Cl_2$ (50 ml) is added and the organic layer is washed with water, 1M citric acid, water, 1M $NaHCO_3$ and water. After drying (anhydrous $MgSO_4$), filtering and concentrating under vacuum, the product (IV) is obtained.

Preparation of Aminomethanesulfonamidylalanyl Acid (V)

8.12 g (20 mmol) of (IV) is dissolved in 100 ml of methanol. 1 g of 10% palladium on activated carbon is added and to this stirred mixture hydrogen gas is bubbled through. When the reaction is over, the mixture is filtered through a bed of celite, washed with 50 ml of methanol/water (9:1 v/v) and the collected filtrate and washings combined and concentrated under vacuum to give aminomethanesulfonamidylalanyl acid (V).

EXAMPLE 2

Synthesis of 3-(Aminomethyldihydroxysilyl) Propionic Acid

The reaction sequence is shown in FIG. 14.

Preparation of 3-(Trichlorosilyl) Propionic Acid Benzyl Ester (I)

A mixture of 244 g (1.5 moles) of vinyl benzyl ester, 203 g (1.5 moles) of trichlorosilane and 0.5 ml of 0.1 molar alcoholic chloroplatinic acid ($5 \times 10^{-5}$ mole) is refluxed for 24 hours. During this period the temperature of the refluxing mixture increases. The mixture is then distilled through a 22 mm×4 ft. Podbielniak column packed with Heli-pak to give 3-(trichlorosilyl) propionic acid benzyl ester (I).

Preparation of 3-(Dichloronitromethylsilyl) Propionic Acid Benzyl Ester (II)

298 g (1 mole) of 3-(trichlorosilyl) propionic acid benzyl ester (I) is dissolved in 540 ml (10 mol) of nitromethane and cooled to 0° C. Added dropwise 139 ml (1 mol) of triethylamine over a period of 2 hours. The mixture is then distilled through a 22 mm×4 ft. Podbielniak column packed with Heli-pak to give 3-(dichloronitromethylsilyl) propionic acid benzyl ester (II).

Preparation of 3-(Aminomethyldihydroxysilyl) Propionic Acid (III)

161 g (0.5 moles) of 3-(dichloronitromethylsily) propionic acid benzyl ester (II) is added dropwise to 200 ml of methanol-water (1:1 v/v) at 0° C. over a 30 minute period. The solution is flushed with nitrogen, 10 g of 10% palladium on activated carbon is added and hydrogen gas is passed through the stirred mixture until all the substance is converted to product. The mixture is filtered through celite (100 g) and washed with 50 ml methanol-water (1:1 v/v). The filtrate and washings are combined and then concentrated under vacuum to yield 3-(aminomethyl dihydroxysilyl) propionic acid (III).

EXAMPLE 3

Synthesis of (S)-Lactate-1-(R)-Amino-2-Phenylethane Boronate

The reaction sequence is shown in FIG. 15.

Preparation of (+)-Pinanediol (R)-1-Benzyloxycarbonylamino-2-phenylethane Boronate (IV)

Lithium diisopropylamide (12 mmol)) in hexane is fluidized with a little THF and added dropwise to 0.27 g (10 mmol) of (+)-pinanediolbenzylboronate (I) (Bp 108° C. (0.1 torr), $[\alpha]_D^{22}$+31.30° (c18, toluene) and 1 ml dichloromethane in 10 ml dimethoxyethane at −78° C. After 1 hr. at 0° C. the mixture is cooled to −78° C. and lithiohexamethyldisilizane (10 mmol) in THF is added. This mixture is kept overnight at 20° C. After cooling to −78° C. 7.47 g (30 mmol) of N-(benzyloxycarbonyloxy) succinimide and 0.77 ml (10 mmol) of $CF_3CO_2H$ are added. The reaction is kept at 20° C. for 15 hrs. and then isolated by chromotography, using silica gel and eluting with ether, and recrystallized three times with $CH_2Cl_2$ to give (+)-pinanediol (R)-1-benzyloxycarbonylamino-2-phenylethane boronate (IV).

Preparation of (R)-1-Benzyloxycarbonyl-amino-2-phenylethane Boronic Acid (V)

To a solution of 2.93 g. (7 mmol) of (+)-pinanediol-1-benzyloxycarbonylamino-2-phenylethane boronate (IV) in 20 ml of $CH_2Cl_2$ at −78° C. is added 24 ml of boron trichloride. The mixture is kept at 20° C. for 2 hrs., then concentrated under vacuum and the residue is washed with ether, treated with methanol, concentrated and dissolved in water. The solution is then neutralized with Dowex 1-x8 ion exchange resin bicarbonate, concentrated and crystallized from THF/water to give (R)-1-benzyloxycarbonylamino-2-phenylethane boronic acid and its anhydride.

Preparation of (S)-Lactate-1-(R)-amino-2-phenylethaneboronate (VIII)

1.42 (5 mmol) of (R)-1-benzyloxycarbonylamino-2-phenylethane boronic acid (V) is refluxed with 80 ml of benzene and 0.45 g (5 mmol) of (S)-(+)-lactic acid (VI) in a Dean Stark apparatus for 5 hrs. After cooling the mixture is concentrated, redissolved in 75 ml of methanol and then transferred to a two-necked flask. The mixture is flushed with nitrogen, 1 gram of 10% palladium on activated carbon is added and hydrogen gas is passed through the stirred mixture for 2 hrs. 75 ml of methanol-water (1:1 $^v$/v) is added and the mixture filtered slowly through celite (30 g). The filtrate is collected and concentrated to give (S)-lactate-1-(R)-amino-2-phenylethane boronate (VIII).

EXAMPLE 4

Synthesis of (R)-2-Hydroxymethyl-2-Hydroxy-Propanoic Acid Diol 1-Amino-2-Phenylethaneboronate The reaction sequence is shown in FIG. 16.

Preparation of (+)-Pinanediol 1-Fluoroacetamido-2-Phenylethaneboronate (IV)

Lithium diisopropylamide (12 mmol) in hexane is fluidized with a little THF and added dropwise to 0.27 g (10 mmol) of (+)-pinanediol-benzylboronate (I) (Bp 108° C. at 0.1 torr; $[\alpha]_D^{22}$+31.30° (c18, toluene)) and 1 ml dichloromethane in 10 ml dimethoxyethane at −78° C. After 1 hr. at 0° C. the mixture is cooled to −78° C. and lithiohexamethyldisilizane (10 mmol) in THF is added. This mixture is kept overnight at 20° C. After cooling to −78° C. 4.2 ml (30 mmol) of $(CF_3CO)_2O$ and 0.77 ml (10 mmol) of $CF_3CO_2H$ are added. The reaction is kept at 20° C. for 15 hrs. and then isolated by chromatography, using silica gel and eluting with ether, and recrystallized three times with $CH_2Cl_2$ to give (+)-pinanediol 1-fluoroacetamido-2-phenylethaneboronate (IV).

Preparation of 1-Fluoroacetamido-2-Phenylethaneboronic Acid (V)

To a solution of 2.66 g (7 mmol) of (+)-pinanediol 1-fluroroacetamido-2-phenylethaneboronate (IV) in 20 ml of $CH_2Cl_2$ at −78° C. is added 24 ml of boron trichloride. The mixture is kept at 20° C. for 2 hrs., then concentrated under vacuum and the residue is washed with ether, treated with methanol, concentrated and dissolved in water. The solution is then neutralized with Dowex 1-x8 ion exchange resin bicarbonate, concentrated and crystallized from THF/water to give 1-fluoroacetamido-2-phenylethaneboronic acid (V) and its anhydride.

Preparation of (R)-2-Hydroxymethyl-2-Hydroxy-Propanoic Acid Diol 1-Amino-2-Phenylethaneboronate (VIII)

1.30 (5 mmol) of 1-fluoroacetamido-2-phenylethane-boronic acid (V) is refluxed with 40 ml benzene, 40 ml ethanol and 1.8 g (15 mmol) of (R)-2-(carboxymethyl)-2-hydroxypropanoic acid in a Dean Stark apparatus for 5 hrs. After cooling, the mixture is concentrated and then redissolved in 40 ml of 0.5M ammonia in methanol. After two hours standing at 20° C., the solution is concentrated, redissolved in methanol and concentrated again.

EXAMPLE 5

Synthesis of 5-(Serinyl)amino 3,3-difluoro 4-oxo 6-hydroxy Heptanoic Acid (VII)

The synthesis of compound (VII) is shown schematically in FIG. 13.

Preparation of 2,2-Difluoro-4-pentenoic Acid (II)

A 250 ml, three-necked flask equipped with a magnetic stir bar, a low-temperature thermometer, a condenser filled with dry ice/acetone, and a balloon is charged with dry THF (100 mL). The flask is cooled to approximately −50° C. and tetrafluoroethylene is passed through a tube of silica and then through a needle into the THF until saturation is reached (as judged by inflation of the balloon). The flask is allowed to warm to −5 to −10° C. which causes the balloon to inflate slightly (most of the gas will be trapped by the condenser). To a separate 50 ml. flask is added NaH (100 mg, 4.2 mmol, 80% suspension in oil), and the oil is removed by repeated washing with dry THF under argon. A solution of previously distilled allyl alcohol (3.0 g 52 mmol) in dry THF (2 ml) is slowly added by syringe with stirring and the mixture is allowed to stir for an additional 10 min. This solution is then transferred dropwise by syringe to the three-necked flask with stirring at −5 to −10° C. After approximately 3 hr, the reaction is checked by GC (60° C.) of a small aliquot and, if needed, additional tetrafluoroethylene is bubbled into the solution for about 5 min. The product elutes just after the allyl alcohol. Further additions of tetrafluoroethylene are usually required. The addition reaction usually requires 6 hr. The reaction is then placed under argon, cooled to −60° C. and n-butyllithium (one equivalent in hexane) is added dropwise over 2 hr. from an addition funnel while the temperature is kept constant at −60° C. The mixture is cooled to −78° C., water (2 ml) is added, the cooling bath is removed and the solution is stirred overnight. The solution is basified with aqueous NaOH and the solvent removed in vacuo. The residue is acidified with 1N HCl and extracted three times with ether. The organic layers are combined and extracted with saturated NaHCO$_3$. The aqueous extract is acidified to pH 1 with HCl and extracted three times with ether. The presence of the difluoro acid is confirmed by NMR of a small aliquot.

Preparation of 2,2-Difluoro-4-pentenoic Acid Anhydride (III)

A suspension of silver oxide in water is prepared by adding a solution of NaOH (1.76 g, 0.044 mol) in water (100 ml) to an aqueous solution of silver nitrate (7.14 g, 0.042 mol in 100 ml), decanting the supernatant liquid, washing the residue with water (3×100 ml) and adding 100 ml of water. To this vigorously stirred suspension is added a solution of 2,2-difluoro-4-pentenoic acid (III) (5.44 g, 0.04 mol) in water (100 ml). After 10 minutes the mixture is filtered and the filtrate concentrated (20 Torr, 30° C.) to afford a solid residue which is dried over phosphorus pentoxide (0.05 Torr, 50° C., 24 hours) to give 8.4 g (87%) of silver 2,2-difluoro-4-pentenoate as a white amorphous powder. A suspension of 7.3 g (0.03 mol) of the silver salt in 50 ml of dichloromethane is stirred under nitrogen, cooled to 0° C. and then 1.9 g (1.3 ml, 0.015 mol) of oxalyl chloride is added slowly. The cooling bath is removed and the reaction mixture allowed to warm up to room temperature. Heating to 40° C. for 30 minutes completes the reaction. After cooling to room temperature, the supernatant liquid is decanted and the residue washed with dichloromethane (2×5 ml). The organic layers are combined and the solvents removed by distillation at atmospheric pressure. The so-obtained oily residue is then purified by distillation yo yield 2.85 g of very hydroscopic 2,2-difluoro-4-pentenoic acid anhydride III, bp 78–80° C./20 Torr.

Preparation of 6-[N-α-(tert-butyloxycarbonyl)-O-(tert-butyl)serinyl-O-(tert-butyl)threoninyl] amino 4,4 Difluoro 5-oxo-7-tert-butyloxy 1-octene (IV)

0.786 g of Z-Ser(t-Bu)-Thr(t-Bu)-OH (1.74 mmol) (which is synthesized by methods well known in the art) is added to 0.965 g of 2,2-difluoro-4-pentenoic acid anhydride (III) (3.8 mmol). 0.35 ml of Et$_3$N (2.61 mmol) is added followed by 9 mg of DMAP (0.073 mmol). The mixture is stirred in a water bath at 50° C. for one hour. The Et$_3$N is evaporated in vacuo and the residue is stirred with 10 ml of 5% NaHCO$_3$ for 30 min. The product is extracted into ethyl acetate and washed with 0.1M acetic acid and brine. The ethyl acetate solution was dried over MgSO$_4$, filtered and evaporated to give an oily residue. Purification is achieved using flash chromatography on silica gel to give Z-Ser(t-Bu)-Thr(t-Bu)C(O)CF$_2$CH$_2$CH=CH$_2$ (IV).

Preparation of 5-[Nα-(tert-butyloxycarbonyl)-O-(tert-butyl)serinyl-O-(tert-butyl)threoninyl] amino 3,3-difluoro 4-oxo 6-tert-butyloxy Heptanoic Acid (V)

A solution of 0.516 g of compound (IV) (1 mmol) in dichloromethane (40 ml) is treated with O$_3$ at −78° C. for 12 minutes (about 1.2 mmol O$_3$). 0.4 ml of dimethylsulfide (6.6 mmol) is added and the solution is allowed to warm to room temperature. After removal of solvents (20 Torr, 30° C. and 0.05 Torr, 30° C.) an oil is obtained. A solution of the oil in acetone (1.5 ml) is treated with a Jones-solution (1.5 ml, 1M CrO$_3$/H$_2$SO$_4$) overnight. The organic layer is separated and the aqueous phase extracted with ethyl acetate (4×2 ml). The combined organic layers are washed with brine, dried (MgSO$_4$) and evaporated to give compound (V).

Preparation of 5-[Nα-(9-fluoroenylmethoxycarbo-
nyl)-O-(tert-butyl)serinyl-O-(tert-butyl)threoninyl]
amino 3,3-difluoro 4-oxo 6-tert-butyloxy Heptanoic
Acid (VI)

0.40 g of compound (V) (0.75 mmol) is dissolved in 10 ml of methanol. 0.10 g of 10% palladium on activated carbon is added and to this stirred mixture hydrogen gas is bubbled through. After two hours the mixture is filtered through a bed of celite, washed with 5 ml of methanol-water (9/1) and the collected filtrate and washings combined and concentrated in vacuum to a solid. 4 ml of 10% $Na_2CO_3$ is added to the solid and the solution cooled in an ice bath. 0.233 g of 9-fluorenylmethyl chloroformate (0.9 mmol) in 3 ml of dioxan is added dropwise over 15 minutes to the above stirred solution. After the addition the mixture is stirred for two hours. 30 ml of $H_2O$ is added and the aqueous mixture is washed with diethyl ether (3×20 ml). The aqueous layer is then acidified to pH 3 with 0.1M HCl and extracted with ethyl acetate (3×20 ml). The combined organic layers are dried ($MgSO_4$) and evaporated to give compound (VI). Compound (VI) is then fully deprotected to yield compound (VII).

EXAMPLE 6

Methodology for the Production, Screening and Isolation of Monoclonal Catalytic Antibodies that Cleave the "Flap" Region of Human Renin.

The inhibition of renin, an aspartic proteinase whose action initiates the renin-angiotensin cascade has been the object of intense investigation in recent years. The potential for treatment of hypertension through the inhibition of renin has resulted in the synthesis of a variety of potent renin inhibitors based on the peptide sequence of the natural substrate angiotensinogen. An alternative approach is the use of a proteolytic antibody to renin.

It has been reported that the flap region of human renin is a hairpin with a loop region of four amino acid residues leading to the carbonyl group of Tyr 83 interacting with the amino groups of Thr 85 and Gly 86 (32). The cyclic decapeptide $$\overline{\text{CLRYSTGTVC}},$$

[80–89] human renin, was found to adopt this same hairpin structure.

In this example, monoclonal antibodies are elicited with a diflurokotone containing immunogen according to the invention. The monoclonal antibodies will catalyze the cleavage of the peptide sequence

```
        81          85 86          90
    Leu-Arg-Tyr-Ser-Thr-Gly-Thr-Val-Ser-Gly
``` in the human renin molecule between residues 85 and 86. Cleavage causes disruption of the catalytic machinery of the enzyme since residues 85 and 86 constitute the "flap" region which holds the substrate in the catalytic site (33). It has previously been demonstrated that rabbit polyclonal antiserum elicited to a synthetic peptide fragment (sequence 81–90) could inhibit human renin activity by 40% as measured by its reaction with synthetic human tetradecapeptide substrate (34).

In order to raise a catalytic antibody to this flap region of human renin, the cyclic peptide hapten $$\overline{\text{CLRYST(TS)GTVC}},$$

where (TS) represents the transition state analog, is synthesized. In this example, the synthesis of the cyclic peptide hapten CLRYST(TS)GTVC follows the solid-phase approach (35) wherein ST(TS)G corresponding to the transition state analog tripeptide isostere (VII), whose synthesis is decribed in Example 5, is incorporated into the assembled peptide through its anhydride (35). The completed peptide is fully deprotected and cleaved from the solid support using trifluoroacetic acid.

Cyclization of the peptide is achieved by allowing the peptide to stand at low concentration for one hour in an aqueous solution (pH 8) in order to generate a disulphide bridge between the two terminal cysteine residues. The N-terminal amino group of the peptide allows it to be attached to a carrier protein for immunization of mice.

A. Preparation of the Immunogen

1. Peptide Synthesis

The peptide hapten is synthesized by the solid phase technique using the polyamide-Kieselguhr composite resin (35). The side chain protecting groups are the following: O-tert-butyl (tyrosine, glutamic acid, serine, threonine); N-4-methoxy-2,3,6-trimethyl benzenesulphonyl (arginine); and S-trityl (cysteine). The temporary protection of the N function is by fluorenylmethoxycarbonyl which is removed in 10 minutes with piperidine/DMF:20/80. The coupling reactions are carried out using FMOC-amino acid anhydrides (35). The protected peptidyl-resin is fully deprotected by treatment with trifluoroacetic acid/thioanisole/m-cresol/thiophenyl/ethanedithiol solution: 90/2/2/2/4 for 3 hrs. After filtration the filtrate is concentrated under vacuum to a small volume. Ether is added to give a precipitate of the peptide. The ethereal supernatant is removed and the peptidic precipitate is washed twice with ether to yield the peptide hapten

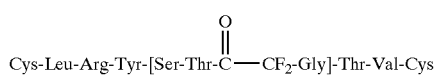

wherein the bracketed moiety is the difluoroketone transition state analog tripeptide isostere of Example 5.

2. Cyclization of Peptide Hapten

The peptide hapten is cyclized to obtain the "β-hairpin" conformation by forming a disulphide bond between the two terminal cysteine residues. The disulfide bond is completed in one hour by air oxidation of an aqueous solution (pH 8) at a concentration of 0.3 mg of peptide per milliliter. The oxidized product is then removed by lyophilization and purified by HPLC.

3. Conjugation of the Hapten to the Carrier Molecule

The cyclic peptide hapten

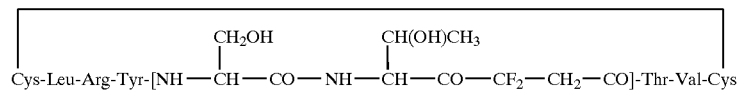

is conjugated to keyhole limpet hemocyanin (KLH) using glutaraldehyde (36). Coupling efficiency is 50–80% as estimated by binding of a trace amount of $I^{125}$ peptide added to the reaction mixture.

B. Preparation and Screening of Monoclonal Antibodies

KLH conjugated peptide (50 µg) in complete Freund's adjuvant is injected into BALB/c mice. Hybridoma fusions are carried out by standard methods using SP2/0 myeloma as the fusion partner. Polyclonal antiserum response and hybridoma secreting cells resulting from the fusion are screened for binding activity by ELISA.

Wells of plastic microtiter plates (Falcon 3915 Probind, Becton Dickinson Labware CA, USA) are coated with 50 uL of peptide (5 µg/mL) in Tris-HCl buffer (0.1 M, pH 9.6).

Plates are first incubated for 30 minutes at 37° C. and then overnight at room temperature. After washing three times with Tween-containing phosphate-buffered saline. (PBS-Tween 0.1%, pH 7.4), 50 µL of serial dilutions of antisera in PBS-BSA 1% pH 7.4 are added in peptide-coated duplicate wells and incubated for 2 hours at 37° C. Plates are washed three times again with PBS-Tween 0.1% and wells are then treated with 50 uL of alkaline phosphatase-labelled goat anti-mouse IgG diluted 1:500 (Sigma, Mo., USA). Incubation is carried out for 1 hour at 37° C.

Additional extensive washing with PBS-Tween 0.1% is followed by incubation with 150 uL of alkaline phosphatase substrate (2 tablets/10 ml of Sigma 104–105) dissolved in 0.1 M glycine-NaOH buffer (pH 10.4) containing $MgCl_2$ and $ZnCl_2$, 1M/L. The enzymatic reaction is allowed to proceed for 2 hours at 37° C. and stopped by addition of 50 uL of $Na_2CO_3$ (1.5 M).

Absorbance is read at 405 nm in a Titerteck multiskan ELISA reader (Flow laboratories). Titer expression is determined by multiplying the optical density by the maximal dilution giving an absorbance three times as high as the negative control (consisting of pooled normal mouse sera diluted 1:100).

Hybridomas giving a positive reaction in this screening assay are chosen for further study. IgG is purified from ascites fluid by HPLC with a Bakerbond $AB_x$ HPLC column.

C. Catalysis of Peptide Cleavage by Catalytic Antibody Specific for the "Flap" Region of Human Renin.

The decapeptide substrate $H_2N$-Leu-Arg-Tyr-Ser-Thr-Gly-Thr-Val-Ser-Gly-$CO_2H$ (2.7 µM) is incubated with the catalytic antibodies produced by the procedure outlined above and the reaction monitored by reverse phase HPLC analysis of the mixture. The reaction is carried out at pH values optimal for high $K_{cat}$ by the catalytic antibody (optimum pH is determined employing the chromogenic p-nitroanilide substrate

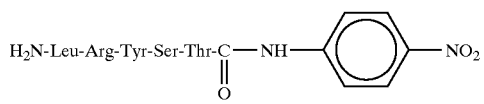

or the fluorescent coumarin substrate

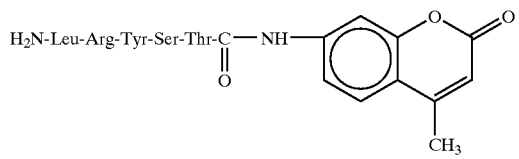

and taking into account the binding energy of the catalytic antibody for the residues on the C-terminal side of the cleavage site with change in pH).

Antibodies that show the best $K_{cat}$ values for cleavage of the decapeptide substrate are tested for their ability to inhibit human renin.

D. Binding of Anti-Transition-State Analog Antibodies to Human Renin and Inhibition of its Enzymatic Activity by Cleavage of Residues 85–86 in the "Flap" Region.

Inhibition of plasma renin activity—the ability of the catalytic antibodies to inhibit renin activity—is tested on a pool of human plasma having a high renin activity (40 ng of angiontensin I/h/mL). Plasma (25 ul) is pre-incubated with 100 ul of the catalytic antibody in PBS (pH 7.5) containing 1% EDTA (final volume 0.2 mL) for various periods of time. Next, an excess of plasma renin substrate (200 pmol) is added in order to ensure zero-order behavior, and the mixture is incubated for 30 min. at 37° C. in PBS (pH 5.7). The final dilution of the catalytic antibody is 1:5 and 1:50. The angiotensin I generated is measured by radioimmunoassay (37). A blank is included using the same dilutions of the corresponding abzymes.

The amount of angiotension I generated is less than that observed with intact renin, thus indicating cleavage of residues 85–86 in the "flap" region and inhibition.

EXAMPLE 7

In Vivo Preparation of Immunogenic Transition-State Analog Containing Peptide from HIV gp120 Coat Protein The octapeptide sequence -Ala-Ser-Thr-Thr-Thr-Asn-Tyr-Thr- from HIV gp120 coat protein is important for virus interaction with the $OKT_4$ antigen of T4 helper/inducer cells. Synthetic peptides identical or very similar in sequence to this octapeptide strongly inhibit attachment of HIV to the antigen receptor (38). Computer assisted searches have demonstrated homology to a peptide found in the envelope region of the Epstein-Barr virus. In addition, strong homologies exist between the HIV octapeptide and peptides which occur in human lymphoadenopathy virus (LAV) and in human T-cell leukemia virus (HTLV-IIIb) isolates.

An additional homology exists between the HIV peptide and a sequence comprising residues 19–26 of bovine pancreatic ribonuclease A (RNase A). This sequence contains the exposed subtilisin cleavage sites of RNase A between residues 20 and 21 and 21 and 22 (39).

Peptide haptens according to the invention are:
(1)-Ala-[Ser-A-Thr]-Thr-Thr-Asn-Tyr-Cys
(2)-Ala-Ser-[Thr-A-Thr]-Thr-Asn-Tyr-Cys
(3)-Ala-Ser-Thr-[Thr-A-Thr]-Asn-Tyr-Cys
(4)-Ala-Ser-Thr-Thr-[Thr-A-Asn]-Tyr-Cys The transition state dipeptide isosteres (indicated in brackets) wherein A represents the tetrahedral array of atoms as described earlier are incorporated into the peptides as described in Example 6. Each peptide hapten is coupled with keyhole limpet hemocyanin (KLH) carrier protein through the terminal cysteine residue utilizing the cross-linker m-maleimidobenzoyl-N—hydroxysuccinimide ester (40).

B. Preparation of Monoclonal Antibodies

BALB/C mice are immunized with the KLH-peptide analog conjugates emulsified in complete Freund's adjuvant. A blood sample is obtained from each mouse and the serum separated by centrifugation and stored at 4° C. Sera obtained in this way are screened for binding activity to the original transition-state analog immunogen by standard ELISA procedures. Antibody producing mice immunized as described above and assayed for reactivity with the transition state analog peptide immunogens are sacrificed and their spleens removed and hybidoma cells are prepared using SP2/0 myeloma cells as described in Example 6B above.

C. Screening Hybridoma Cells Producing Catalytic Monoclonal Antibodies

Screening for binding of antibodies to respective transition state analog-containing peptides is performed essentially as described in Example 6 above. Hybridomas secreting monoclonal antibodies and giving a positive binding reaction are chosen for further study. IgG is purified from ascites fluid by HPLC with Bakerbond $AB_x$HPLC.

EXAMPLE 8

In Vitro Elicitation of Catalytic Monoclonal Antibodies Against a Viral Epitope that Selectively Inhibits Human Immunodeficiency Virus (HIV)

A. Preparation of the Immunogen

The dipeptide transition state isostere, 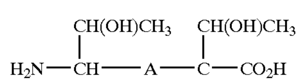 wherein A is as hereinbefore described, is incorporated into a peptide as described in Example 6 to give the hapten 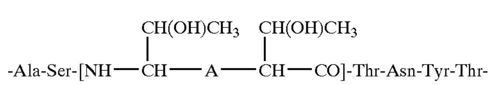 The resulting hapten is designed to mimic a portion of the HIV gp120 goat protein. The synthetic peptide is used in an in vitro immunization procedure using a modification of a literature procedure (41). Spleen cells are cultured at $10^6$ cell/ml in a medium consisting of 50% fresh Eagle's MEM with 20% fetal bovine serum $5\times10^{-5}$M β-mercaptoethanol, 2 mM glutamine and 50% conditioned medium from BALB/c mouse thymocytes. To furnish conditioned medium, thymocytes are cultured at 3–$5\times10^6$ cells/mL in the same Eagles MEM medium as above. After 48–72 hours the medium is removed, sterilized by filtration and used immediately for in vitro activation. The antigen is added to the spleen cell culture medium at concentrations equivalent to approxamately 1 ug peptide/ml. Spleen cells are cultured in the presence of antigen for four days without a change in the medium and are later hybridized.

Hybridizidations are carried out with the mouse plasmacytoma cell line 45 6TGL.7 (42) obtained from the Cell Distribution Center of the Salk Institute. Spleen cells (either freshly isolated or from in vitro activation cultures) and plasmacytoma cells are washed twice in serin-free Eagles MEM, then fused using PEG 1000 as previously described in the literature (43). Hybrids are selected by treatment of the cultures with HAT (44). Hybrid cells which produce antibody reactive with the peptide transition state analog (as judged by an ELISA assay) are cloned and re-cloned by limiting dilution in conditioned medium from parental plasmacytoma cells.

Screening for binding of antibodies to respective transition state analog-containing peptides is performed essentially as described in Example 6 above. Hybridomas secreting monoclonal antibodies giving a positive binding reaction are chosen for further study. IgG is purified from ascites fluid by HPLC with Bakerbond $AB_x$ HPLC.

The virus replication assay is carried out essentially as described in the literature (45), except that cultures are propagated in microtube wells containing 200 μL. Graded concentrations of purified antibodies obtained from the in-vitro immunization procedure or buffer alone, each in 25 uL, are preincubated for 1 hr. at 37° C. in 5% $CO_2$ with 50 $TCID_{50}$ HTLV-IIIB in 25 μL. Following preincubation, H9 cells ($1\times10^5$ cells in 150 μL RPM1-040 supplemented with 20% heat-inactivated FCS) are added to the wells, yielding final antibody concentrations ranging from 0.1 $\mu gml^{-1}$ to 10 $\mu gml^{-1}$. Microtiter plates are incubated at 37° C. in 5% $CO_2$ for 14 days. Cells are fed by exchanging 100 μL cell-free supernatant fluid on days 3, 7 and 10 with fresh medium, and no further antibody is added during this period. Cell-free supernatant fluid (100 μL) is analyzed for p24 antigen by RIA (Dupont, NEK-040).

The C8166 fusion assay is described in the literature (46). Three monoclonal antibodies (clone AHIV1.6; AHIV1.3 and AHIV2.0) are tested in 2 hr. assays. H9 cells ($1\times10^4$) infected chronically with HTLV-IIIB are preincubated with varying concentrations of antibody in 150 uL medium in 96-well plates. All assays are done in triplicate. After 1 hr. incubation at 37° C. in 5% $CO_2$, $3\times10^4$ C8166 cells (HTLV-I transformed umbilical cord lymphocytes) in 50 uL are added to the wells. Final well concentrations of antibodies are 41 $\mu gml^{-1}$ and 5 $\mu gm^{-1}$. Preincubation with OKT4A (Ortho Diognostics) at 25 $\mu gml^{-}$served as a control. After the plates are incubated for 2 hrs. at 37° C. in 5% $CO_2$, syncytia (ballooning cytoplasm greater than three lymphocyte cell diameters) are counted. To prevent bias during counting, samples are coded.

The antiviral activity of clones AHIV 1.3, AHIV 1.6 and AHIV 2.0 is examined in HIV-I replication and cell fusion assays. FIG. 23 shows the dose dependent inhibition by clone AHIV 1.3 of HIV-1 p. 24 gag production in infected H9 cells. FIG. 24 shows the dose dependent inhibition by clones AHIV 1.3, AHIV 1.6 and AHIV 2.0 of HIV-induced cell fusion.

The catalytic monoclonal antibodies elicited by in vitro immunization with the transition state dipeptide isostere analog incorporated into the exposed peptide sequence of HIV gp120 can prevent infection by HIV virus by causing rupture of an important region of the viral coprotein involved in binding to the CD4 receptor on lymphocytes. The catalytic monoclonal antibodies break the peptide bond in the chosen sequence (i.e., between the first two threonine residues from the left of the octapeptide shown in Example 7) in a manner analogous to the action of proteolytic enzymes. The mechanism of the antibody catalyzed hydrolysis of the octapeptide does not involve a metal ion and consequently may involve either a nucleophile in the active site of the antibody or nucleophilic addition of water activated by amino acid residues in the antibody combining site.

EXAMPLE 9

Site Specific Cleavage of the Threonine-Glycine Bond, Residues 9 and 10, in a Tetradecapeptide Containing Two Other Threonine-Glycine Bonds, Residues 4, 5 and 12, 13

In this example, catalytic antibodies are elicited for the purpose of cleaving the threonine-glycine bond at residues 9 and 10 in a tetradecapeptide containing two other threonine-glycine bonds, one at residues 4 and 5 and the other at residues 12 and 13.

Catalytic antibodies are elicited by the methodology described in Example 6 to the tetradecapeptide immunogen: Ala-Val-Leu-Thr$^4$-Gly$^5$-Ala-Val-[Ser-Thr$^9$-T.S.-Gly$^{10}$]-Tyr-Thr$^{12}$-Gly$^{13}$-Val. The tripeptide transition state analog isostere,

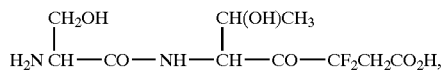

represented in the immunogen by [Ser-Thr-T.S.-Gly] and synthesized as described in Example 5, is incorporated into the assembled peptide through its anhydride, as described in Example 6, to yield the tetradecapeptide immunogen shown above.

Antibodies isolated from ascites fluid by Ab$_x$ HPLC chromatography and identified as being specific for the tripeptide transition state analog isostere in the tetradecapeptide immunogen are incubated for approximately one hour at 37° C. with the tetradecapeptide substate: Ala-Val-Leu-Thr-Gly-Ala-Val-Ser-Thr-Gly-Tyr-Thr-Gly-Val.

The reaction mixture is then analyzed by HPLC. Acetic acid (3M) is added and the samples are centrifuged for 10 minutes. An aliquot of the resulting supenatant is analyzed by HPLC using a Vydac C-18 analytical column. Absorbance at 214 nm is monitored and fractions are collected. Resultant peptide fractions are analyzed by standard amino acid analysis and sequencing. Analysis of the cleavage products from the action of the catalytic anti-transition-state analog antibodies shows that two peptide fragments, a nonapeptide, H$_2$N-Ala-Val-Leu-Thr-Gly-Ala-Val-Ser-Thr-CO$_2$H, and a pentapeptide, H$_2$N-Gly-Tyr-Thr-Gly-Val-CO$_2$H result. No cleavage is seen at the other Thr-Gly residues in the original tetradecapeptide substrate indicating the extreme specificity of the antibody to only the site of introduction of the tripeptide transition state analog isostere of the invention.

We Claim:

1. A catalytic antibody elicited by an antigen comprising the boron-containing hapten of formula I,

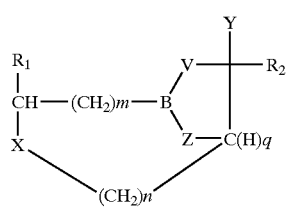

(I)

wherein

R$_1$ and R$_2$ may be the same or different and each is a side chain of a naturally occurring amino acid, a hydroxy containing side chain of a naturally occurring amino acid wherein said protecting group, a primary amido containing side chain of a naturally occurring amino acid wherein said amido group may be glycosylated, (C$_2$–C$_4$)alkyl, —CH$_2$CH(CO$_2$H)$_2$, —(CH$_2$)$_2$S(O)CH$_3$, —(CH$_2$)$_2$S(O)$_2$CH$_3$, —(CH$_2$)$_3$NH$_2$ or —(CH$_2$)$_3$ONHC(=NH)NH$_2$;

V is O, CH$_2$ or NH;

X is hydrogen, oxygen, amino, amino protected by a terminal amino protecting group, amino bonded to the C terminus of a naturally occurring amino acid to form a peptide bond, amino bonded to the C terminus of a peptide to form a peptide bond, alkene, (C$_1$–C$_9$)alkyl, (C$_1$–C$_9$)alkoxy or phenyl, phenoxy, cyclohexyl, phenylthio, phenylsulfinyl or phenylsulfonyl, wherein the aforementioned phenyl groups may be unsubstituted or mono-, di- or trisubstituted by halogen, (C$_1$–C$_4$)alkoxy or (C$_1$–C$_4$)alkoxycarbonyl;

Y is hydrogen, carboxyl, carboxyl protected by a terminal carboxyl protecting group, a carbonyl bonded to the N terminus of a peptide through a peptide bond, (C$_1$–C$_9$) alkyl, (C$_1$–C$_9$)alkoxy, phenyl phenoxy, cyclohexyl, phenylthio, phenylsulfinyl or phenylsulfonyl wherein the aforementioned phenyl groups may be unsubstituted or mono-, di- or trisubstituted by halogen, (C$_1$–C$_4$)alkyl, (C$_1$–C$_4$)alkoxy or (C$_1$–C$_4$)alkoxycarbonyl; and wherein Z is O, CH$_2$ or NH;

m is 0 or an integer from 1 to 10;

n is 0 or 1; and q is 1 or 2 provided that if q is 2, then n=0 and there is no bond between X and the carbon bound to Z.

2. A catalytic antibody which catalyzes a chemical reaction of interest and which is elicited through in vitro or in vivo techniques by an antigen comprising the boron-containing hapten of formula I,

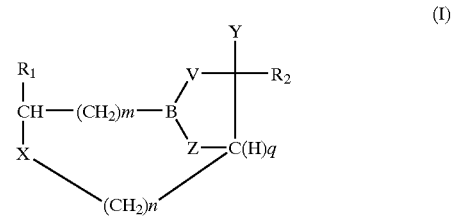

(I)

wherein

R$_1$ and R$_2$ may be the same or different and each is a side chain of a naturally occurring amino acid, a hydroxy containing side chain of a naturally occurring amino acid wherein said hydroxy group may be glycosylated, phosphorylated, sulphonylated or protected by a hydroxy protecting group, a primary amido containing side chain of a naturally occurring amino acid wherein said amido group may be glycosylated, (C$_2$–C$_4$)alkyl, —CH$_2$CH(CO$_2$H)$_2$, —(CH$_2$)$_2$S(O)CH$_3$, —(CH$_2$)$_2$S(O)$_2$CH$_3$, —(CH$_2$)$_3$NH$_2$ or —(CH$_2$)$_3$ONHC(=NH)NH$_2$;

V is O, CH$_2$ or NH;

X is hydrogen, oxygen, amino, amino protected by a terminal amino protecting group, amino bonded to the C terminus of a naturally occurring amino acid to form a peptide bond, amino bonded to the C terminus of a peptide to form a peptide bond, alkene, (C$_1$–C$_9$)alkyl, ($C_1$–$C_9$)alkoxy or phenyl, phenoxy, cyclohexyl, phenylthio, phenylsulfinyl or phenylsulfonyl, wherein the aforementioned phenyl groups may be unsubstituted or mono-, di- or trisubstituted by halogen, ($C_1$–$C_4$)alkoxy or ($C_1$–$C_4$)alkoxycarbonyl;

Y is hydrogen, carboxyl, carboxyl protected by a terminal carboxyl protecting group, a carbonyl bonded to the N terminus of a peptide through a peptide bond, ($C_1$–$C_9$) alkyl, ($C_1$–$C_9$)alkoxy, phenyl phenoxy, cyclohexyl, phenylthio, phenylsulfinyl or phenylsulfonyl wherein the aforementioned phenyl groups may be unsubstituted or mono-, di- or trisubstituted by halogen, ($C_1$–$C_4$)alkyl, ($C_1$–$C_4$)alkoxy or ($C_1$–$C_9$)alkoxycarbonyl; and wherein Z is O, $CH_2$ or NH;

m is 0 or an integer from 1 to 10;

n is 0 or 1; and q is 1 or 2 provided that if q is 2, then n=0 and there is no bond between X and the carbon bound to Z, said catalytic antibody having been prepared by a process comprising the steps of:

(a) exposing cells capable of producing antibodies to said antigen and thereby generating antibody producing cells;

(b) hybridizing said antibody producing cells with myeloma cells and thereby generating a plurality of hybridoma cells each producing monoclonal antibodies; and (c) screening said plurality of monoclonal antibodies to identify a monoclonal antibody which catalyzes said chemical reaction of interest.

3. A method for producing catalytic antibodies which catalyze a chemical reaction of interest and which are elicited through in vitro or in vivo techniques by an antigen comprising the boron-containing hapten of formula I,

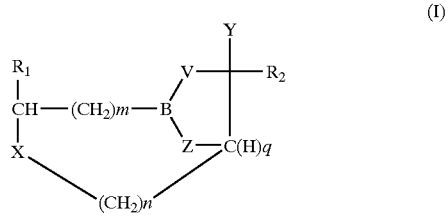

(I)

wherein $R_1$ and $R_2$ may be the same or different and each is a side chain of a naturally occurring amino acid, a hydroxy containing side chain of a naturally occurring amino acid wherein said hydroxy group may be glycosylated, phosphorylated, sulphonylated or protected by a hydroxy protecting group, a primary amido containing side chain of a naturally occurring amino acid wherein said amido group may be glycosylated, ($C_2$–$C_4$)alkyl, —$CH_2CH(CO_2H)_2$, —$(CH_2)_2S(O)CH_3$, —$(CH_2)_2S(O)_2CH_3$, —$(CH_2)_3NH_2$ or —$(CH_2)_3$ ONHC(=NH)$NH_2$;

V is O, CH 2 or NH;

X is hydrogen, oxygen, amino, amino protected by a terminal amino protecting group, amino bonded to the C terminus of a naturally occurring amino acid to form a peptide bond, amino bonded to the C terminus of a peptide to form a peptide bond, alkene, ($C_1$–$C_9$)alkyl, ($C_1$–$C_9$)alkoxy or phenyl, phenoxy, cyclohexyl, phenylthio, phenylsulfinyl or phenylsulfonyl, wherein the aforementioned phenyl groups may be unsubstituted or mono-, di- or trisubstituted by halogen, ($C_1$–$C_4$)alkoxy or ($C_1$–$C_4$)alkoxycarbonyl;

Y is hydrogen, carboxyl, carboxyl protected by a terminal carboxyl protecting group, a carbonyl bonded to the N terminus of a peptide through a peptide bond, ($C_1$–$C_9$) alkyl, ($C_1$–$C_9$)alkoxy, phenyl phenoxy, cyclohexyl, phenylthio, phenylsulfinyl or phenylsulfonyl wherein the aforementioned phenyl groups may be unsubstituted or mono-, di- or trisubstituted by halogen, ($C_1$–$C_4$)alkyl, ($C_1$–$C_4$)alkoxy or ($C_1$–$C_4$)alkoxycarbonyl; and wherein Z is O, $CH_2$ or NH;

m is 0 or an integer from 1 to 10;

n is 0 or 1; and q is 1 or 2 provided that if q is 2, then n=0 and there is no bond between X and the carbon bound to Z, wherein said method comprises the steps of:

(a) exposing cells capable of producing antibodies to said antigen and thereby generating antibody producing cells;

(b) hybridizing said antibody producing cells with myeloma cells and thereby (generating a plurality of hybridoma cells each producing monoclonal antibodies; and (c) screening said plurality of monoclonal antibodies to identify a monoclonal antibody which catalyzes said chemical reaction of interest.

4. A method for catalyzing the cleavage or formation of a peptide linkage or an ester bond in a molecule comprising contacting said molecule with an effective amount of a catalytic antibody elicited by an antigen comprising the boron-containing hapten of formula I,

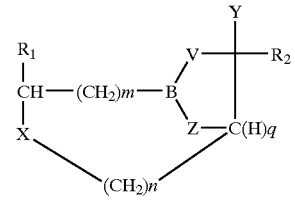

(I)

wherein $R_1$ and $R_2$ may be the same or different and each is a side chain of a naturally occurring amino acid, a hydroxy containing side chain of a naturally occurring amino acid wherein said hydroxy group may be glycosylated, phosphorylated, sulphonylated or protected by a hydroxy protecting group, a primary amido containing side chain of a naturally occurring amino acid wherein said amido group may be glycosylated, ($C_2$–$C_4$)alkyl, —$CH_2CH(CO_2H)_2$, —$(CH_2)_2S(O)CH_3$, —$(CH_2)_2S(O)_2CH_3$, —$(CH_2)_3NH_2$ or —$(CH_2)_3$ ONHC(=NH)$NH_2$;

V is O, CH 2 or NH;

X is hydrogen, oxygen, amino, amino protected by a terminal amino protecting group, amino bonded to the C terminus of a naturally occurring amino acid to form a peptide bond, amino bonded to the C terminus of a peptide to form a peptide bond, alkene, ($C_1$–$C_9$)alkyl, ($C_1$– $C_9$)alkoxy or phenyl, phenoxy, cyclohexyl, phenylthio, phenylsulfinyl or phenylsulfonyl, wherein the aforementioned phenyl groups may be unsubstituted or mono-, di- or trisubstituted by halogen, ($C_1$–$C_4$)alkoxy or ($C_1$–$C_4$)alkoxycarbonyl;

Y is hydrogen, carboxyl, carboxyl protected by a terminal carboxyl protecting group, a carbonyl bonded to the N terminus of a peptide through a peptide bond, ($C_1$–$C_9$) alkyl, ($C_1$–$C_9$)alkoxy, phenyl phenoxy, cyclohexyl, phenylthio, phenylsulfinyl or phenylsulfonyl wherein the aforementioned phenyl groups may be unsubstituted or mono-, di- or trisubstituted by halogen, ($C_1$–$C_4$)alkyl, ($C_1$–$C_4$)alkoxy or ($C_1$–$C_4$)alkoxycarbonyl; and wherein Z is O, $CH_2$ or NH;

m is 0 or an integer from 1 to 10;

n is 0 or 1; and q is 1 or 2 provided that if q is 2, then n=0 and there is no bond between X and the carbon bound to Z.

5. A method for catalyzing the cleavage or formation of a specific peptide linkage or an ester bond within a specific amino acid sequence of a molecule which comprises: contacting said molecule with an effective amount of a catalytic antibody elicited with a boron-containing hapten of formula I,

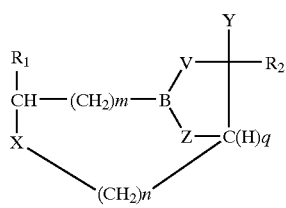

(I)

wherein $R_1$ and $R_2$ may be the same or different and each is a side chain of a naturally occurring amino acid, a hydroxy containing side chain of a naturally occurring amino acid wherein said hydroxy group may be glycosylated, phosphorylated, sulphonylated or protected by a hydroxy protecting group, a primary amido containing side chain of a naturally occurring amino acid wherein said amido group may be glycosylated, ($C_2$–$C_4$)alkyl, —$CH_2CH(CO_2H)_2$, —$(CH_2)_2S(O)CH_3$, —$(CH_2)_2S(O)_2CH_3$, —$(CH_2)_3NH_2$ or —$(CH_2)_3ONHC(=NH)NH_2$;

V is O, $CH_2$ or NH;

X is hydrogen, oxygen, amino, amino protected by a terminal amino protecting group, amino bonded to the C terminus of a naturally occurring amino acid to form a peptide bond, amino bonded to the C terminus of a peptide to form a peptide bond, alkene, ($C_1$–$C_9$)alkyl, ($C_1$–$C_9$)alkoxy or phenyl, phenoxy, cyclohexyl, phenylthio, phenylsulfinyl or phenylsulfonyl, wherein the aforementioned phenyl groups may be unsubstituted or mono-, di- or trisubstituted by halogen, ($C_1$–$C_4$)alkoxy or ($C_1$–$C_4$)alkoxycarbonyl;

Y is hydrogen, carboxyl, carboxyl protected by a terminal carboxyl protecting group, a carbonyl bonded to the N terminus of a peptide through a peptide bond, ($C_1$–$C_9$) alkyl, ($C_1$–$C_9$)alkoxy, phenyl phenoxy, cyclohexyl, phenylthio, phenylsulfinyl or phenylsulfonyl wherein the aforementioned phenyl groups may be unsubstituted or mono-, di- or trisubstituted by halogen, ($C_1$–$C_4$)alkyl, ($C_1$–$C_4$)alkoxy or ($C_1$–$C_4$)alkoxycarbonyl; and wherein Z is O, $CH_2$ or NH;

m is 0 or an integer from 1 to 10;

n is 0 or 1; and q is 1 or 2 provided that if q is 2, then n=0 and there is no bond between X and the carbon bound to Z, said hapten being homologous to said specific amino acid sequence.

* * * * *